(12) United States Patent
Nagamine et al.

(10) Patent No.: US 9,411,227 B2
(45) Date of Patent: Aug. 9, 2016

(54) RESIST COMPOSITION, METHOD OF FORMING RESIST PATTERN, COMPOUND, AND POLYMERIC COMPOUND

(71) Applicant: Tokyo Ohka Kogyo Co., Ltd., Kawasaki (JP)

(72) Inventors: Takashi Nagamine, Kawasaki (JP); Junichi Tsuchiya, Kawasaki (JP); Masatoshi Arai, Kawasaki (JP); Yoshitaka Komuro, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/597,555

(22) Filed: Jan. 15, 2015

(65) Prior Publication Data

US 2015/0198881 A1 Jul. 16, 2015

(30) Foreign Application Priority Data

Jan. 16, 2014 (JP) ................. 2014-006273

(51) Int. Cl.
| | |
|---|---|
| *G03F 7/039* | (2006.01) |
| *C08F 220/28* | (2006.01) |
| *G03F 7/038* | (2006.01) |
| *C07C 69/40* | (2006.01) |
| *C08F 220/38* | (2006.01) |

(52) U.S. Cl.
CPC ............. *G03F 7/038* (2013.01); *C07C 69/40* (2013.01); *C08F 220/28* (2013.01); *G03F 7/0397* (2013.01); *C07C 2101/06* (2013.01); *C07C 2101/14* (2013.01); *C07C 2101/18* (2013.01); *C07C 2102/42* (2013.01); *C07C 2103/74* (2013.01); *C08F 220/38* (2013.01); *C08F 2220/382* (2013.01); *C08F 2220/387* (2013.01)

(58) Field of Classification Search
CPC ....... G03F 7/004; G03F 7/039; G03F 7/0392; G03F 7/0397; C07C 69/604; C07C 69/74; C08F 222/10
See application file for complete search history.

(56) References Cited

U.S. PATENT DOCUMENTS

| | | | |
|---|---|---|---|
| 6,200,725 B1 | 3/2001 | Takechi et al. | |
| 2004/0110085 A1 | 6/2004 | Iwai et al. | |
| 2005/0227174 A1 | 10/2005 | Hatakeyama et al. | |
| 2007/0072115 A1 | 3/2007 | Hatakeyama et al. | |
| 2007/0275324 A1 | 11/2007 | Allen et al. | |
| 2008/0187860 A1 | 8/2008 | Tsubaki et al. | |
| 2009/0197204 A1 | 8/2009 | Shiono et al. | |
| 2009/0214982 A1 | 8/2009 | Shimizu et al. | |
| 2009/0269694 A1 * | 10/2009 | Shimizu et al. | ............ 430/270.1 |
| 2009/0317743 A1 | 12/2009 | Shiono et al. | |
| 2010/0310985 A1 | 12/2010 | Mori et al. | |
| 2011/0117499 A1 | 5/2011 | Matsumiya et al. | |
| 2012/0149916 A1 | 6/2012 | Utsumi et al. | |
| 2015/0118616 A1 * | 4/2015 | Mori et al. | ............ 430/270.1 |

FOREIGN PATENT DOCUMENTS

| | | |
|---|---|---|
| JP | A-10-301284 | 11/1998 |
| JP | A-2000-056459 | 2/2000 |
| JP | 2002-131917 | * 5/2002 |
| JP | A-2003-241385 | 8/2003 |
| JP | A-2007-140188 | 6/2007 |
| JP | A-2009-223300 | 10/2009 |
| JP | A-2009-244395 | 10/2009 |
| JP | A-2010-002870 | 1/2010 |
| JP | A-2010-032994 | 2/2010 |
| JP | A-2010-277043 | 12/2010 |
| JP | A-2011-013569 | 1/2011 |
| JP | A-2011-128226 | 6/2011 |
| JP | A-2012-162498 | 8/2012 |

OTHER PUBLICATIONS

Machine translation of JP 2002-131917, published on May 9, 2002.*
Office Action in U.S. Appl. No. 14/519,879, mailed Jul. 6, 2015.
Final Office Action in U.S. Appl. No. 14/519,879, mailed Nov. 4, 2015.
Notice of Allowance in U.S. Appl. No. 14/519,879 dated Apr. 27, 2016.

* cited by examiner

*Primary Examiner* — Anca Eoff
(74) *Attorney, Agent, or Firm* — Knobbe Martens Olson & Bear LLP

(57) ABSTRACT

A polymeric compound having a structural unit represented by general formula (a0-1), and a resist composition containing the same (in which R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-C(=O)O— or $Va^{01}$-OC(=O)—; $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

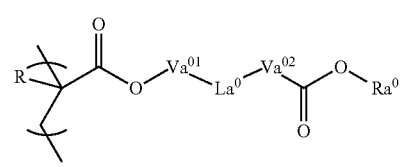

(a0-1)

17 Claims, No Drawings

RESIST COMPOSITION, METHOD OF FORMING RESIST PATTERN, COMPOUND, AND POLYMERIC COMPOUND

TECHNICAL FIELD

The present invention relates to a resist composition, a method of forming a resist pattern, a compound, and a polymeric compound.

The present application claims priority to Japanese Patent Application No. 2014-006273, filed Jan. 16, 2014, the entire content of which is incorporated herein by reference.

DESCRIPTION OF RELATED ART

Techniques (pattern-forming techniques) in which a fine pattern is formed on top of a substrate, and a lower layer beneath that pattern is then fabricated by conducting etching with this pattern as a mask are widely used in the production of semiconductor devices and liquid display device. These types of fine patterns are usually formed from an organic material, and are formed using a lithography method or a nanoimprint method or the like. In lithography techniques, for example, a resist film composed of a resist material containing a base component such as a resin is formed on a support such as a substrate, and the resist film is subjected to selective exposure of radial rays such as light or electron beam, followed by development, thereby forming a resist pattern having a predetermined shape on the resist film. Using this resist pattern as a mask, a semiconductor or the like is produced by conducting a step in which the substrate is processed by etching.

The aforementioned resist material can be classified into positive types and negative types. Resist materials in which the exposed portions exhibit increased solubility in a developing solution is called a positive type, and a resist material in which the exposed portions exhibit decreased solubility in a developing solution is called a negative type.

In general, an aqueous alkali solution (alkali developing solution) such as an aqueous solution of tetramethylammonium hydroxide (TMAH) is used as the developing solution. Alternatively, a solvent containing an organic solvent (organic developing solution) such as an aromatic organic solvent, an aliphatic hydrocarbon organic solvent, an ether organic solvent, a ketone organic solvent, an ester organic solvent, an amide organic solvent or an alcohol organic solvent is used as the developing solution.

In recent years, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

As shortening the wavelength of the exposure light source progresses, it is required to improve various lithography properties of the resist material, such as the sensitivity to the exposure light source and a resolution capable of reproducing patterns of minute dimensions. As resist materials which satisfy such requirements, chemically amplified resists are known.

As a chemically amplified composition, a composition including a base material component that exhibits a changed solubility in a developing solution under the action of acid and an acid-generator component that generates acid upon exposure is generally used. For example, in the case where an alkali developing solution is used as a developing solution (alkali developing process), a base component which exhibits increased solubility in an alkali developing solution under action of acid is used.

Conventionally, a resin (base resin) is typically used as the base component of a chemically amplified resist composition. Resins that contain structural units derived from (meth) acrylate esters within the main chain (acrylic resins) are the mainstream as base resins for chemically amplified resist compositions that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position. The term "(meth) acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

In general, the base resin for a chemically amplified resist composition contains a plurality of kinds of structural units for improving lithography properties and the like. For example, a structural unit having a lactone structure and a structural unit having a polar group such as a hydroxy group are used, as well as a structural unit having an acid decomposable group which is decomposed by the action of an acid generated from the acid generator to form an alkali soluble group (for example, see Patent Document 1). When the base resin is an acrylic resin, as the acid decomposable group, in general, resins in which the carboxy group of (meth)acrylic acid or the like is protected with an acid dissociable group such as a tertiary alkyl group or an acetal group are used.

The positive tone process using a combination of a positive chemically amplified resist composition (i.e., a chemically amplified resist composition which exhibits increased solubility in an alkali developing solution upon exposure) and an alkali developing solution is advantageous over a negative tone development process in which a negative type, chemically amplified resist composition is used in combination with an alkali developing solution in that the structure of the photomask can be simplified, and the characteristics of the formed resist pattern are excellent. For these reasons, currently, positive-tone development process using a combination of a positive chemically amplified resist composition and an alkali developing solution is mainly employed in the formation of an extremely fine pattern.

In the case where a positive-tone development process is applied, when a resist film obtained by coating the positive chemically amplified resist composition on a substrate is selectively exposed, the acid decomposable groups in the base resin is decomposed by the action of acid generated from the acid generator and the like, such that the exposed portions change from an insoluble state to a soluble state in an alkali developing solution. On the other hand, the unexposed portions remain insoluble in an alkali developing solution. Therefore, by developing with an alkali developing solution, a dissolution contrast can be obtained between the exposed portions and the unexposed portions, and a positive resist pattern can be formed.

Conventionally, for improving the lithography properties, there has been proposed a chemically amplified resist composition using, as a base resin, a polymeric compound having a structural unit having an acid decomposable group and a long side chain introduced with an oxygen atom (—O—) and a carbonyl group (see Patent Document 2).

In the formation of an extremely small pattern, a method in which regions where the optical strength becomes weak are selectively dissolved and removed to form a resist pattern (negative pattern) is useful.

As a method of forming a negative-tone resist pattern, a method is known in which a chemically amplified resist composition used in a positive-tone developing process (which is the mainstream) and a developing solution containing an organic solvent (organic developing solution) are used in combination.

DOCUMENTS OF RELATED ART

Patent Literature

[Patent Document 1] Japanese Unexamined Patent Application, First Publication No. 2003-241385

[Patent Document 2] Japanese Unexamined Patent Application, First Publication No. 2009-223300

SUMMARY OF THE INVENTION

Due to further improvement in the performance and downsize of electronic devices, in the pattern formation in the production of semiconductor devices, further improvement in the lithography properties and the resist pattern shape are demanded. However, there was still room for improvement in the shape of a resist pattern formed by using a conventional resist composition, and there are demands for further improvement in lithography properties and the like.

The present invention takes the above circumstances into consideration, with an object of further improving the shape of a resist pattern.

As a result of the studies of the present inventors, they have found that, by introducing a specific structure into a side chain portion of a polymeric compound used as the base resin, a large dissolution contrast can be obtained between the exposed portions and unexposed portions of the resist film. The present invention has been completed based on this finding.

Specifically, a first aspect of the present invention is a resist composition which generates acid upon exposure and exhibits changed solubility in a developing solution under action of acid, and which includes a base component (A) which exhibits changed solubility in a developing solution under action of acid, the base component (A) including a polymeric compound (A1) having a structural unit (a0) represented by general formula (a0-1) shown below.

[Chemical Formula 1]

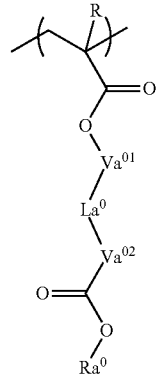

(a0-1)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^{0}$— represents $Va^{01}$-C(=O)O— or $Va^{01}$-OC(=O)—; and $Ra^{0}$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

A second aspect of the present invention is a method of forming a resist pattern, including: using a resist composition according to the first aspect to form a resist film on a substrate, exposing the resist film, and developing the exposed resist film to form a resist pattern.

A third aspect of the present invention is a compound represented by general formula (m-a0) shown below.

[Chemical Formula 2]

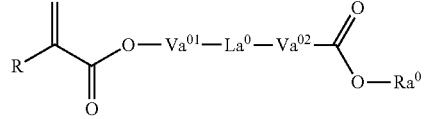

(m-a0)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^{0}$— represents $Va^{01}$-C(=O)O— or $Va^{01}$-OC(=O)—; and $Ra^{0}$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

A fourth aspect of the present invention is a polymeric compound having a structural unit represented by general formula (a0-1) shown below.

[Chemical Formula 3]

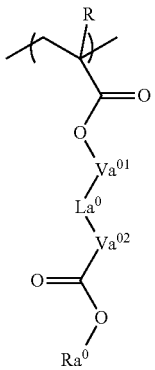

(a0-1)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-C(=O)O— or $Va^{01}$-OC(=O)—; and $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

According to the resist composition and method of forming the resist pattern of the present invention, a resist pattern with an excellent shape.

The polymeric compound of the present invention is useful as a resin for the aforementioned resist composition capable of forming a resist pattern with an excellent shape. Further, the compound of the present invention is useful as a raw monomer of the aforementioned polymeric compound.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The expression "may have a substituent" means that a case where a hydrogen atom (—H) is substituted with a monovalent group, or a case where a methylene (—$CH_2$—) group is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2$=CH—COOH) has been substituted with an organic group.

The acrylate ester may have the hydrogen atom bonded to the carbon atom on the α-position substituted with a substituent. The substituent ($R^{\alpha 0}$) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, an acrylate ester having the hydrogen atom bonded to the carbon atom on the α-position substituted with a substituent ($R^{\alpha 0}$) in which the substituent has been substituted with a substituent containing an ester bond (e.g., an itaconic acid diester), or an acrylic acid having the hydrogen atom bonded to the carbon atom on the α-position substituted with a substituent ($R^{\alpha 0}$) in which the substituent has been substituted with a hydroxyalkyl group or a group in which the hydroxy group within a hydroxyalkyl group has been modified (e.g., α-hydroxyalkyl acrylate ester) can be mentioned as an acrylate ester having the hydrogen atom bonded to the carbon atom on the α-position substituted with a substituent. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

A "structural unit derived from acrylamide" refers to a structural unit that is formed by the cleavage of the ethylenic double bond of acrylamide.

The acrylamide may have the hydrogen atom bonded to the carbon atom on the α-position substituted with a substituent, and may have either or both terminal hydrogen atoms on the amino group of acrylamide substituted with a substituent. A carbon atom on the α-position of an acrylamide refers to the carbon atom bonded to the carbonyl group, unless specified otherwise.

As the substituent which substitutes the hydrogen atom on the α-position of acrylamide, the same substituents as those described above for the substituent ($R^{\alpha 0}$) on the α-position of the aforementioned α-position of the aforementioned α-substituted acrylate ester can be mentioned.

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) of hydroxystyrene refers to the carbon atom having the benzene ring bonded thereto, unless specified otherwise.

As the substituent which substitutes the hydrogen atom on the α-position of hydroxystyrene, the same substituents as those described above for the substituent ($R^{\alpha 0}$) on the α-position of the aforementioned α-position of the aforementioned α-substituted acrylate ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) of vinylbenzoic acid refers to the carbon atom having the benzene ring bonded thereto, unless specified otherwise.

The term "styrene" is a concept including styrene and compounds in which the hydrogen atom at the α-position of styrene is substituted with other substituent such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

<<Resist Composition>>

The resist composition according to a first aspect of the present invention is a resist composition which generates acid upon exposure and exhibits changed solubility in a developing solution under action of acid, and which includes a base component (A) which exhibits changed solubility in a developing solution under action of acid (hereafter, also referred to as "component (A)").

When a resist film is formed using the resist composition and the formed resist film is subjected to a selective exposure, acid is generated at exposed portions of the resist film, and the generated acid acts on the component (A) to change the solubility of the component (A) in a developing solution, whereas the solubility of the component (A) in a developing solution is not changed at unexposed portions of the resist film, thereby generating difference in solubility in a developing solution between exposed portions and unexposed portions. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition.

The resist composition of the present invention may be either a positive resist composition or a negative resist composition.

Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment.

The resist composition of the present embodiment has a function of generating acid upon exposure, and in the resist composition, the component (A) may generate acid upon exposure, or an additive component other than the component (A) may generate acid upon exposure.

Specifically, the resist composition of the present embodiment may be a resist composition (1) containing an acid generator component (B) which generates acid upon exposure (hereafter, referred to as "component (B)");

a resist composition (2) in which the component (A) is a component which generates acid upon exposure; or a resist composition (3) in which the component (A) is a component which generates acid upon exposure, and further containing an acid generator component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits changed solubility in a developing solution under action of acid, the component (A1) described later is preferably a polymeric compound which generates acid upon exposure and exhibits changed solubility in a developing solution under action of acid. As the polymeric compound, a resin having a structural unit (a6) which generates acid upon exposure can be used. The structural unit (a6) which generates acid upon exposure will be described later.

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" or a "polymeric compound" refers to a polymer having a molecular weight of 1,000 or more.

As the molecular weight of the polymer, the weight average molecular weight in terms of the polystyrene equivalent value determined by gel permeation chromatography (GPC) is used.

As the component (A) usable in the resist composition of the present embodiment, at least the component (A1) (described later) is used, and a polymeric compound and/or a low molecular weight compound may be used in combination with the component (A1).

[Component (A1)]

The component (A1) is a polymeric compound including a structural unit (a0) represented by general formula (a0-1).

When a resist film formed using the resist composition containing the component (A1) is exposed, at least part of the structure within the structural unit (a0) is cleaved by the action of acid, and the polarity is increased. As a result, the resist composition of the present embodiment becomes a positive-type in an alkali developing process, and a negative-type in a solvent developing process. Since the polarity of the component (A1) is changed prior to and after exposure, by using the component (A1), an excellent development contrast can be achieved not only in an alkali developing process, but also in a solvent developing process.

More specifically, in the case of applying an alkali developing process, the component (A1) is substantially insoluble in an alkali developing solution prior to exposure, but when acid is generated upon exposure, the action of this acid causes an increase in the polarity of the base component, thereby increasing the solubility of the component (A1) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, in the case of a solvent developing process, the component (A1) exhibits high solubility in an organic developing solution prior to exposure, and when acid is generated upon exposure, the polarity of the component (A1) is increased by the action of the generated acid, thereby decreasing the solubility of the component (A1) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

(Structural Unit (a0))

The structural unit (a0) is represented by general formula (a0-1) shown below.

[Chemical Formula 4]

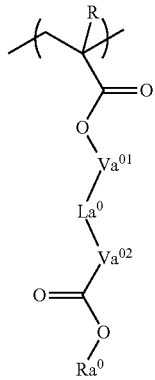

(a0-1)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^{0}$— represents $Va^{01}$-C(=O)O— or $Va^{01}$-OC(=O)—; and $Ra^{0}$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

In general formula (a0-1), R represents a hydrogen atom, an alkyl group of 1 to 5 carbon atoms or a halogenated alkyl group of 1 to 5 carbon atoms.

As the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a0-1), $Va^{01}$ and $Va^{02}$ each independently represents a hydrocarbon group of 2 to 10 carbon atoms.

The hydrocarbon group for $Va^{01}$ and $Va^{02}$ may independently be an aliphatic hydrocarbon group or an aromatic hydrocarbon group.

The aliphatic hydrocarbon group as the hydrocarbon group for $Va^{01}$ and $Va^{02}$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 2 to 10 carbon atoms, more preferably 2 to 6, still more preferably 2 to 5, still more preferably 2 or 3, and most preferably 2.

Specific examples of the linear aliphatic hydrocarbon group (a linear alkylene group) include a methylene group

[—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

Specific examples of the branched aliphatic hydrocarbon group (branched alkylene group) include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH($CH_3$)$CH_2CH_2CH_2$—, and —$CH_2$CH($CH_3$)$CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group (linear alkylene group) or the aforementioned branched aliphatic hydrocarbon group (branched alkylene group).

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 10 carbon atoms. Examples of the polycycloalkane include adamantane, norbornane, isobornane and tricyclodecane.

The aromatic hydrocarbon group as the divalent hydrocarbon group for $Va^{o1}$ and $Va^{o2}$ is a hydrocarbon group having an aromatic ring.

The aromatic hydrocarbon group preferably has 3 to 10 carbon atoms, more preferably 5 to 10 carbon atoms, and still more preferably 6 to 10 carbon atoms.

Examples of the aromatic ring contained in the aromatic hydrocarbon group include aromatic hydrocarbon rings, such as benzene and naphthalene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group or a phenethyl group). The alkylene group (alkyl chain within the arylalkyl group) preferably has 1 to 4 carbon atom, more preferably 1 or 2, and most preferably 1.

Among the above examples, as $Va^{o1}$ and $Va^{o2}$, an aliphatic hydrocarbon group is preferable, a linear or branched aliphatic hydrocarbon group is more preferable, and a linear aliphatic hydrocarbon group (linear alkylene group) is still more preferable.

$Va^{o1}$ and $Va^{o2}$ may be the same or different from each other.

In formula (a0-1), $Va^{o1}$-$La^o$— represents $Va^{o1}$-C(=O)O— or $Va^{o1}$-OC(=O)—, and is preferably $Va^{o1}$-OC(=O)—.

In formula (a0-1), $Ra^o$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

The "acid dissociable group" refers to both (i) a group in which the bond between the acid dissociable group and the adjacent atom is cleaved by the action of acid; and (ii) a group in which one of the bonds is cleaved by the action of acid, and then a decarboxylation reaction occurs, thereby cleaving the bond between the acid dissociable group and the adjacent atom.

In the structural unit (a0), by the action of acid, $Ra^o$ is dissociated, and a polar group (carboxy group) is formed on the terminal of the side-chain of structural unit (a0). It is necessary that $Ra^o$ is a group which exhibits a polarity lower than that of the polar group (carboxy group) to be formed on the terminal of the side-chain of the structural unit (a0). Therefore, when $Ra^o$ is dissociated by the action of acid, a polar group (carboxy group) exhibiting higher polarity than $Ra^o$ is formed, such that the polarity of the structural unit (a0) is increased. As a result, the polarity of the entire component (A1) is increased. By the increase in the polarity, the solubility in an alkali developing solution changes, and the solubility in an alkali developing solution is relatively increased, whereas the solubility in an organic developing solution is relatively decreased.

The branched hydrocarbon group for $Ra^o$ has 8 or more carbon atoms, preferably 8 to 20, more preferably 8 to 10, and most preferably 8.

The monocyclic hydrocarbon group for $Ra^o$ has 4 or more carbon atoms, preferably 5 to 15, and more preferably 6 to 10.

The polycyclic hydrocarbon group for $Ra^o$ (provided that a methyl adamantyl group is excluded) preferably has 7 or more carbon atoms, more preferably 8 to 16, and still more preferably 11 to 14.

As the "acid dissociable group" for $Ra^o$, specifically, among the examples of acid dissociable groups for the structural unit (a1) described later, a branched hydrocarbon group of 8 or more carbon atoms, a monocyclic hydrocarbon group of 4 or more carbon atoms and a polycyclic hydrocarbon group (provided that a methyl adamantyl group is excluded) can be mentioned.

In the case where $Ra^o$ represents a monocyclic hydrocarbon group, in a group represented by general formula (a1-r2-1), $Ra'^{10}$ is preferably a branched alkyl group. The aliphatic monocyclic group constituted by $Ra'^{11}$ is preferably a group in which 1 hydrogen atom has been removed from a monocycloalkane of 3 to 8 carbon atoms. Specific examples of the monocycloalkane include cyclopentane, cyclohexane and cyclooctane, and cyclopentane or cyclohexane is preferable.

In the case where $Ra^o$ represents a polycyclic hydrocarbon group, in a group represented by general formula (a1-r2-1), $Ra'^{10}$ is preferably a branched alkyl group. The aliphatic polycyclic group constituted by $Ra'^{11}$ is preferably a group in which 1 hydrogen atom has been removed from a polycycloalkane of 7 to 12 carbon atoms. Specific examples of the polycycloalkane include adamantane, norbornane, isobornane, tricyclodecane and tetracyclododecane, and adamantane or norbornane is preferable.

Specific examples of $Ra^0$ are shown below. In the formulae, "*" represents a valence bond (the same applies hereafter).
[Chemical Formula 5]
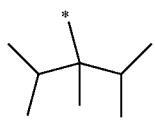
(r-pr-c1)
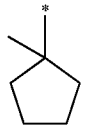
(r-pr-s1)
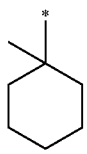
(r-pr-s2)
(r-pr-s3)
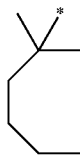
(r-pr-s4)
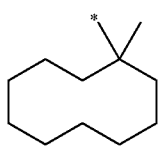
(r-pr-s5)
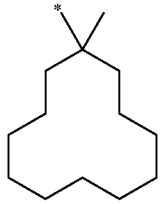
(r-pr-s6)
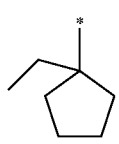
(r-pr-s7)
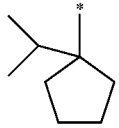
(r-pr-s8)
-continued
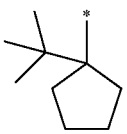
(r-pr-s9)
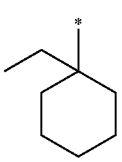
(r-pr-s10)
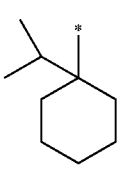
(r-pr-s11)
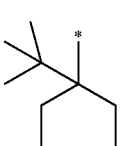
(r-pr-s12)
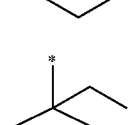
(r-pr-s13)
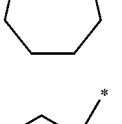
(r-pr-s14)
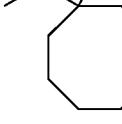
(r-pr-s15)
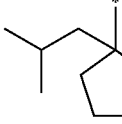
(r-pr-s16)
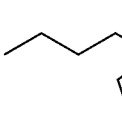
(r-pr-s17)
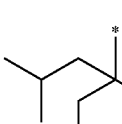
(r-pr-s18)
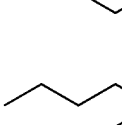

-continued

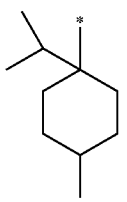

[Chemical Formula 6]

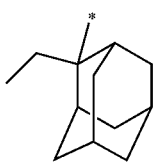
(r-pr-s19)

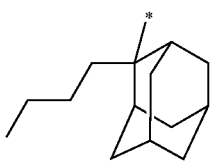
(r-pr-m2)

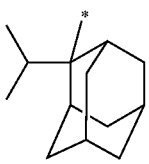
(r-pr-m3)

(r-pr-m4)

(r-pr-m5)

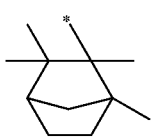
(r-pr-m6)

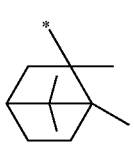
(r-pr-m7)

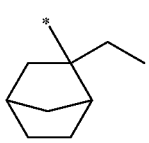
(r-pr-m8)

(r-pr-m9)

(r-pr-m10)

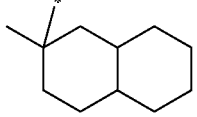
(r-pr-m11)

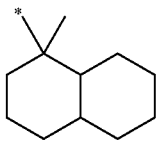
(r-pr-m12)

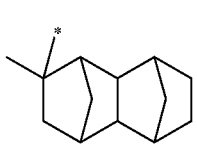
(r-pr-m13)

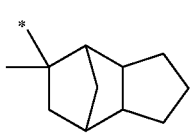
(r-pr-m14)

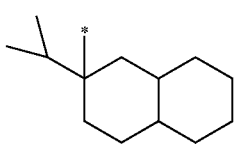
(r-pr-m15)

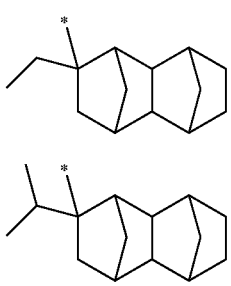
(r-pr-m16)

(r-pr-m17)

Among the above examples, as $R^{a0}$, in terms of more reliably obtaining a resist pattern with an excellent shape, an acid dissociable, branched hydrocarbon group of 8 or more carbon atoms or an acid dissociable, monocyclic hydrocarbon group of 4 or more carbon atoms is preferable, and in terms of more reliably obtaining excellent lithography properties, an acid dissociable, branched hydrocarbon group of 8 or more carbon atoms is more preferable.

Specific examples of structural unit represented by formula (a0-1) are shown below. In the formulae shown below, $R^\alpha$ represents a hydrogen atom, a methyl group or a trifluoromethyl group.

[Chemical Formula 7]

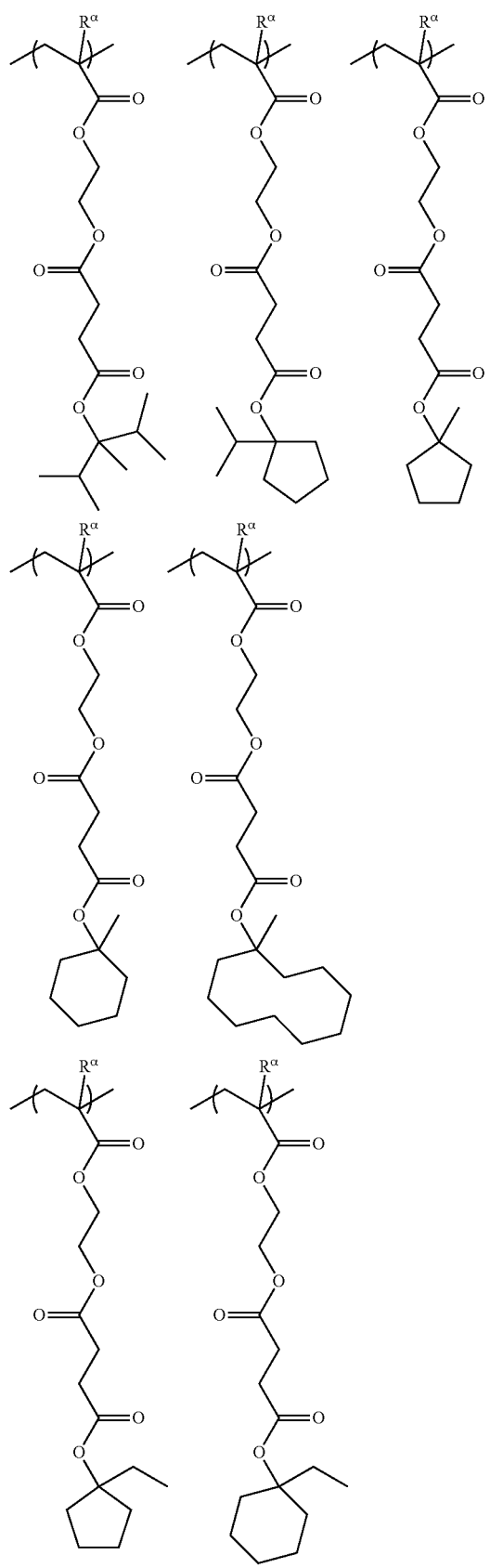

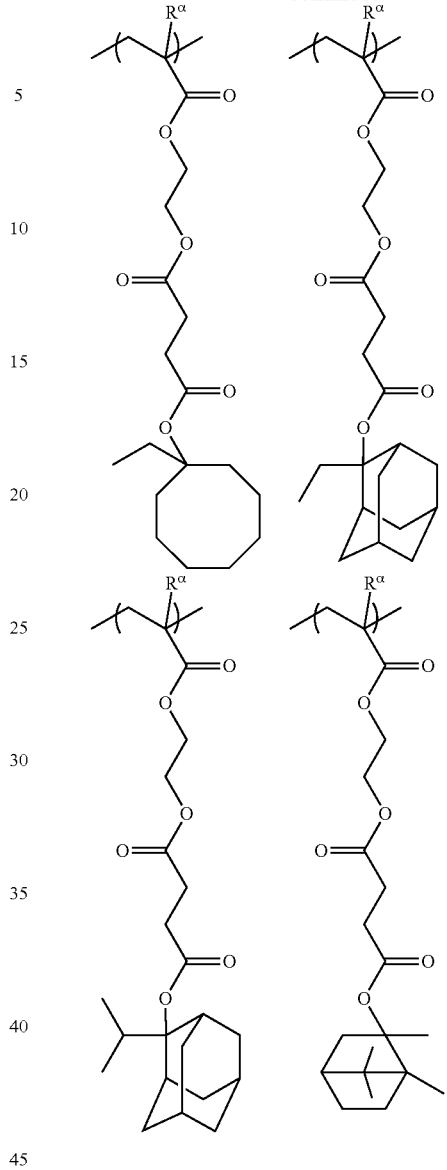

As the structural unit (a0) contained in the component (A1), 1 type of structural unit may be used, or 2 or more types may be used.

In the component (A1), the amount of the structural unit (a0) based on the combined total of all structural units constituting the component (A1) is preferably 10 to 50 mol %, more preferably 10 to 40 mol %, and still more preferably 10 to 35 mol %.

When the amount of the structural unit (a0) is at least as large as the lower limit of the above-mentioned range, various lithography properties such as sensitivity, resolution and LWR are improved. On the other hand, when the amount of the structural unit (a0) is no more than the upper limit of the above-mentioned range, a good balance can be reliably achieved with the other structural units.

(Other Structural Units)

The component (A1) may be further include other structural unit, as well as the structural unit (a0).

As the other structural unit, any other structural unit which cannot be classified as the structural unit (a0) may be used without any particular limitation, and any of the multitude of conventional structural units used within resist resins for ArF excimer lasers or KrF excimer lasers (and particularly for ArF excimer lasers) may be used. For example, any of the structural units (a1) to (a4) and (a6) shown below may be used.

Structural Unit (a1):

In addition to the structural unit (a0), the component (A1) may include a structural unit (a1) containing an acid decomposable group that exhibits increased polarity by the action of acid (provided that structural units which fall under the definition of the structural unit (a0) is excluded).

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group ($-SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given. The acid dissociable group is the same as described above for the "acid dissociable group" for $Ra^0$.

The acid dissociable group for the structural unit (a1) is not particularly limited, and any of the groups that have been conventionally proposed as acid dissociable groups for the base resins of chemically amplified resists can be used.

Examples of the acid dissociable group for protecting the carboxy group or hydroxy group as a polar group include the acid dissociable group represented by general formula (a1-r-1) shown below (hereafter, for the sake of convenience, sometimes referred to as "acetal-type acid dissociable group").

[Chemical Formula 8]

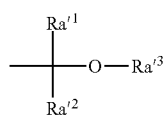

(a1-r-1)

In the formula, $Ra'^1$ and $Ra'^2$ represents a hydrogen atom or an alkyl group; and $Ra'^3$ represents a hydrocarbon group, provided that $Ra'^3$ may be bonded to $Ra'^1$ or $Ra'^2$.

In formula (a1-r-1), as the lower alkyl group for $Ra'^1$ and $Ra'^2$, the same lower alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

The hydrocarbon group for $Ra'^3$ is preferably an alkyl group of 1 to 20 carbon atoms, more preferably an alkyl group of 1 to 10 carbon atoms, and still more preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where $Ra'^3$ represents a cyclic hydrocarbon group, the cyclic hydrocarbon group may be aliphatic or aromatic, and may be polycyclic or monocyclic. As the monocyclic aliphatic hydrocarbon group, a group in which 1 hydrogen atom has been removed from a monocycloalkane is preferable. The monocycloalkane preferably has 3 to 8 carbon atoms, and specific examples thereof include cyclopentane, cyclohexane and cyclooctane. As the polycyclic group, a group in which 1 hydrogen atom has been removed from a polycycloalkane is preferable, and the polycyclic group preferably has 7 to 12 carbon atoms. Examples of the polycycloalkane include adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which 1 hydrogen atom has been removed from the aforementioned aromatic hydrocarbon ring (aryl group); and a group in which 1 hydrogen atom of the aforementioned aryl group has been substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group as a polar group include the acid dissociable group represented by general formula (a1-r-2) shown below (hereafter, with respect to the acid dissociable group represented by the following formula (a1-r-2), the acid dissociable group constituted of alkyl groups is referred to as "tertiary ester-type acid dissociable group").

[Chemical Formula 9]

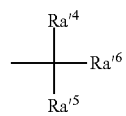

(a1-r-2)

In the formula, $Ra'^4$ to $Ra'^6$ each independently represents a hydrocarbon group, provided that $Ra'^5$ and $Ra'^6$ may be mutually bonded to form a ring.

As the hydrocarbon group for $Ra'^4$ to $Ra'^6$, the same hydrocarbon groups as those described above for $Ra'^3$ can be mentioned. $Ra'^4$ is preferably an alkyl group having from 1 to 5 carbon atoms. In the case where $Ra'^5$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical Formula 10]

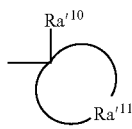

(a1-r2-1)

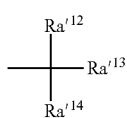

(a1-r2-2)

In the formulae, $Ra'^{10}$ represents an alkyl group of 1 to 10 carbon atoms; $Ra'^{11}$ is a group which forms an aliphatic cyclic group together with a carbon atom having $Ra'^{10}$ bonded thereto; $Ra'^{12}$ to $Ra'^{14}$ each independently represents a hydrocarbon group.

In the formula (a1-r2-1), as the alkyl group of 1 to 10 carbon atoms for $Ra'^{10}$ the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the aliphatic monocyclic group or aliphatic polycyclic group for $Ra'^3$ in the formula (a1-r-1) are preferable.

In the formula (a1-r2-2), it is preferable that $Ra'^{12}$ and $Ra'^{14}$ each independently represents an alkyl group or 1 to 10 carbon atoms, and it is more preferable that the alkyl group is the same group as the described above for the linear or branched alkyl group for $Ra'^3$ in the formula (a1-r-1), it is still more preferable that the alkyl group is a linear alkyl group of 1 to 5 carbon atoms, and it is particularly preferable that the alkyl group is a methyl group or an ethyl group.

In the formula (a1-r2-2), it is preferable that $Ra'^{13}$ is the same group as described above for the linear or branched alkyl group or monocyclic or polycyclic alicyclic hydrocarbon group for $Ra'^3$ in the formula (a1-r-1). Among these, the same monocyclic or polycyclic alicyclic hydrocarbon group as those describe above for $Ra'^3$ is more preferable.

Specific examples of the group represented by the aforementioned formula (a1-r2-1) are shown below. In the formulae shown below, "*" represents a valence bond.

[Chemical Formula 11]

(r-pr-m1)

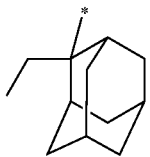

(r-pr-m2)

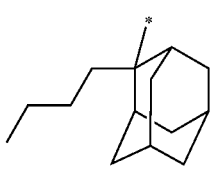

(r-pr-m3)

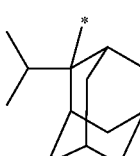

(r-pr-m4)

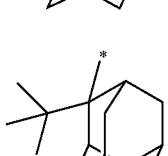

(r-pr-m5)

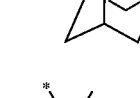

(r-pr-m6)

(r-pr-m7)

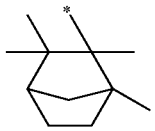

(r-pr-m8)

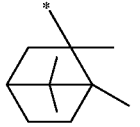

(r-pr-m9)

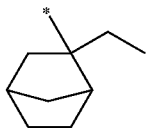

(r-pr-m10)

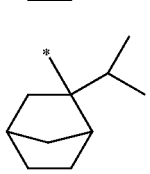

(r-pr-m11)

-continued
(r-pr-m12)
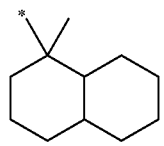
(r-pr-m13)
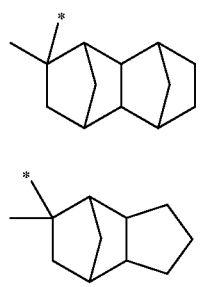
(r-pr-m14)
(r-pr-m15)
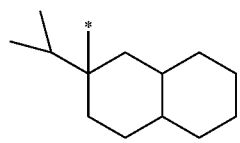
(r-pr-m16)
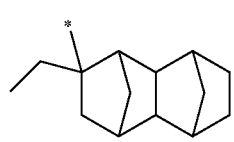
(r-pr-m17)
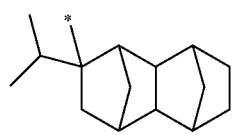
(r-pr-s1)
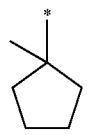
(r-pr-s2)
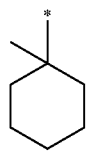
(r-pr-s3)
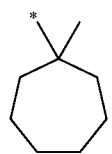
(r-pr-s4)
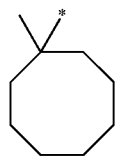
-continued
(r-pr-s5)
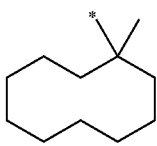
(r-pr-s6)
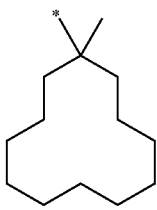
(r-pr-s7)
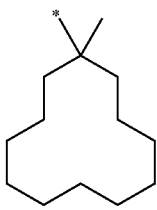
(r-pr-s8)
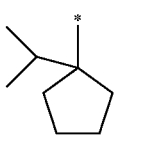
(r-pr-s9)
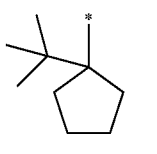
(r-pr-s10)
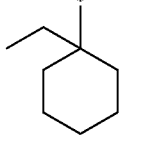
(r-pr-s11)
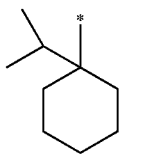
(r-pr-s12)
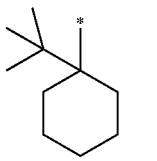
(r-pr-s13)
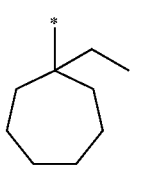

(r-pr-s14)
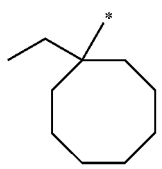
(r-pr-s15)
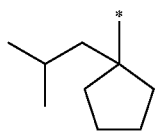
(r-pr-s16)
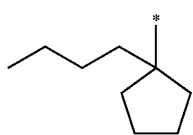
(r-pr-s17)
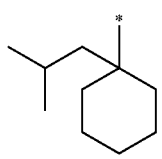
(r-pr-s18)
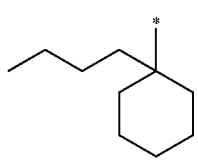
(r-pr-s19)
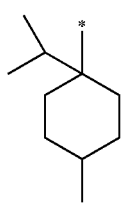
(r-pr-s20)
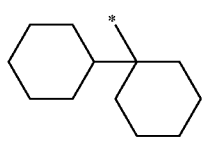
Specific examples of the group represented by the aforementioned formula (a1-r2-2) are shown below.
[Chemical Formula 12]
(r-pr-cm1)
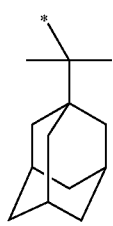
(r-pr-cm2)
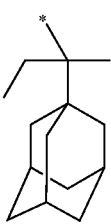
(r-pr-cm3)
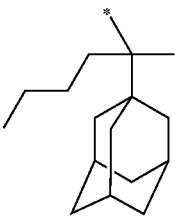
(r-pr-cm4)
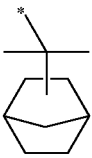
(r-pr-cm5)
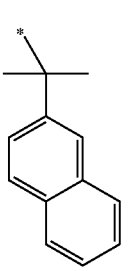
(r-pr-cm6)
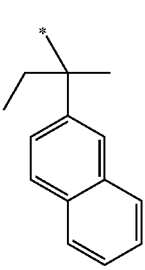
(r-pr-cm7)
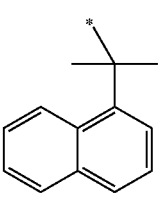
(r-pr-cm8)
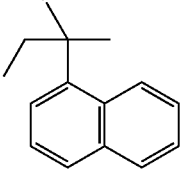

-continued (r-pr-cs1) 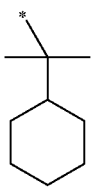

(r-pr-cs2) 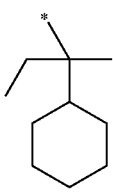

(r-pr-cs3) 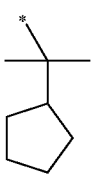

(r-pr-cs4) 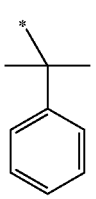

(r-pr-cs5) 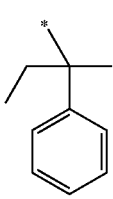

(r-pr-c1) 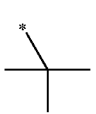

(r-pr-c2) 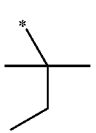

(r-pr-c3) 

(r-pr-c4) 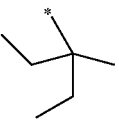

(r-pr-c5) 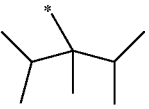

Examples of the acid dissociable group for protecting a hydroxy group as a polar group include the acid dissociable group represented by general formula (a1-r-3) shown below (hereafter, referred to as "tertiary alkyloxycarbonyl-type acid dissociable group").

[Chemical Formula 13]

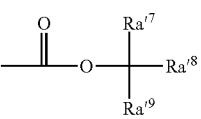

(a1-r-3)

In the formula, $Ra'^7$ to $Ra'^9$ each independently represents an alkyl group.

In the formula (a1-r-3), $Ra'^7$ to $Ra'^9$ is preferably an alkyl group of 1 to 5 carbon atoms, and more preferably an alkyl group of 1 to 3 carbon atoms.

Further, the total number of carbon atoms within the alkyl group is preferably 3 to 7, more preferably 3 to 5, and most preferably 3 or 4.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), a structural unit derived from an acrylate ester which may have the hydrogen atom bonded to the carbon atom on the α-position substituted with a substituent is preferable.

As the structural unit (a1), structural units represented by general formulae (a1-1) to (a1-3) shown below are preferable.

[Chemical Formula 14]

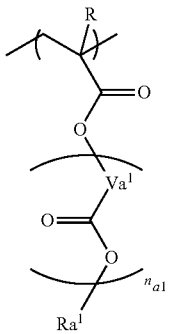
(a1-1)

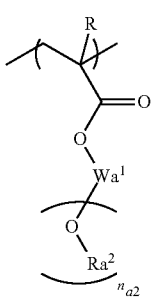
(a1-2)

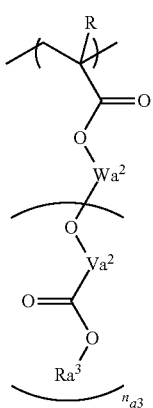
(a1-3)

In the formulae, R represents a hydrogen atom, an alkyl group of 1 to 5 carbon atoms or a halogenated alkyl group of 1 to 5 carbon atoms; $Va^1$ represents a divalent hydrocarbon group which may contain an ether bond, an urethane bond or an amide bond; each $n_{a1}$ represents an integer of 0 to 2; $Ra^1$ represents an acid dissociable group represented by the aforementioned formula (a1-r-1) or (a1-r-2); $Wa^1$ represents a hydrocarbon group having a valency of $n_{a2}+1$; $n_{a2}$ represents an integer of 1 to 3; $Ra^2$ represents an acid dissociable group represented by the aforementioned formula (a1-r-1) or (a1-r-3); $Wa^2$ represents a hydrocarbon group having a valency of $n_{a3}+1$; $n_{a3}$ represents an integer of 1 to 3; $Va^2$ represents a divalent hydrocarbon group which may contain an ether bond, an urethane bond or an amide bond; $Ra^3$ represents an acid dissociable group represented by the aforementioned formula (a1-r-1) or (a1-r-2).

In general formulae (a1-1) to (a1-3), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (a1-1), $Va^1$ represents a divalent hydrocarbon group which may have an ether bond, an urethane bond or an amide bond.

The divalent hydrocarbon group for $Va^1$ may be either an aliphatic hydrocarbon group or an aromatic hydrocarbon group.

The aliphatic hydrocarbon group as the divalent hydrocarbon group for $Va^1$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group as the divalent hydrocarbon group for $Va^1$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

Further, as the group for $Va^1$, a group in which the aforementioned divalent hydrocarbon group has been bonded via an ether bond, urethane bond or amide bond, or a group having such bond within the hydrocarbon chain can be mentioned.

In formula (a1-1), $n_{a1}$ represents an integer of 0 to 2, preferably 0 or 1, and more preferably 0.

In the aforementioned formula (a1-2), the hydrocarbon group for $Wa^1$ having a valency of $n_{a2}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

In the aforementioned formula (a1-3), the hydrocarbon group for $Wa^2$ having a valency of $n_{a3}+1$ may be either an aliphatic hydrocarbon group or an aromatic hydrocarbon group. The aliphatic cyclic group refers to a hydrocarbon group that has no aromaticity, and may be either saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a3}+1$ is preferably divalent, trivalent or tetravalent, and divalent or trivalent is more preferable.

In formula (a1-3), examples of $Va^2$ are the same as defined for the groups for $Va^1$ in formula (a1-1).

As the structural unit (a1-2), a structural unit represented by general formula (a1-2-01) shown below is particularly desirable.

[Chemical Formula 15]

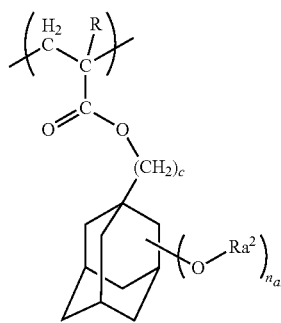

(a1-2-01)

In the formula (a1-2-01), $Ra^2$ represents an acid dissociable group represented by the aforementioned formula (a1-r-1) or (a1-r-3); $n_{a2}$ is an integer of 1 to 3, preferably 1 or 2, and more preferably 1; c is an integer of 0 to 3, preferably 0 or 1, and more preferably 1; R is the same as defined above.

Specific examples of structural units represented by general formulae (a1-1) and (a1-2) are shown below. In the formulae shown below, $R^\alpha$ represents a hydrogen atom, a methyl group or a trifluoromethyl group.

[Chemical Formula 16]

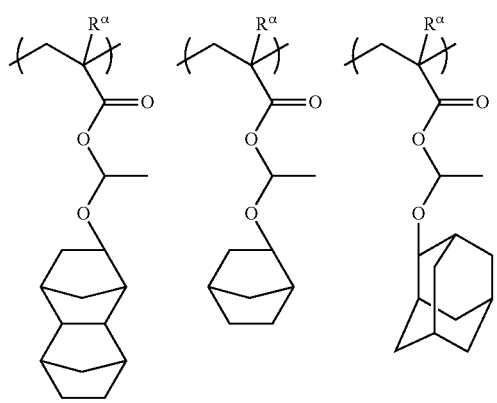

-continued
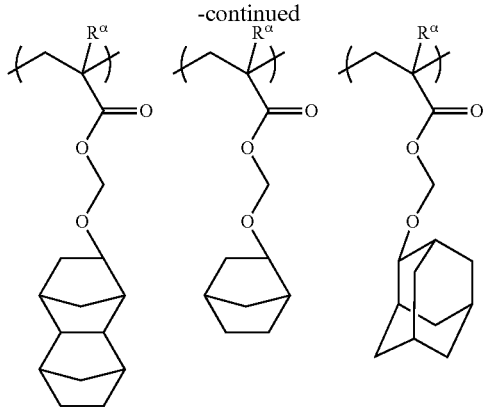
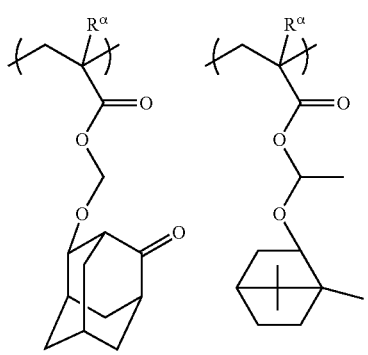
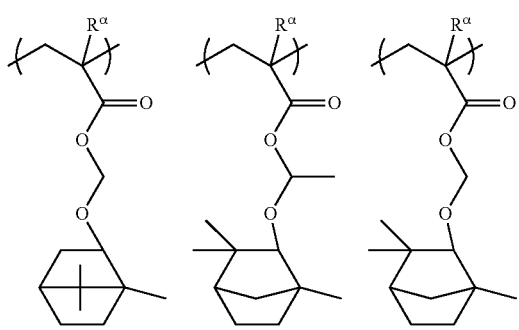
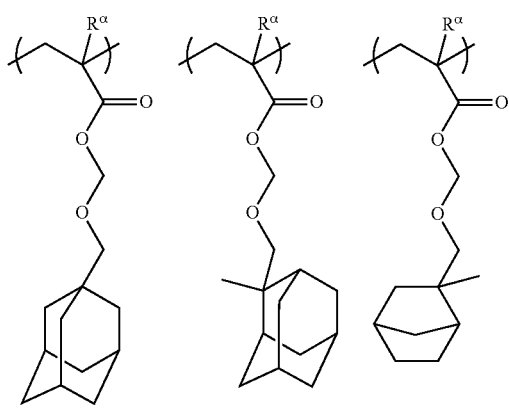
-continued
[Chemical Formula 17]
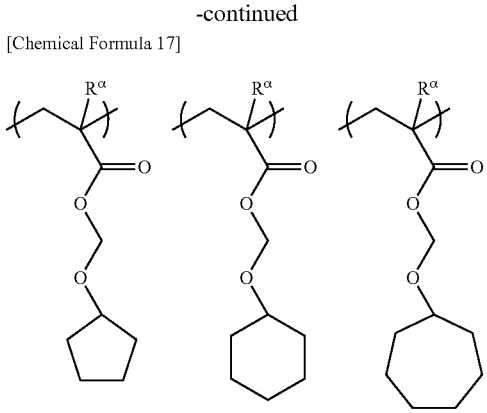
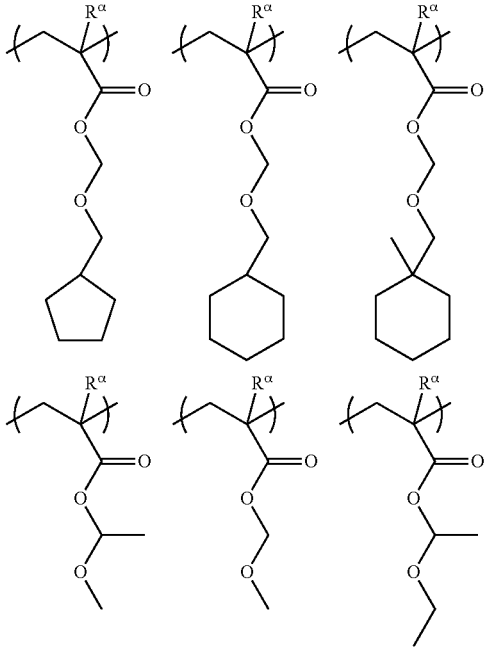
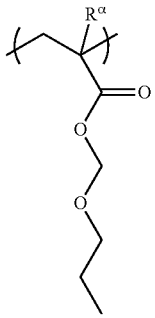
[Chemical Formula 18]
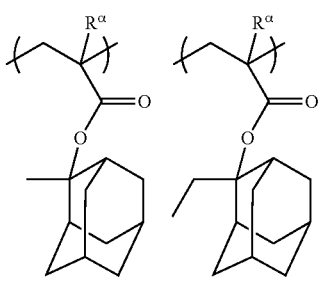

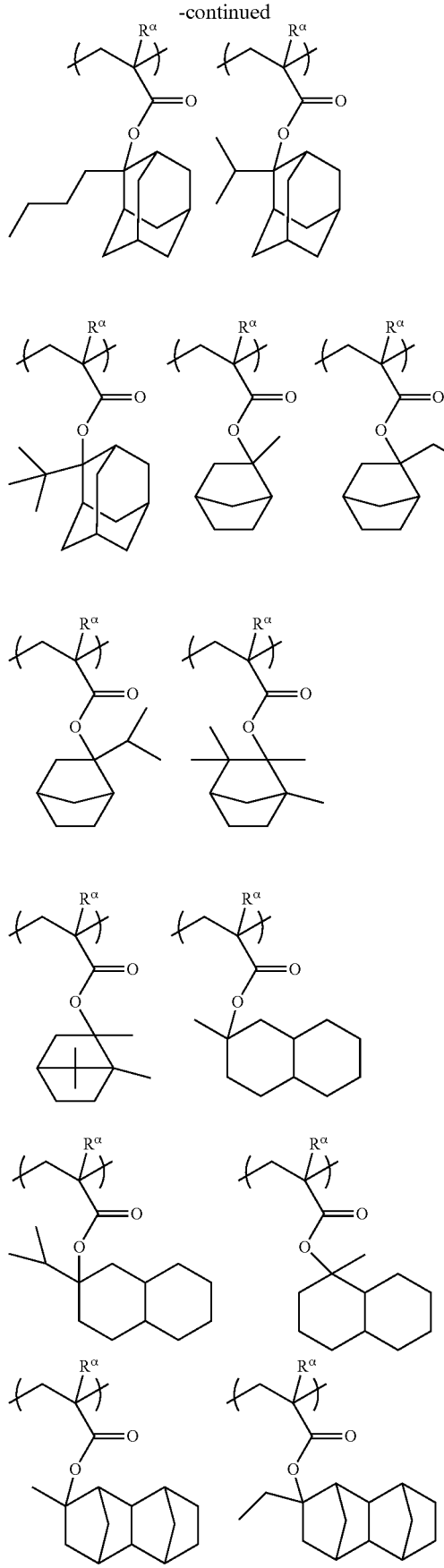
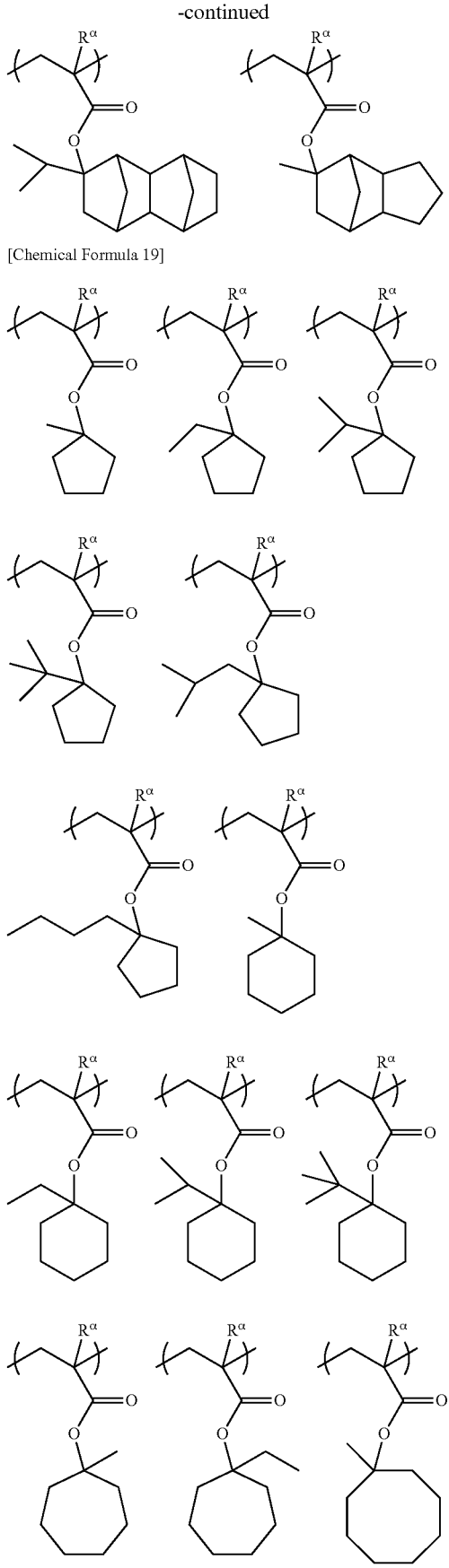
[Chemical Formula 19]

[Chemical Formula 20]
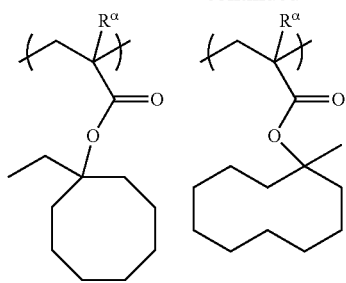
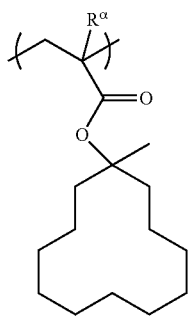
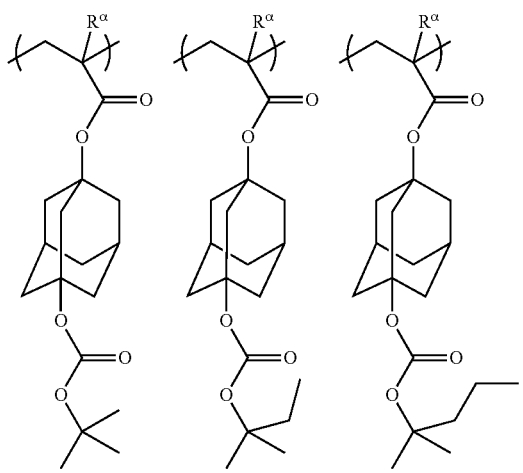
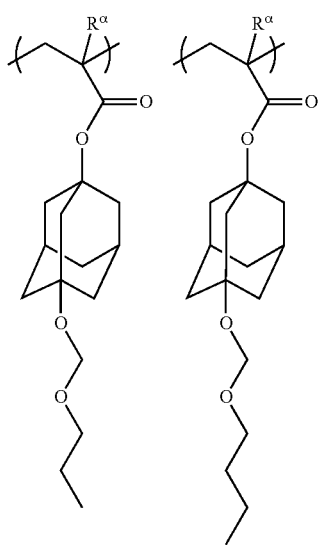
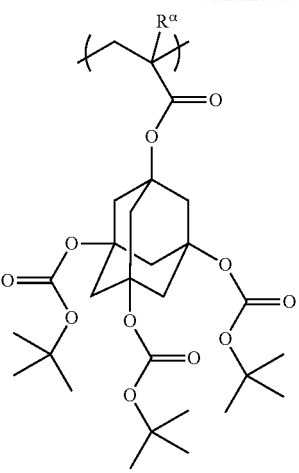
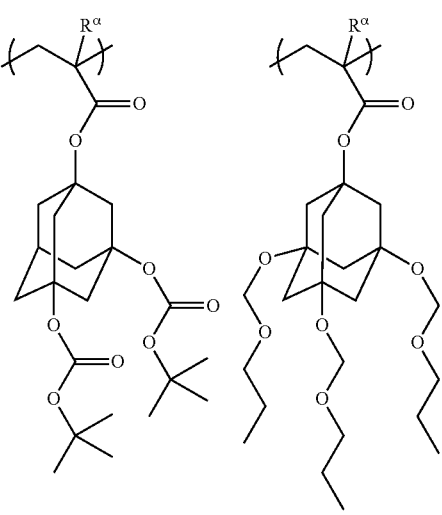
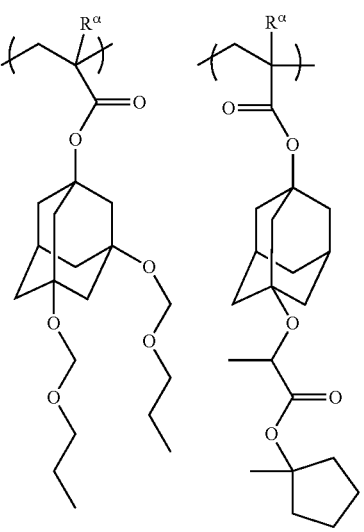

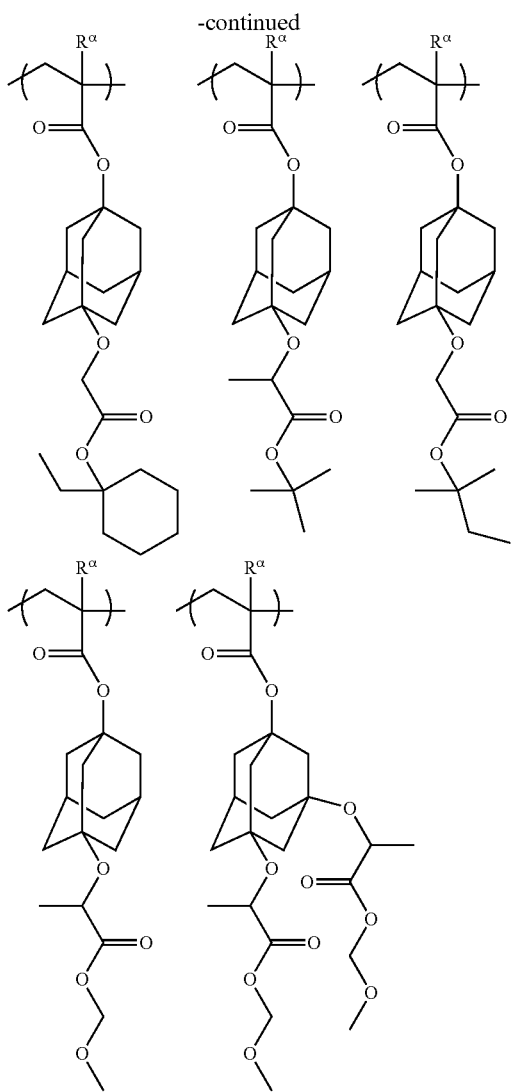

As the structural unit (a1) contained in the component (A1), 1 type of structural unit may be used, or 2 or more types may be used.

When the component (A1) includes the structural unit (a1), the amount of the structural unit (a1) based on the combined total of all structural units constituting the component (A1) is preferably 70 mol % or less, more preferably 60 mol % or less, and still more preferably 50 mol % or less. The lower limit is preferably 10 mol % or more.

When the amount of the structural unit (a1) is no more than the upper limit of the above-mentioned range, a good balance can be achieved with the other structural units, and a resist pattern with an excellent shape may be more reliably obtained. On the other hand, when the amount of the structural unit (a1) is at least as large as the lower limit of the above-mentioned range, various lithography properties such as sensitivity, resolution and LWR may be improved.

Structural Unit (a2):

In the resist composition of the present embodiment, it is preferable that the component (A1) further includes, in addition to the structural unit (a0), a structural unit (a2) containing a lactone-containing cyclic group, an —$SO_2$— containing cyclic group or a carbonate-containing cyclic group.

When the component (A1) is used for forming a resist film, the lactone-containing cyclic group, the —$SO_2$— containing cyclic group or the carbonate-containing cyclic group within the structural unit (a2) is effective in improving the adhesion between the resist film and the substrate.

The aforementioned structural unit (a0) or (a1) which contains a lactone-containing cyclic group, a —$SO_2$— containing cyclic group or a carbonate-containing cyclic group falls under the definition of the structural unit (a2); however, such a structural unit is regarded as a structural unit (a0) or (a1), and does not fall under the definition of the structural unit (a2).

The term "lactone-containing cyclic group" refers to a cyclic group including a ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

As the lactone-containing cyclic group, there is no particular limitation, and an arbitrary group may be used.

Specific examples include groups represented by general formulae (a2-r-1) to (a2-r-7) shown below.

[Chemical Formula 21]

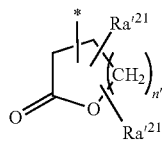

(a2-r-1)

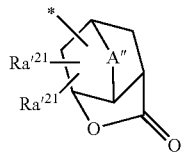

(a2-r-2)

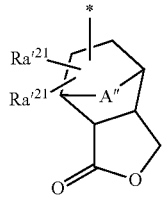

(a2-r-3)

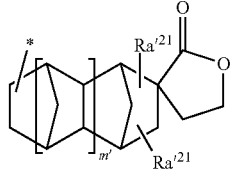

(a2-r-4)

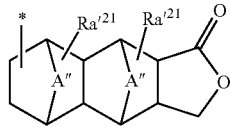

(a2-r-5)

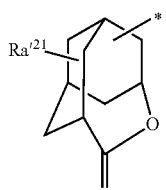
(a2-r-6)

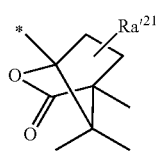
(a2-r-7)

In the formulae, each Ra'$^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; n' represents an integer of 0 to 2; and m' represents 0 or 1.

In formulae (a2-r-1) to (a2-r-7), the alkyl group for Ra'$^{21}$ is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

The alkoxy group for Ra'$^{21}$ is preferably an alkoxy group of 1 to 6 carbon atoms.

Further, the alkoxy group is preferably a linear or branched alkoxy group. Specific examples of the alkoxy groups include the aforementioned alkyl groups for Ra'$^{21}$ having an oxygen atom (—O—) bonded thereto.

As examples of the halogen atom for Ra'$^{21}$, a fluorine atom, chlorine atom, bromine atom and iodine atom can be given. Among these, a fluorine atom is preferable.

Examples of the halogenated alkyl group for Ra'$^{21}$ include groups in which part or all of the hydrogen atoms within the aforementioned alkyl group for Ra'$^{21}$ has been substituted with the aforementioned halogen atoms. As the halogenated alkyl group, a fluorinated alkyl group is preferable, and a perfluoroalkyl group is particularly desirable.

With respect to —COOR" and —OC(=O)R" for Ra'$^{21}$, R" represents a hydrogen atom, an alkyl group, a lactone-containing cyclic group, a carbonate-containing cyclic group or an —SO$_2$— containing cyclic group.

The alkyl group for R" may be linear, branched or cyclic, and preferably has 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. Specific examples include groups in which one or more hydrogen atoms have been removed from a monocycloalkane or a polycycloalkane such as a bicycloalkane, tricycloalkane or tetracycloalkane which may or may not be substituted with a fluorine atom or a fluorinated alkyl group. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Examples of the lactone-containing cyclic group for R" include groups represented by the aforementioned general formulae (a2-r-1) to (a2-r-7).

The carbonate-containing cyclic group for R" is the same as defined for the carbonate-containing cyclic group described later. Specific examples of the carbonate-containing cyclic group include groups represented by general formulae (ax3-r-1) to (ax3-r-3).

The —SO$_2$— containing cyclic group for R" is the same as defined for the —SO$_2$-containing cyclic group described later. Specific examples of the —SO$_2$— containing cyclic group include groups represented by general formulae (a5-r-1) to (a5-r-4).

The hydroxyalkyl group for Ra'$^{21}$ preferably has 1 to 6 carbon atoms, and specific examples thereof include the alkyl groups for Ra'$^{21}$ in which at least one hydrogen atom has been substituted with a hydroxy group.

In general formulae (a2-r-2), (a2-r-3) and (a2-r-5) above, A" represents an oxygen atom (—O—), a sulfur atom (—S—) or an alkylene group of 1 to 5 carbon atoms which may contain an oxygen atom or a sulfur atom. As the alkylene group of 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group of 1 to 5 carbon atoms or —O— is preferable, more preferably an alkylene group of 1 to 5 carbon atoms, and most preferably a methylene group.

Specific examples of the groups represented by the aforementioned general formulae (a2-r-1) to (a2-r-7) are shown below.

[Chemical Formula 22]

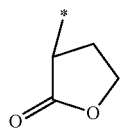
(r-lc-1-1)

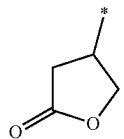
(r-lc-1-2)

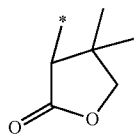 (r-lc-1-3)
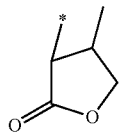 (r-lc-1-4)
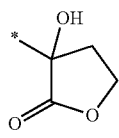 (r-lc-1-5)
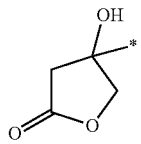 (r-lc-1-6)
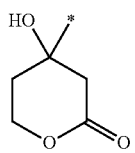 (r-lc-1-7)
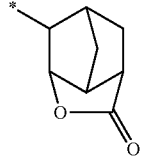 (r-lc-2-1)
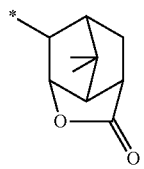 (r-lc-2-2)
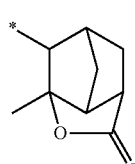 (r-lc-2-3)
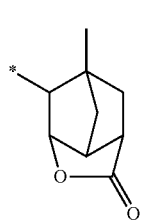 (r-lc-2-4)
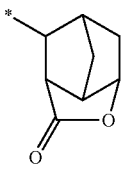 (r-lc-2-5)
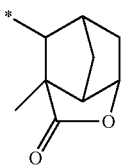 (r-lc-2-6)
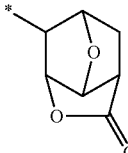 (r-lc-2-7)
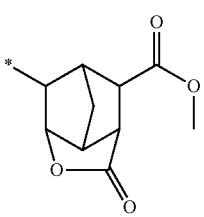 (r-lc-2-8)
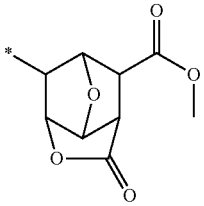 (r-lc-2-9)
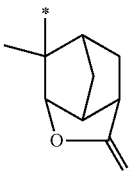 (r-lc-2-10)
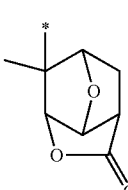 (r-lc-2-11)
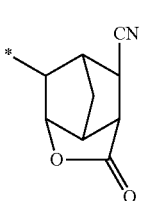 (r-lc-2-12)

-continued
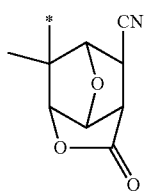 (r-lc-2-13)
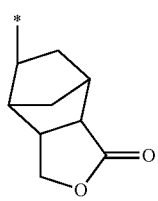 (r-lc-3-1)
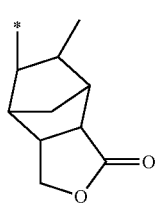 (r-lc-3-2)
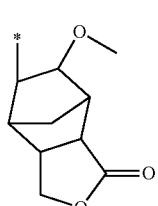 (r-lc-3-3)
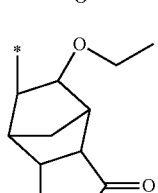 (r-lc-3-4)
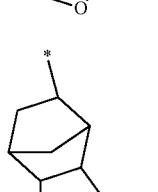 (r-lc-3-5)
[Chemical Formula 23]
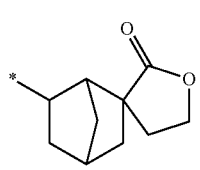 (r-lc-4-1)
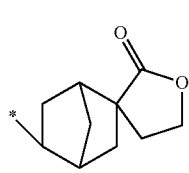 (r-lc-4-2)
-continued
 (r-lc-4-3)
 (r-lc-4-4)
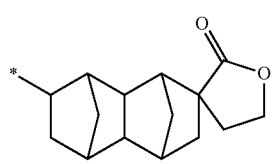 (r-lc-4-5)
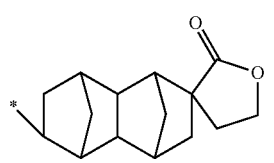 (r-lc-4-6)
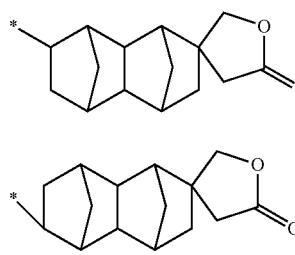 (r-lc-4-7)
(r-lc-4-8)
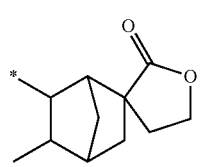 (r-lc-4-9)
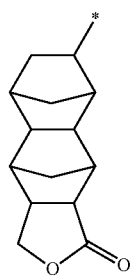 (r-lc-5-1)
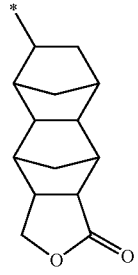 (r-lc-5-2)

(r-lc-5-3)

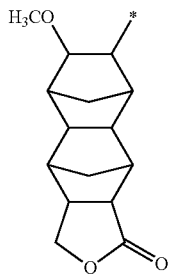

(r-lc-5-4)

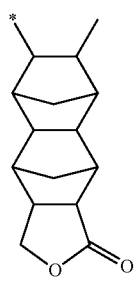

(r-lc-6-1)

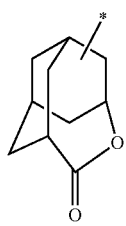

(r-lc-7-1)

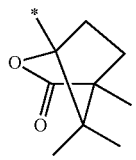

An "—SO$_2$— containing cyclic group" refers to a cyclic group having a ring containing —SO$_2$— within the ring structure thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$— containing cyclic group may be either a monocyclic group or a polycyclic group.

As the —SO$_2$— containing cyclic group, a cyclic group containing —O—SO$_2$— within the ring skeleton thereof, i.e., a cyclic group containing a sultone ring in which —O—S— within the —O—SO$_2$— group forms part of the ring skeleton thereof is particularly desirable. More specific examples of the —SO$_2$— containing cyclic group include groups represented by general formulae (a5-r-1) to (a5-r-4) shown below.

[Chemical Formula 24]

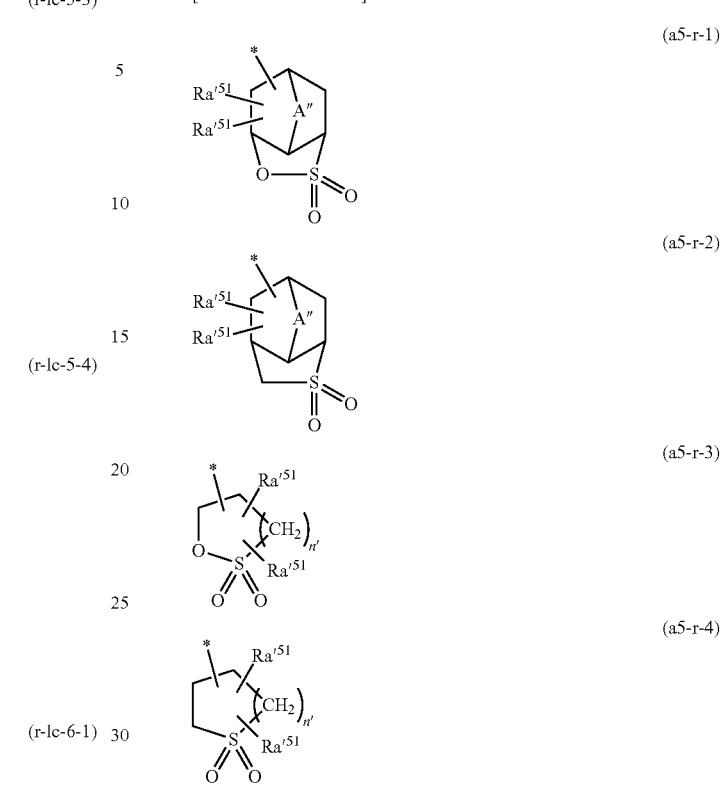

(a5-r-1)

(a5-r-2)

(a5-r-3)

(a5-r-4)

In the formulae, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; and n' represents an integer of 0 to 2.

In general formulae (a5-r-1) and (a5-r-2), A" is the same as defined for A" in general formulae (a2-r-2), (a2-r-3) and (a2-r-5). The alkyl group, alkoxy group, halogen atom, halogenated alkyl group, —COOR", —OC(=O)R" and hydroxyalkyl group for $Ra'^{51}$ are the same as defined for $Ra'^{21}$ in the aforementioned general formulae (a2-r-1) to (a2-r-7).

Specific examples of the groups represented by the aforementioned general formulae (a5-r-1) to (a5-r-4) are shown below. In the formulae shown below, "Ac" represents an acetyl group.

[Chemical Formula 25]

(r-sl-1-1)

(r-sl-1-2)
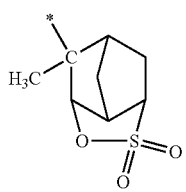
(r-sl-1-3)
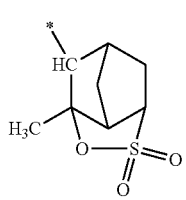
(r-sl-1-4)
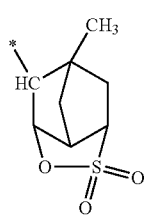
(r-sl-1-5)
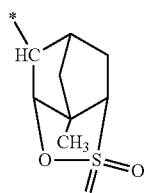
(r-sl-1-6)
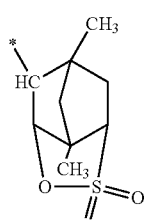
(r-sl-1-7)
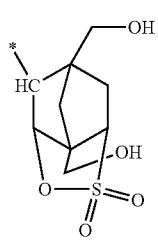
(r-sl-1-8)
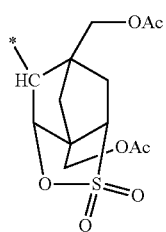
(r-sl-1-9)
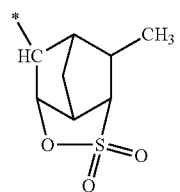
(r-sl-1-10)
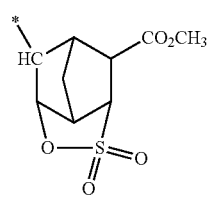
(r-sl-1-11)
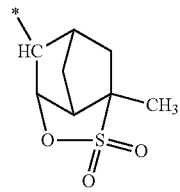
(r-sl-1-12)
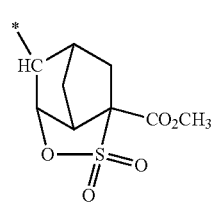
(r-sl-1-13)
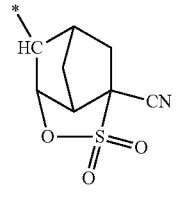
(r-sl-1-14)
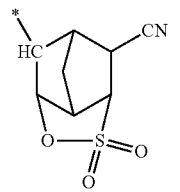
(r-sl-1-15)
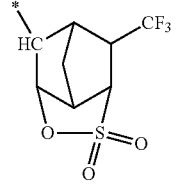
(r-sl-1-16)
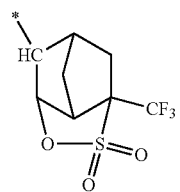

(r-sl-1-17)
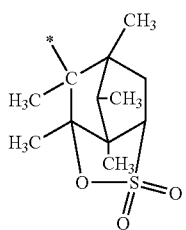
(r-sl-1-18)
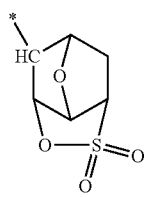
(r-sl-1-19)
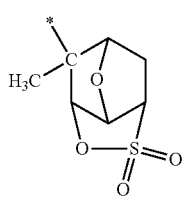
(r-sl-1-20)
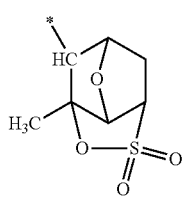
(r-sl-1-21)
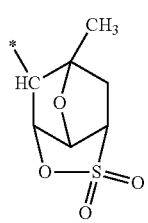
[Chemical Formula 26]
(r-sl-1-22)
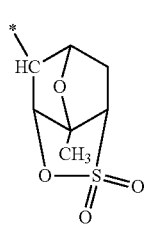
(r-sl-1-23)
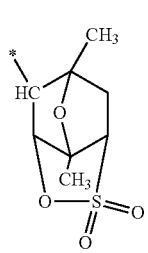
(r-sl-1-24)
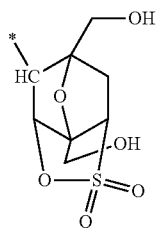
(r-sl-1-25)
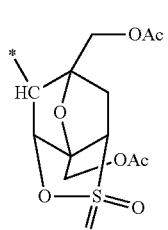
(r-sl-1-26)
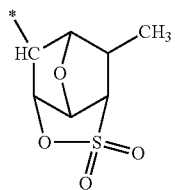
(r-sl-1-27)
(r-sl-1-28)
(r-sl-1-29)
(r-sl-1-30)

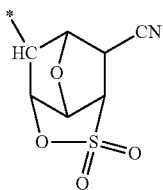
(r-sl-1-31)

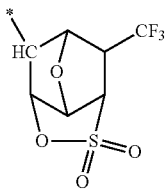
(r-sl-1-32)

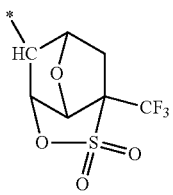
(r-sl-1-33)

[Chemical Formula 27]

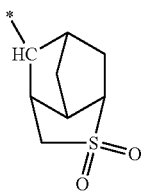
(r-sl-2-1)

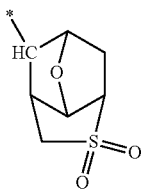
(r-sl-2-2)

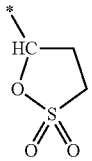
(r-sl-3-1)

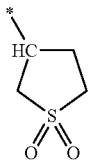
(r-sl-4-1)

As the —SO$_2$— containing cyclic group, a group represented by the aforementioned general formula (a5-r-1) is preferable, at least one member selected from the group consisting of groups represented by the aforementioned chemical formulas (r-sl-1-1), (r-sl-1-18), (r-sl-3-1) and (r-sl-4-1) is more preferable, and a group represented by chemical formula (r-sl-1-1) is most preferable.

The term "carbonate-containing cyclic group" refers to a cyclic group including a ring containing a —O—C(=O)—O— structure (carbonate ring). The term "carbonate ring" refers to a single ring containing a —O—C(=O)—O— structure, and this ring is counted as the first ring. A carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group is not particularly limited, and an arbitrary group may be used. Specific examples include groups represented by general formulae (ax3-r-1) to (ax3-r-3) shown below.

[Chemical Formula 28]

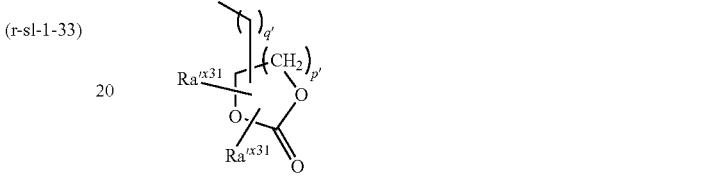
(ax3-r-1)

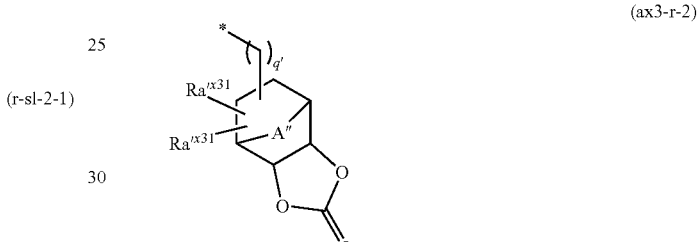
(ax3-r-2)

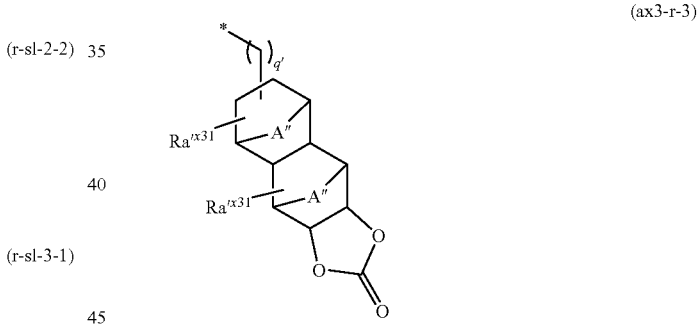
(ax3-r-3)

In the formulae, each Ra$'^{x31}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom, an alkyl group, a lactone-containing cyclic group, a carbonate-containing cyclic group or an —SO$_2$— containing cyclic group; A" represents an oxygen atom, a sulfur atom or an alkylene group of 1 to 5 carbon atoms which may contain an oxygen atom or a sulfur atom; p' represents an integer of 0 to 3; and q' represents 0 or 1.

In general formulae (ax3-r-1) to (ax3-r-3), A" is the same as defined for A" in general formula (a2-r-1).

Examples of the alkyl group, alkoxy group, halogen atom, halogenated alkyl group, —COOR", —OC(=O)R" and hydroxyalkyl group for Ra$'^{x31}$ include the same groups as those described above in the explanation of Ra$'^{21}$ in the general formulas (a2-r-1) to (a2-r-7).

Specific examples of the groups represented by the aforementioned general formulae (ax3-r-1) to (ax3-r-3) are shown below.

[Chemical Formula 29]
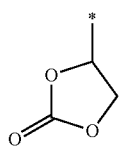 (r-cr-1-1)
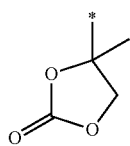 (r-cr-1-2)
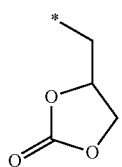 (r-cr-1-3)
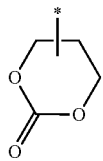 (r-cr-1-4)
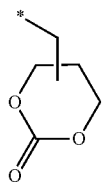 (r-cr-1-5)
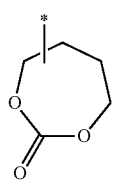 (r-cr-1-6)
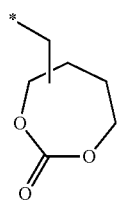 (r-cr-1-6)
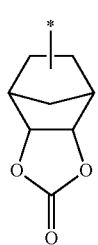 (r-cr-2-1)
-continued
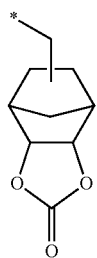 (r-cr-2-2)
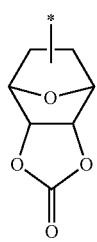 (r-cr-2-3)
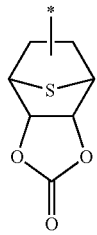 (r-cr-2-4)
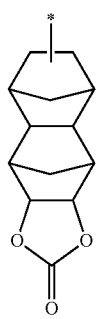 (r-cr-3-1)
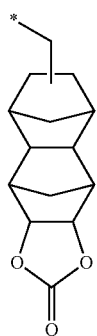 (r-cr-3-2)

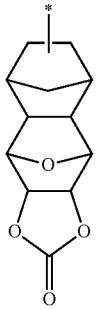

(r-cr-3-3)

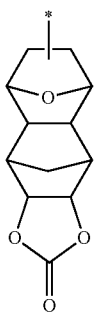

(r-cr-3-4)

(r-cr-3-5)

Among the above examples, a lactone-containing cyclic group or a —$SO_2$— containing cyclic group is preferable, and a lactone-containing cyclic group is more preferable. Specifically, a group represented by the general formula (a2-r-1), (a2-r-2) or (a5-r-1) is more preferable, and a group represented by any one of the chemical formulae (r-lc-1-1) to (r-lc-1-7), (r-lc-2-1) to (r-lc-2-13), (r-sl-1-1) and (r-sl-1-18) is still more preferable.

As the structural unit (a2), a structural unit derived from an acrylate ester which may have the hydrogen atom bonded to the carbon atom on the α-position substituted with a substituent is preferable.

The structural unit (a2) is preferably a structural unit represented by general formula (a2-1) shown below.

[Chemical Formula 30]

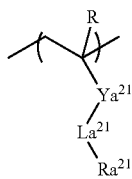

(a2-1)

In the formula, R represents a hydrogen atom, an alkyl group of 1 to 5 carbon atoms, a halogenated alkyl group of 1 to 5 carbon atoms, a hydroxyalkyl group, an alkoxy group; $Ya^{21}$ represents a single bond or a divalent linking group; $La^{21}$ represents —O—, —COO— or —OCO—, provided that, when $La^{21}$ represents —O—, $Ya^{21}$ does not represents —CO—; and $Ra^{21}$ represents a lactone-containing cyclic group, a carbonate-containing cyclic group or an —$SO_2$— containing cyclic group.

The divalent linking group for $Ya^{21}$ is not particularly limited, and preferable examples thereof include a divalent hydrocarbon group which may have a substituent and a divalent linking group containing a hetero atom.

Divalent Hydrocarbon Group which May have a Substituent

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in the aforementioned formula (a1-1) ca be mentioned.

The linear or branched aliphatic hydrocarbon group may or may not have a substituent. Examples of the substituent include a fluorine atom, a fluorinated alkyl group of 1 to 5 carbon atoms, and a carbonyl group.

In the aliphatic hydrocarbon group containing a ring, the cyclic aliphatic hydrocarbon group may or may not have a substituent. Examples of the substituent include an alkyl group, an alkoxy group, a halogen atom, a halogenated alkyl group, a hydroxyl group and a carbonyl group.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

The cyclic aliphatic hydrocarbon group may have part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified above for $Va^1$ in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group of 1 to 5 carbon atoms, and a methyl group, an ethyl group, a propyl group, an n-butyl group or a tert-butyl group is particularly desirable.

As the alkoxy group, the halogen atom and the halogenated alkyl group for the substituent, the same groups as the aforementioned substituent groups for substituting a hydrogen atom within the cyclic aliphatic hydrocarbon group can be used.

Divalent Linking Group Containing a Hetero Atom

With respect to a divalent linking group containing a hetero atom, a hetero atom is an atom other than carbon and hydrogen, and examples thereof include an oxygen atom, a nitrogen atom, a sulfur atom and a halogen atom.

In the case where $Ya^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, a group represented by general formula —$Y^{21}$—O—$Y^{22}$—, —$Y^{21}$—O—, —$Y^{21}$—C(=O)—O—, —C(=O)—O—$Y^{21}$, —[$Y^{21}$—C(=O)—O]$_{m''}$—$Y^{22}$— or —$Y^{21}$—O—C(=O)—$Y^{22}$— [in the formulae, $Y^{21}$ and $Y^{22}$ each independently represents a divalent hydrocarbon group which may have a substituent, and O represents an oxygen atom; and m" represents an integer of 0 to 3.

The divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and most preferably 1 to 5.

In formulae —$Y^{21}$—O—$Y^{22}$—, —$^{21}Y$—O—, —$Y^{21}$—C(=O)—O—, —C(=O)—O—$Y^{21}$, —[$Y^{21}$—C(=O)—O]$_{m''}$—$Y^{22}$— and —$Y^{21}$—O—C(=O)—$Y^{22}$—, $Y^{21}$ and $Y^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m''}$—$Y^{22}$—, m" represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m''}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

$Ya^{21}$ preferably represents an ester bond [—C(=O)—O—], an ether bond (—O—), a linear or branched alkylene group, a combination of these, or a single bond.

In formula (a2-1), $Ra^{21}$ represents the aforementioned lactone-containing cyclic group, —SO$_2$— containing cyclic group or carbonate-containing cyclic group, preferably lactone-containing cyclic group or —SO$_2$— containing cyclic group, and most preferably lactone-containing cyclic group.

As the structural unit (a2) contained in the component (A1), 1 type of structural unit may be used, or 2 or more types may be used.

When the component (A1) contains the structural unit (a2), the amount of the structural unit (a2) based on the combined total of all structural units constituting the component (A1) is preferably 1 to 70 mol %, more preferably 5 to 70 mol %, still more preferably 10 to 65 mol %, and most preferably 10 to 60 mol %.

When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties and pattern shape can be improved.

Structural Unit (a3):

In the resist composition of the present embodiment, it is preferable that the component (A1) further includes, in addition to the structural unit (a0), a structural unit (a3) containing a polar group-containing aliphatic hydrocarbon group (provided that structural units which fall under the definition of the structural unit (a0), the structural unit (a1) or the structural unit (a2) are excluded).

When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 31]

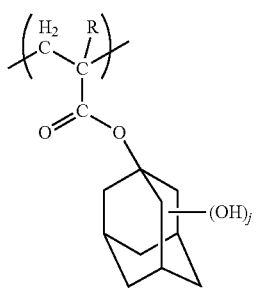 (a3-1)

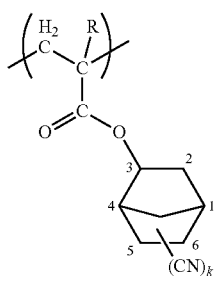 (a3-2)

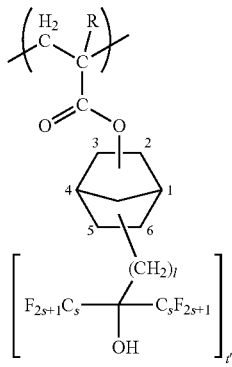 (a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group.

When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 kind of structural unit may be used, or 2 or more kinds of structural units may be used.

When the component (A1) contains the structural unit (a3), the amount of the structural unit (a3) based on the combined total of all structural units constituting the component (A1) is preferably 1 to 40 mol %, more preferably 2 to 30 mol %, still more preferably 5 to 25 mol %, and most preferably 10 to 20 mol %.

When the amount of the structural unit (a3) is at least as large as the lower limit of the above-mentioned preferable range, the resolution is improved in the formation of a resist pattern. On the other hand, when the amount of the structural unit (a3) is no more than the upper limit of the above-mentioned preferable range, a good balance can be reliably achieved with the other structural units.

Structural Unit (a4):

The component (A1) may be further include, in addition to the structural unit (a0), a structural unit (a4) containing an acid non-dissociable, aliphatic cyclic group.

When the component (A1) includes the structural unit (a4), dry etching resistance of the resist pattern to be formed is improved. Further, the hydrophobicity of the component (A) is further improved. Increase in the hydrophobicity contributes to improvement in terms of resolution, shape of the resist pattern and the like, particularly in a solvent developing process.

An "acid non-dissociable, aliphatic cyclic group" in the structural unit (a4) refers to a cyclic group which is not dissociated by the action of the acid (e.g., acid generated from the structural unit (a6) or the component (B) described later) upon exposure, and remains in the structural unit.

As the structural unit (a4), a structural unit which contains a non-acid-dissociable aliphatic cyclic group, and is also derived from an acrylate ester is preferable. As the cyclic group, any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include structural units represented by general formulae (a4-1) to (a4-7) shown below.

[Chemical Formula 32]

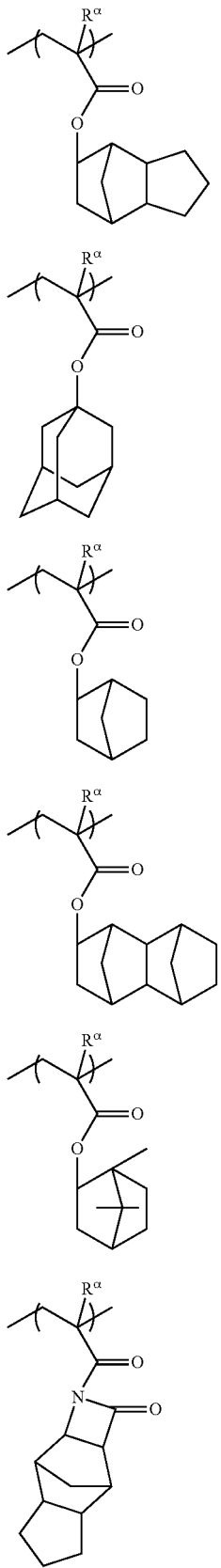

(a4-1)
(a4-2)
(a4-3)
(a4-4)
(a4-5)
(a4-6)

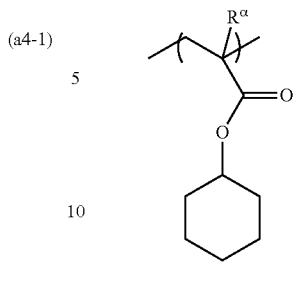

(a4-7)

In the formulae, $R^\alpha$ is the same as defined above.

As the structural unit (a4) contained in the component (A1), 1 type of structural unit may be used, or 2 or more types may be used.

When the component (A1) includes the structural unit (a4), the amount of the structural unit (a4) based on the combined total of all structural units constituting the component (A1) is preferably 1 to 40 mol %, and more preferably 5 to 20 mol %.

When the amount of the structural unit (a4) is at least as large as the lower limit of the above-mentioned preferable range, the effect of using the structural unit (a4) can be satisfactorily achieved. On the other hand, when the amount of the structural unit (a4) is no more than the upper limit of the above-mentioned preferable range, a good balance can be achieved with the other structural units.

(Structural Unit (a6))

The component (A1) may be further include, in addition to the structural unit (a0), a structural unit (a6) which generates acid upon exposure.

The structural unit (a6) is not particularly limited as long as it generates acid upon exposure. For example, a structural unit copolymerizable with the aforementioned structural unit (a0) and in which a structure proposed as an acid generator for a conventional chemically amplified resist has been introduced can be used.

Preferable examples of structural units copolymerizable with structural unit (a0) include a structural unit derived from an acrylate ester which may have the hydrogen atom bonded to the carbon atom on the α-position substituted with a substituent, and a structural unit derived from hydroxystyrene or a hydroxystyrene derivative.

Preferable examples of a compound having a structure proposed as an acid generator for a conventional chemically amplified resist include the component (B) described later.

Examples of the structural unit (a6) include a structural unit (a6c) having an anion group which generates an acid upon exposure on a side chain thereof, and a structural unit (a6c) which has a cation group that is decomposed upon exposure on a side chain thereof.

Structural Unit (a6a)

The structural unit (a6c) is a structural unit having an anion group which generates an acid upon exposure on a side chain thereof.

The anion group which generates acid upon exposure is not particularly limited, and a sulfonic acid anion, an amide anion or a methide anion is preferable. Among these, as the anion group, a group represented by any one of general formulae (a6a-r-1), (a6a-r-2) or (a6a-r-3) shown below is preferable.

[Chemical Formula 33]

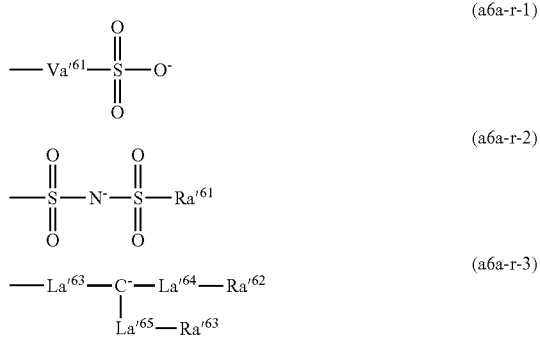

In the formulae, $Va'^{61}$ represents a divalent hydrocarbon group having a fluorine atom; $La'^{63}$ to $La'^{65}$ each independently represents —$SO_2$— or a single bond; $Ra'^{61}$ to $Ra'^{63}$ each independently represents a hydrocarbon group which may have a substituent.

In formula (a6a-r-1), $Va'^{61}$ represents a divalent hydrocarbon group having a fluorine atom. The divalent hydrocarbon group for $Va'^{61}$ may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group has a fluorine atom, and all of the hydrogen atoms of the aliphatic hydrocarbon group may be substituted with fluorine. Further, in addition to fluorine, the aliphatic hydrocarbon group may be substituted with an oxo group (=O).

As examples of the hydrocarbon group containing a ring in the structure thereof, a cyclic aliphatic hydrocarbon group containing a hetero atom in the ring structure thereof and may have a substituent (a group in which two hydrogen atoms have been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic group is interposed within the aforementioned linear or branched aliphatic hydrocarbon group, can be given. The linear or branched aliphatic hydrocarbon group is the same as defined for the aforementioned linear aliphatic hydrocarbon group or the aforementioned branched aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group has a fluorine atom, and all of the hydrogen atoms of the cyclic aliphatic hydrocarbon group may be substituted with fluorine. Further, in addition to fluorine, the cyclic aliphatic hydrocarbon group may be substituted with an alkyl group, an alkoxy group, a hydroxy group, an oxo group (=O) or the like.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The aromatic hydrocarbon group for the divalent hydrocarbon group represented by $Va'^{61}$ is a hydrocarbon group having at least one aromatic ring.

The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. Here, the number of carbon atoms within a substituent(s) is not included in the number of carbon atoms of the aromatic hydrocarbon group.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group). The alkylene group which is bonded to the aforementioned aryl group or heteroaryl group preferably has 1 to 4 carbon atoms, more preferably 1 or 2 carbon atoms, and most preferably 1 carbon atom.

The aromatic hydrocarbon group has a fluorine atom, and all of the hydrogen atoms of the aromatic hydrocarbon group may be substituted with fluorine. Further, in addition to fluorine, the cyclic aliphatic hydrocarbon group may be substituted with an alkyl group, an alkoxy group, a hydroxy group, an oxo group (=O) or the like. The alkyl group and the alkoxy group as the substituent are the same as defined for the alkyl group and the alkoxy group as the substituent for the cyclic aliphatic hydrocarbon group.

Among the anion groups represented by formula (a6a-r-1), a group represented by general formula (a6a-r-11) shown below is preferable.

[Chemical Formula 34]

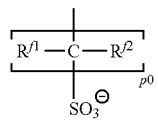

(a6a-1-11)

In the formula, $R^{f1}$ and $R^{f2}$ each independently represents a hydrogen atom, an alkyl group, a fluorine atom or a fluorinated alkyl group, provided that at least one of $R^{f1}$ and $R^{f2}$ represents a fluorine atom or a fluorinated alkyl group; and p0 represents an integer of 1 to 8.

In formula (a6a-r-11), each of $R^{f1}$ and $R^{f2}$ independently represents a hydrogen atom, an alkyl group, a fluorine atom or a fluorinated alkyl group, provided that at least one of $R^{f1}$ and $R^{f2}$ represents a fluorine atom or a fluorinated alkyl group.

The alkyl group for $R^{f1}$ and $R^{f2}$ is preferably an alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The fluorinated alkyl group for $R^{f1}$ and $R^{f2}$ is preferably a group in which part or all of the hydrogen atoms within the aforementioned alkyl group for $R^{f1}$ and $R^{f2}$ have been substituted with a fluorine atom.

As $R^{f1}$ and $R^{f2}$, a fluorine atom or a fluorinated alkyl group is preferable.

In formula (a6a-r-11), p0 represents an integer of 1 to 8, preferably an integer of 1 to 4, and more preferably 1 or 2.

In formula (a6a-r-2), as the hydrocarbon group for $Ra^{\prime 61}$, an alkyl group, a monovalent alicyclic hydrocarbon group, an aryl group and an aralkyl group can be mentioned.

The alkyl group for $Ra^{\prime 61}$ preferably has 1 to 8 carbon atoms, more preferably 1 to 6 carbon atoms, and still more preferably 1 to 4 carbon atoms. The alkyl group may be linear or branched. Specific examples of preferable alkyl groups include a methyl group, an ethyl group, a propyl group, a butyl group, a hexyl group and an octyl group.

The monovalent alicyclic hydrocarbon group for $Ra^{\prime 61}$ preferably has 3 to 20 carbon atoms, and more preferably 3 to 12 carbon atoms. The monovalent alicyclic hydrocarbon group may be polycyclic or monocyclic. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic alicyclic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aryl group for $Ra^{\prime 61}$ preferably has 6 to 18 carbon atoms, and more preferably 6 to 10 carbon atoms. Specifically, a phenyl group is particularly desirable.

As a preferable examples of the aralkyl group for $Ra^{\prime 61}$, a group in which an alkylene group of 1 to 8 carbon atoms has been bonded to the aforementioned "aryl group for $Ra^{\prime 61}$" can be mentioned. An aralkyl group in which an alkylene group of 1 to 6 carbon atoms has been bonded to the aforementioned "aryl group for $Ra^{\prime 61}$" is more preferable, and an aralkyl group in which an alkylene group of 1 to 4 carbon atoms has been bonded to the aforementioned "aryl group for $Ra^{\prime 61}$" is most preferable.

The hydrocarbon group for $Ra^{\prime 61}$ may have a substituent, preferably has part or all of the hydrogen atoms within the hydrocarbon group substituted with fluorine, and the hydrocarbon group more preferably has 30 to 100% of the hydrogen atoms substituted with fluorine. Among these, a perfluoroalkyl group in which all of the hydrogen atoms within the alkyl group have been substituted with fluorine atoms is particularly desirable. In addition, the hydrocarbon group for $Ra^{\prime 61}$ may have a methylene group (—$CH_2$—) substituted with a divalent group such as —CO— or —$SO_2$—.

In formula (a6a-r-3), $La^{\prime 63}$ to $La^{\prime 65}$ each independently represents —$SO_2$— or a single bond, and $Ra^{\prime 62}$ and $Ra^{\prime 63}$ each independently represents a hydrocarbon group which may have a substituent. The hydrocarbon group for $Ra^{\prime 62}$ and $Ra^{\prime 63}$ is the same as defined for the hydrocarbon group for $Ra^{\prime 61}$ which may have a substituent.

Preferable examples of the structural unit (a6a) include structural units represented by general formulae (a6a-1) to (a6a-8) shown below.

[Chemical Formula 35]

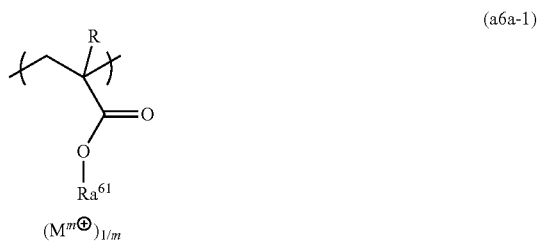

(a6a-1)

(a6a-2)
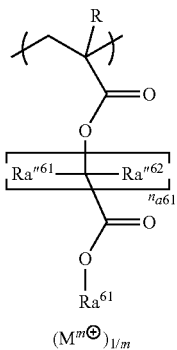

(a6a-3)
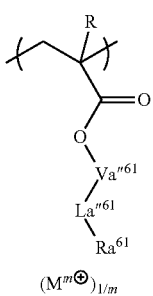

(a6a-4)
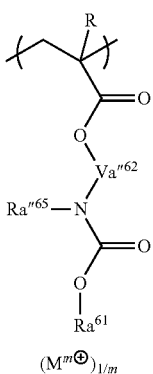

(a6a-5)
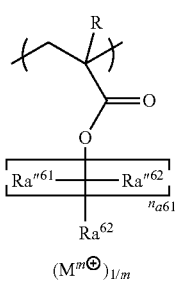

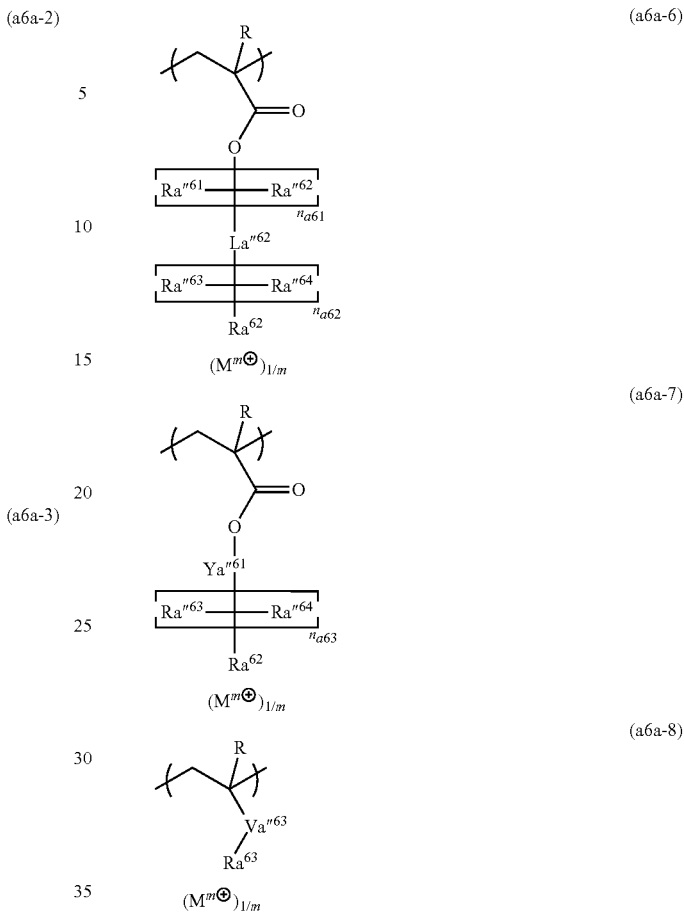

In the formula, R represents a hydrogen atom, an alkyl group of 1 to 5 carbon atoms or a halogenated alkyl group of 1 to 5 carbon atoms; $Ra^{61}$ is a group represented by the aforementioned formula (a6a-r-1); $Ra^{62}$ is a group represented by the aforementioned formula (a6a-r-2) or (a6a-r-3); $Ra^{63}$ is a group represented by the aforementioned formula (a6a-r-3); $Ra''^{61}$ to $Ra''^{64}$ each independently represents a hydrogen atom, a fluorine atom, an alkyl group of 1 to 5 carbon atoms or a fluorinated alkyl group; $n_{a61}$ and $n_{a62}$ each independently represents an integer of 1 to 10; $n_{a63}$ represents an integer of 0 to 10;

$Va''^{61}$ represents a divalent cyclic hydrocarbon group; $La''^{61}$ represents —C(=O)—O—, —O—C(=O)—O— or —O—CH$_2$—C(=O)—O—; $Va''^{62}$ represents a divalent hydrocarbon group; $Ra''^{65}$ represents a hydrogen atom or an alkyl group of 1 to 5 carbon atoms; $La''^{62}$ represents —C(=O)—O—, —O—C(=O)—O— or —NH—C(=O)—O—; $Ya''^{61}$ represents a divalent linking group containing a cyclic hydrocarbon group; $Va''^{63}$ represents a divalent cyclic hydrocarbon group or a single bond; m represents an integer of 1 or more; and each $M^{m+}$ independently represents an organic cation having a valency of m.

In formulae (a6a-1) to (a6a-8), R is the same as defined for R in the aforementioned formula (a1-1).

In formulae (a6a-1) to (a6a-4), each $Ra^{61}$ independently represents a group represented by the aforementioned formula (a6a-r-1). In formulae (a6a-5) to (a6a-7), each $Ra^{62}$ independently represents a group represented by the aforementioned formula (a6a-r-2) or (a6a-r-3). In formula (a6a-8), $Ra^{63}$ represents a group represented by the aforementioned formula (a6a-r-3).

In formulae (a6a-2) and (a6a-5) to (a6a-7), Ra"$^{61}$ to Ra"$^{64}$ each independently represents a hydrogen atom, a fluorine atom, an alkyl group of 1 to 5 carbon atoms or a fluorinated alkyl group. Examples of the fluorinated alkyl group for Ra"$^{61}$ to Ra"$^{64}$ include groups in which part or all of the hydrogen atoms within the alkyl group of 1 to 5 carbon atoms have been substituted with a fluorine atom.

In formulae (a6a-2), (a6a-5) and (a6a-6), each $n_{a61}$ independently represents an integer of 1 to 10, preferably an integer of 1 to 8, more preferably an integer of 1 to 4, and still more preferably 1 or 2.

In formula (a6a-6), $n_{a62}$ represents an integer of 1 to 10, preferably an integer of 1 to 8, more preferably an integer of 1 to 4, and still more preferably 1 or 2.

In formula (a6a-7), $n_{a63}$ represents an integer of 0 to 10, preferably an integer of 0 to 5, more preferably an integer of 0 to 3, and still more preferably 0.

In formula (a6a-3), Va"$^{61}$ represents a divalent cyclic hydrocarbon group, and is the same as defined for the "aliphatic hydrocarbon group containing a ring in the structure thereof" and "aromatic hydrocarbon group" explained above in relation to Va'$^{61}$ in the aforementioned formula (a6a-r-1).

La"$^{61}$ represents —C(=O)—O—, —O—C(=O)—O— or —O—CH$_2$—C(=O)—O—.

In formula (a6a-4), Va"$^{62}$ represents a divalent hydrocarbon group, and is the same as defined for the divalent hydrocarbon group explained above in relation to Va'$^{61}$ in the aforementioned formula (a6a-r-1).

Ra"$^{65}$ represents a hydrogen atom or an alkyl group of 1 to 5 carbon atoms.

In formula (a6a-6), La"$^{62}$ represents —C(=O)—O—, —O—C(=O)—O— or —NH—C(=O)—O—.

In formula (a6a-7), Ya"$^{61}$ represents a divalent cyclic hydrocarbon group, and is the same as defined for the "aliphatic hydrocarbon group containing a ring in the structure thereof", the "aromatic hydrocarbon group" and the "divalent linking group containing a hetero atom" (having an "aliphatic hydrocarbon group containing a ring in the structure thereof" or an "aromatic hydrocarbon group") described later in relation to the divalent linking group for Ya$^{21}$ in the aforementioned general formula (a2-1).

In formula (a6a-8), Va"$^{63}$ represents a divalent cyclic hydrocarbon group or a single bond. The divalent cyclic hydrocarbon group for Va"$^{63}$ is the same as defined for the "aliphatic hydrocarbon group containing a ring in the structure thereof" and "aromatic hydrocarbon group" explained above in relation to Va'$^{61}$ in the aforementioned formula (a6a-r-1).

In formula (a6a-1) to (a6a-8), m represents an integer of 1 or more, and each M$^{m+}$ independently represents an organic cation having a valency of m.

The organic cation for M$^{m+}$ is not particularly limited. As the organic cation, an onium cation having a valency of m is preferable, more preferably a sulfonium cation or an iodonium cation, most preferably an organic cation represented by any one of formulae (ca-1) to (ca-4) described later.

Specific examples of structural unit represented by formula (a6a-1) are shown below. (M$^{m+}$)$_{1/m}$ is the same as defined above.

[Chemical Formula 36]

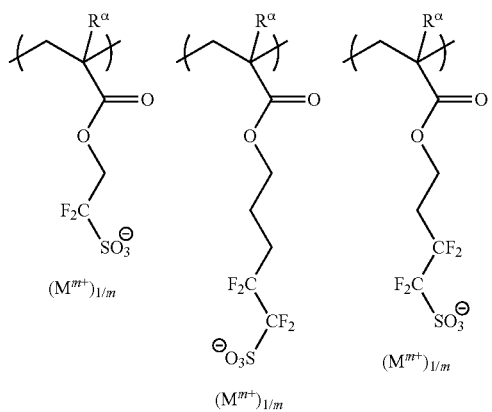

Specific examples of structural unit represented by formula (a6a-2) are shown below.

[Chemical Formula 37]

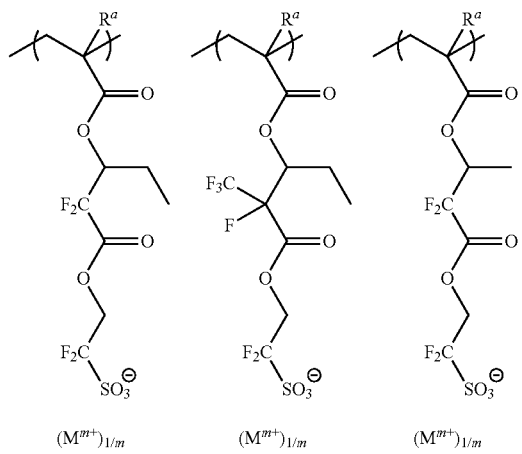

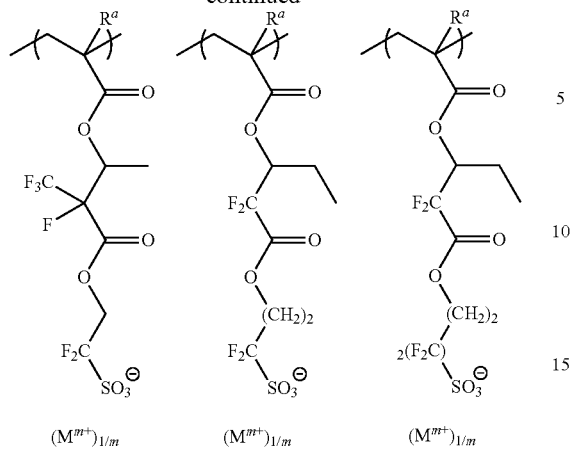
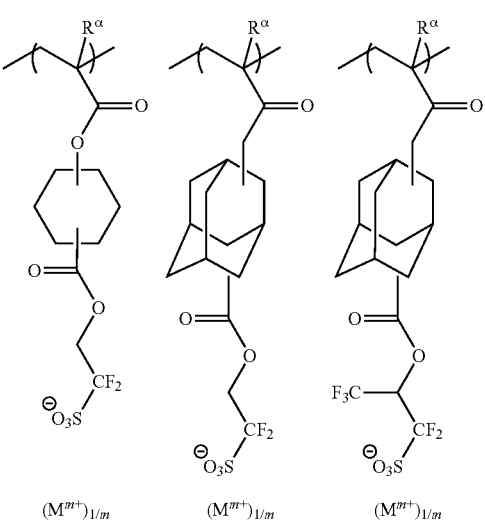
[Chemical Formula 38]
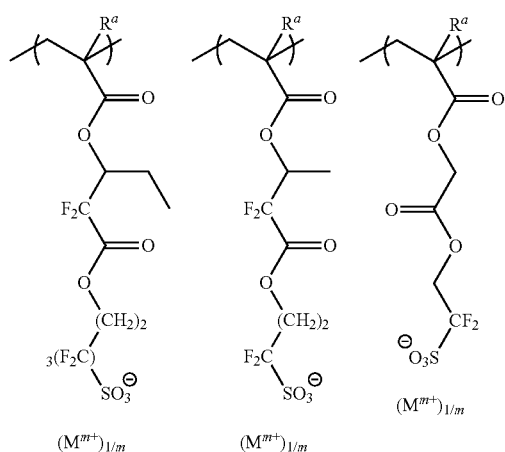
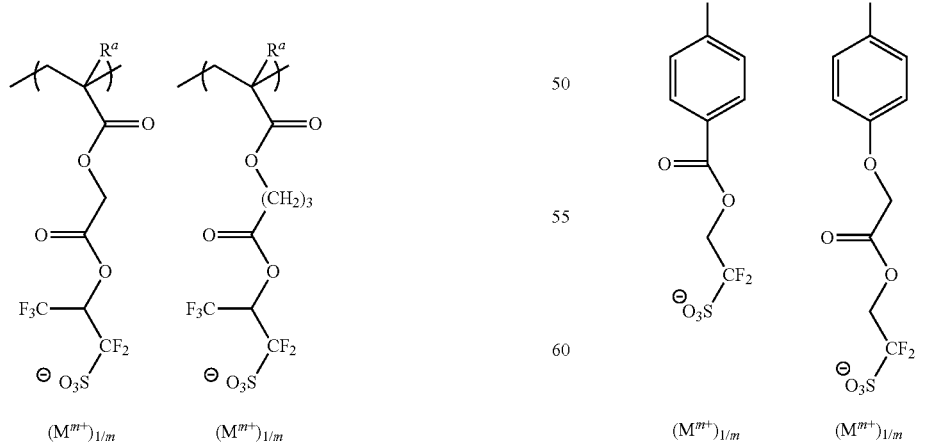
Specific examples of structural unit represented by formula (a6a-3) are shown below.
Specific examples of structural unit represented by formula (a6a-4) are shown below.

[Chemical Formula 39]
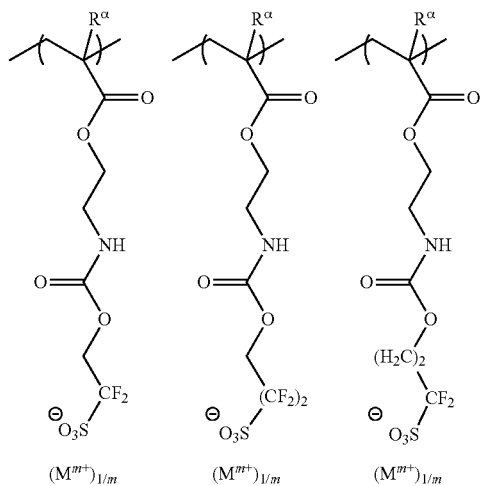
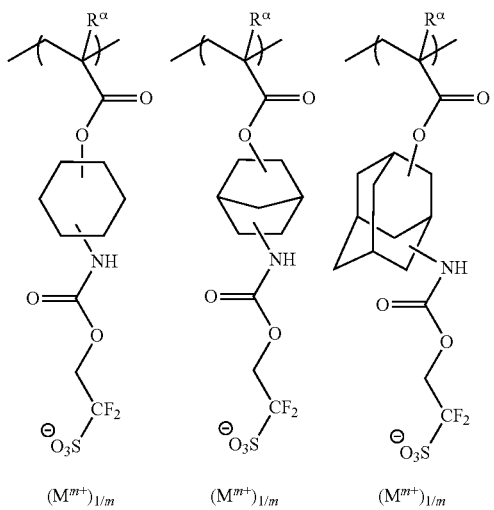
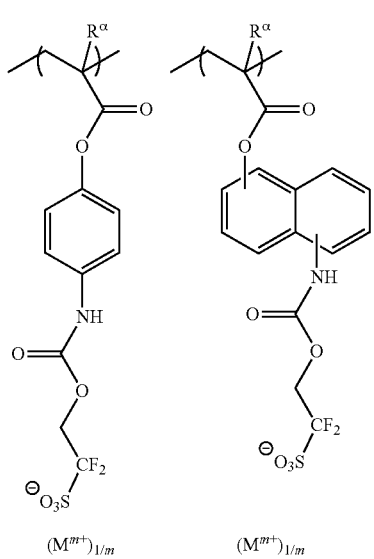
Specific examples of structural unit represented by formula (a6a-5) are shown below.
[Chemical Formula 40]
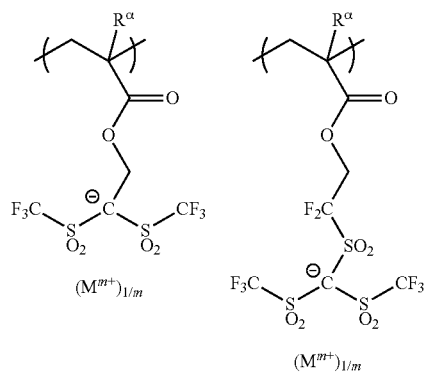
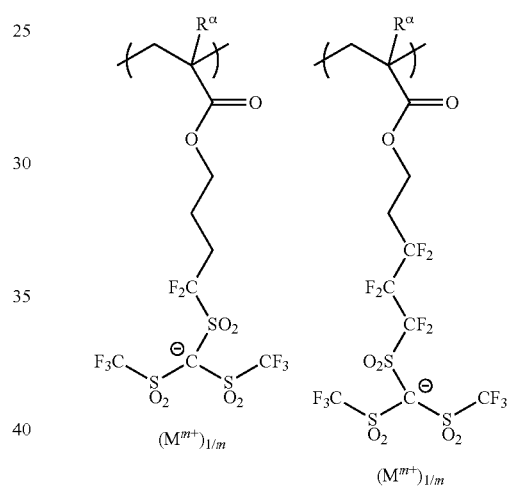
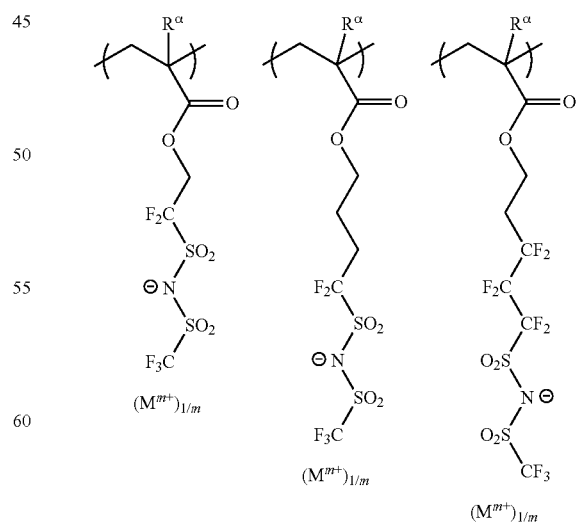
Specific examples of structural unit represented by formula (a6a-6) are shown below.

[Chemical Formula 41]
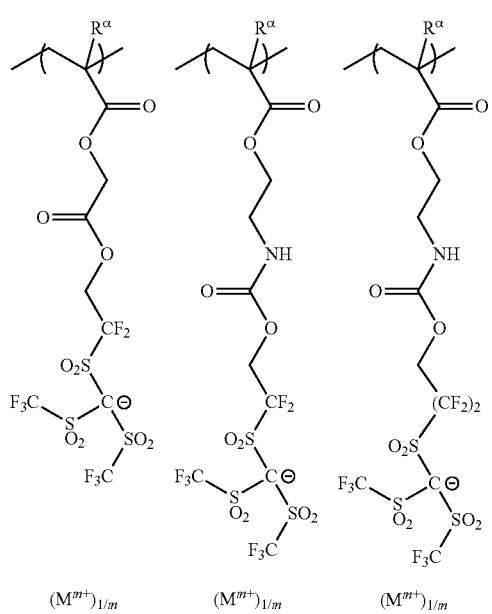
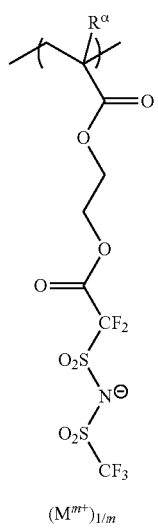
Specific examples of structural unit represented by formula (a6a-7) are shown below.
[Chemical Formula 42]
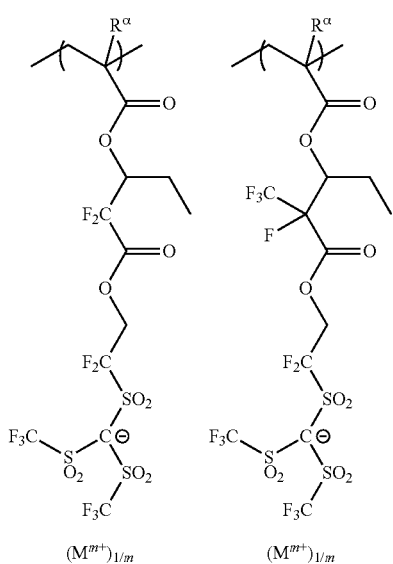
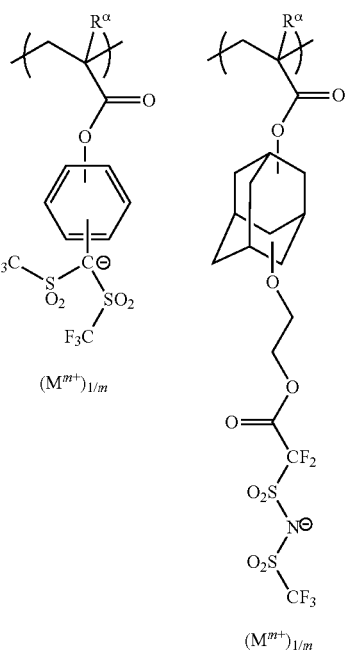

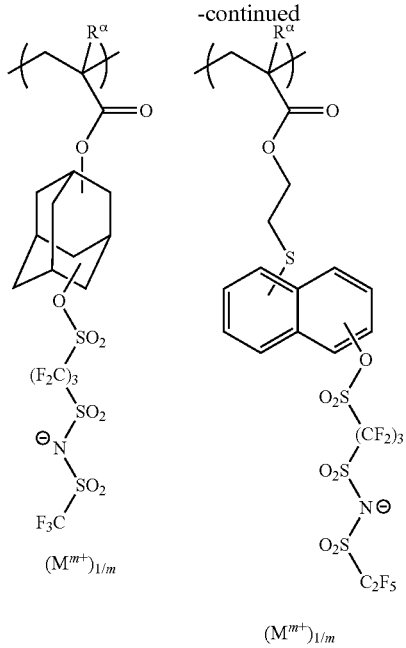

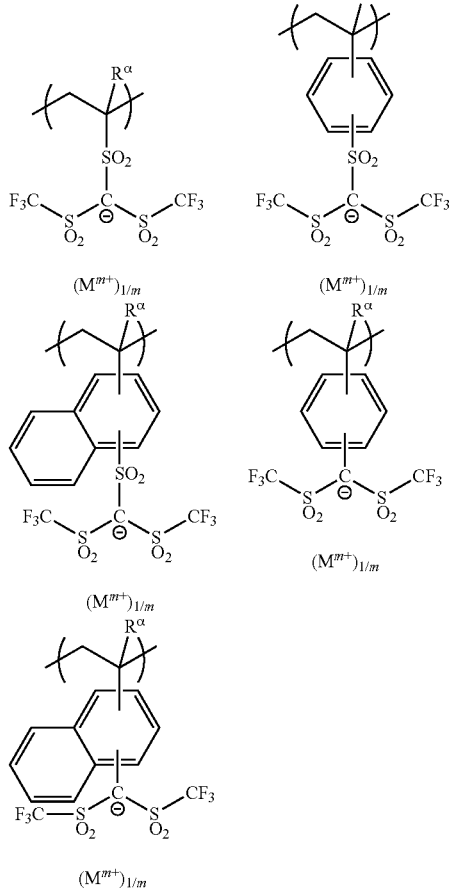

[Chemical Formula 43]

Structural Unit (a6c)

The structural unit (a6a) is a structural unit having a cation group which is decomposed upon exposure on a side chain thereof.

The cation group decomposed upon exposure is not particularly limited, and a group represented by general formula (a6c-r-1) shown below is preferable.

[Chemical Formula 44]

(a6c-r-1)

In the formula, $Ra'^{61c}$ and $Ra'^{62c}$ each independently represents an aryl group which may have a substituent, an alkyl group which may have a substituent or an alkenyl group which may have a substituent; $Va'^{61}$ represents an arylene group, an alkylene group or an alkenylene group; provided that $Ra'^{61c}$, $Ra'^{62c}$ and $Va'^{61c}$, may be mutually bonded to form a ring with the sulfur atom.

In formula (a6c-r-1), $Ra'^{61c}$ and $Ra'^{62c}$ each independently represents an aryl group which may have a substituent, an alkyl group which may have a substituent or an alkenyl group which may have a substituent; $Ra'^{61c}$ and $Ra'^{62c}$ are the same as defined for the "aryl group which may have a substituent",

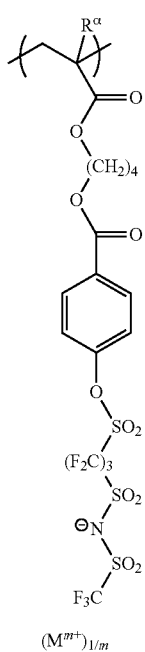

Specific examples of structural unit represented by formula (a6a-8) are shown below.

the "alkyl group which may have a substituent" and the "alkenyl group which may have a substituent" for $R^{201}$ to $R^{203}$ in formula (ca-1) described later.

$Va'^{61c}$ represents an arylene group, an alkylene group or an alkenylene group, and examples thereof include a group in which one hydrogen atom has been removed from an aryl group, an alkyl group or an alkenyl group for $Ra'^{61c}$ and $Ra'^{62c}$.

$Ra'^{61c}$, $Ra'^{62c}$ and $Va'^{61c}$ may be mutually bonded to form a ring with the sulfur atom. Examples of the formed ring structure include a group in which one hydrogen atom has been removed from the ring formed by $R^{201}$ to $R^{203}$ mutually bonded with the sulfur atom in formula (ca-1) described later.

Preferable examples of the structural unit (a6c) include structural units represented by general formulae (a6c-1) to (a6c-3) shown below.

[Chemical Formula 45]

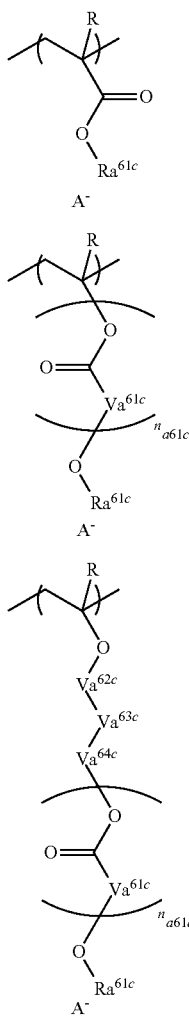

In the formula, R represents a hydrogen atom, an alkyl group of 1 to 5 carbon atoms or a halogenated alkyl group of 1 to 5 carbon atoms; each $Va^{61c}$ independently represents an alkylene group of 1 to 5 carbon atoms; $Va^{62c}$ and $Va^{64c}$ each independently represents an alkylene group of 1 to 10 carbon atoms; $Va^{63c}$ represents an aliphatic cyclic group or a single bond; $na^{61c}$ represents an integer of 0 to 2; $na^{62c}$ represents 0 or 1; $Ra^{61c}$ is a group represented by the aforementioned formula (a6c-r-1); and $A^-$ represents a counteranion.

In formulae (a6c-1) to (a6c-3), R is the same as defined for R in the aforementioned formula (a1-1). Each $Ra^{61c}$ independently represents a group represented by the aforementioned formula (a6c-r-1).

In formulae (a6c-2) and (a6c-3), each $Va^{61c}$ independently represents an alkylene group of 1 to 5 carbon atoms, preferably an alkylene group of 1 to 3 carbon atoms, and more preferably a methylene group.

In formula (a6c-3), $Va^{62c}$ and $Va^{64c}$ independently represents an alkylene group of 1 to 10 carbon atoms, preferably an alkylene group of 1 to 8 carbon atoms, more preferably an alkylene group of 1 to 5 carbon atoms, and still more preferably an alkylene group of 1 to 3 carbon atoms.

In formula (a6c-3), $Va^{63c}$ represents an aliphatic cyclic group or a single bond. The aliphatic cyclic group for $Va^{63c}$ is the same as defined for the aliphatic cyclic group explained above in relation to $Va'^{61}$ in the aforementioned formula (a6a-r-1).

$na^{61c}$ represents an integer of 0 to 2, preferably 1 or 2.

$na^{62c}$ represents 0 or 1.

In formulae (a6c-1) to (a6c-3), $A^-$ represents a counteranion.

The counteranion for $A^-$ is not particularly limited, and examples thereof include the anion moiety of an onium salt acid generator represented by general formula (b-1), (b-2) or (b-3) described later in relation to the component (B). The counteranion is preferably the anion moiety of an onium salt acid generator represented by general formula (b-1), more preferably a fluorinated alkylsulfonate ion of 1 to 8 carbon atoms (preferably 1 to 4 carbon atoms) or at least one member selected from anions represented by general formulae (an-1) to (an-3) described later.

Specific examples of the structural unit represented by formula (a6c-1), (a6c-2) or (a6c-3) are shown below. $A^-$ is the same as defined above.

[Chemical Formula 46]

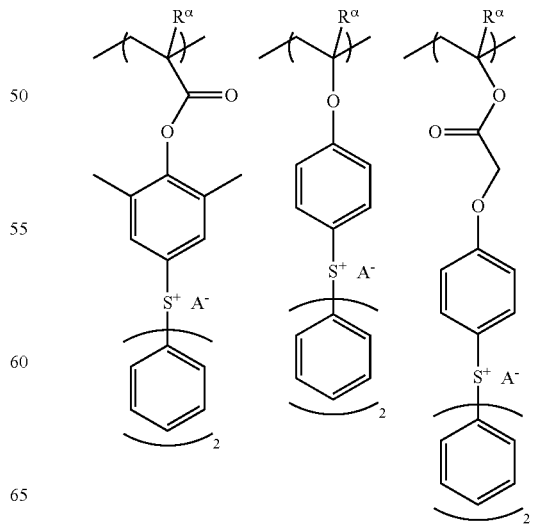

-continued

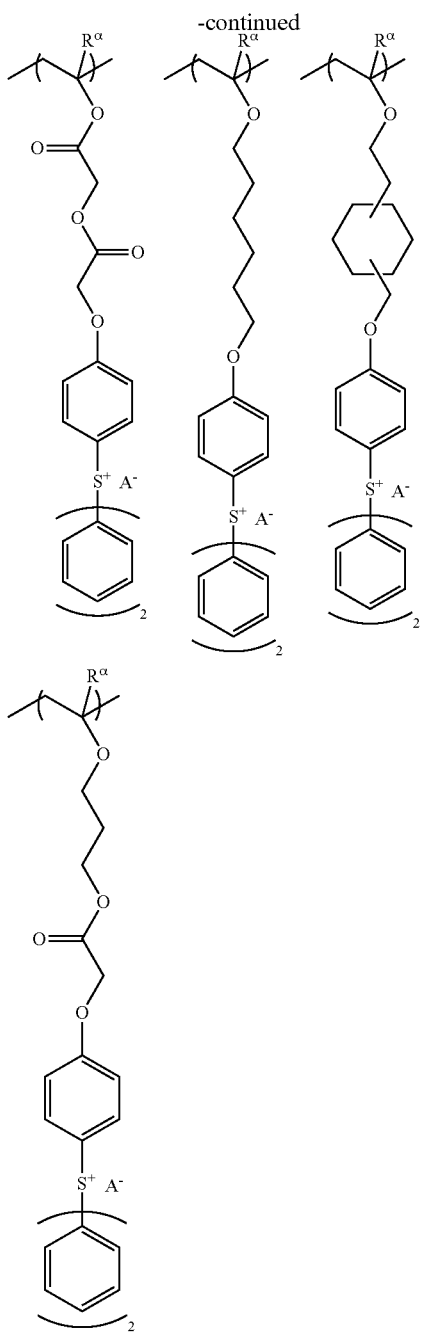

As the structural unit (a6) contained in the component (A1), 1 kind of structural unit may be used, or 2 or more kinds of structural units may be used.

As the structural unit (a6a), a structural unit represented by general formula (a6a-1) or (a6a-2) is preferable. As the structural unit (a6c), a structural unit represented by general formula (a6c-1) shown below is preferable.

Among these, as the structural unit (a6), the structural unit (a6a) is preferable.

The amount of the structural unit (a6) within the component (A1) based on the combined total of all structural units constituting the component (A1) is preferably 0.5 to 30 mol %, more preferably 1 to 20 mol %, and still more preferably 1.5 to 15 mol %.

When the amount of the structural unit (a6) is at least as large as the lower limit of the above-mentioned range, rough-ness can be reduced, and an excellent resist pattern can be reliably obtained. On the other hand, when the amount of the structural unit (a6) is no more than the upper limit of the above-mentioned range, a good balance can be achieved with the other structural units, and the lithography properties can be improved.

In the resist composition of the present embodiment, the component (A) contains a polymeric compound (A1) having a structural unit (a0).

Preferable examples of the component (A1) include a polymeric compound consisting of a repeating structure of the structural unit (a0) and the structural unit (a2); a polymeric compound consisting of a repeating structure of the structural unit (a0) and the structural unit (a3); a polymeric compound consisting of a repeating structure of the structural unit (a0) and the structural unit (a6); a polymeric compound consisting of a repeating structure of the structural unit (a0), the structural unit (a2) and the structural unit (a3); and a polymeric compound consisting of a repeating structure of the structural unit (a0), the structural unit (a2), the structural unit (a3) and the structural unit (a6). Among these examples, a polymeric compound consisting of a repeating structure of the structural unit (a0), the structural unit (a2) and the structural unit (a3), and a polymeric compound consisting of a repeating structure of the structural unit (a0), the structural unit (a2), the structural unit (a3) and the structural unit (a6) are more preferable.

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000.

When the Mw of the component (A1) is no more than the upper limit of the above-mentioned preferable range, the resist composition exhibits a satisfactory solubility in a resist solvent. On the other hand, when the Mw of the component (A1) is at least as large as the lower limit of the above-mentioned preferable range, dry etching resistance and the cross-sectional shape of the resist pattern becomes satisfactory.

The dispersity (Mw/Mn) of the component (A1) is not particularly limited, but is preferably 1.0 to 5.0, more preferably 1.0 to 4.0, and most preferably 1.0 to 3.0. Here, Mn is the number average molecular weight.

As the component (A), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. In particular, when the amount of the component (A1) is 25% by weight or more, the resolution of the pattern is improved, and various lithography properties such as exposure latitude (EL margin), line width roughness and mask reproducibility may be more reliably obtained.

In the resist composition of the present embodiment, as the component (A), "a base component which exhibits changed solubility in a developing solution under action of acid" other than the component (A1) (hereafter, referred to as "component (A2)") may be used in combination.

The component (A2) is not particularly limited, and any of the multitude of conventional base components used within chemically amplified resist compositions (e.g., base resins used within chemically amplified resist compositions for ArF excimer lasers or KrF excimer lasers, preferably ArF excimer lasers, low-molecular weight compounds) may be used. As the component (A2), one kind of resin may be used, or two or more kinds of resins may be used in combination.

In the resist composition of the present embodiment, as the component (A), one kind of composition may be used, or two or more kinds of compositions may be used in combination.

In the resist composition of the present embodiment, the amount of the component (A) can be appropriately adjusted depending on the thickness of the resist film to be formed, and the like.

<Other Components>

The resist composition of the present embodiment may contain, in addition to the aforementioned component (A), any other components other than the component (A). Examples of the other components include the component (B), the component (D), the component (E), the component (F) and the component (S) described below.

[Component (B): Acid-Generator Component]

The resist composition of the present embodiment may include, in addition to the component (A), an acid-generator component (hereafter, sometimes referred to as "component (B)").

As the component (B), there is no particular limitation, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 47]

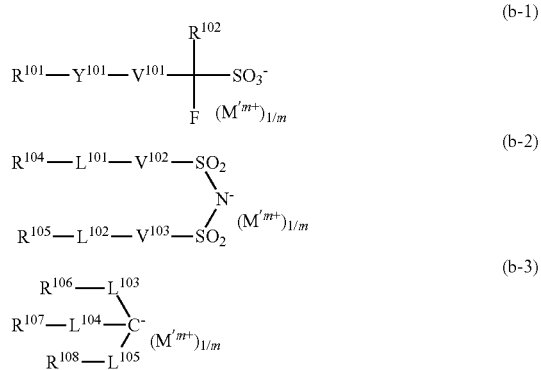

In the formulae, $R^{101}$ and $R^{104}$ to $R^{108}$ each independently represents a cyclic group which may have a substituent, a chain-like alkyl group which may have a substituent or a chain-like alkenyl group which may have a substituent, provided that $R^{104}$ and $R^{105}$ may be mutually bonded to form a ring;

$R^{102}$ represents a fluorine atom or a fluorinated alkyl group of 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; m represents an integer of 1 or more; and $M'^{m+}$ represents an m-valent onium cation.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic group which may have a substituent:

The cyclic group is preferably a cyclic hydrocarbon group, and the cyclic hydrocarbon group may be either an aromatic hydrocarbon group or an aliphatic hydrocarbon group. An "aliphatic hydrocarbon group" refers to a hydrocarbon group that has no aromaticity. The aliphatic hydrocarbon group may be either saturated or unsaturated, but in general, the aliphatic hydrocarbon group is preferably saturated.

The aromatic hydrocarbon group for $R^{101}$ is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group represented by $R^{101}$ include benzene, fluorene, naphthalene, anthracene, phenanthrene and biphenyl; and aromatic hetero rings in which part of the carbon atoms constituting the aforementioned aromatic rings has been substituted with a hetero atom. Examples of the hetero atom within the aromatic hetero rings include an oxygen atom, a sulfur atom and a nitrogen atom.

Specific examples of the aromatic hydrocarbon group represented by $R^{101}$ include a group in which one hydrogen atom has been removed from the aforementioned aromatic ring (i.e., an aryl group, such as a phenyl group or a naphthyl group), and a group in which one hydrogen of the aforementioned aromatic ring has been substituted with an alkylene group (e.g., an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and most preferably 1.

Examples of the cyclic aliphatic hydrocarbon group for $R^{101}$ include aliphatic hydrocarbon groups containing a ring in the structure thereof.

As examples of the hydrocarbon group containing a ring in the structure thereof, an alicyclic hydrocarbon group (a group in which one hydrogen atom has been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the polycyclic group preferably has 7 to 30 carbon atoms. Among polycycloalkanes, a polycycloalkane having a bridged ring polycyclic skeleton, such as adamantane, norbornane, isobornane, tricyclodecane or tetracyclododecane, and a polycycloalkane having a condensed ring polycyclic skeleton, such as a cyclic group having a steroid skeleton are preferable.

In the present specification, a "steroid skeleton" refers to a skeleton (st) represented by the chemical formula shown below which has three 6-membered rings and one 5-membered ring bonded.

[Chemical Formula 48]

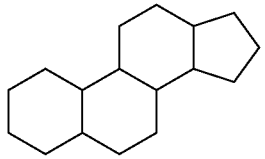

(st)

Among these examples, as the cyclic aliphatic hydrocarbon group for $R^{101}$, a group in which one or more hydrogen atoms have been removed from a monocycloalkane or a polycycloalkane is preferable, a group in which one or more hydrogen atoms have been removed from a polycycloalkane is more preferable, an adamantyl group or a norbornyl group is still more preferable, and an adamantyl group is most preferable.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, branched alkylene groups are preferred, and specific examples include various alkylalkylene groups, including alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The cyclic hydrocarbon group for $R^{101}$ may contain a hetero atom such as a heterocycle. Specific examples include lactone-containing cyclic groups represented by the aforementioned general formulae (a2-r-1) to (a2-r-7), the —SO$_2$— containing polycyclic group represented by the aforementioned formulae (a5-r-1) to (a5-r-4), and other heterocyclic groups shown below.

[Chemical Formula 49]

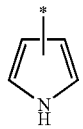
(r-hr-1)

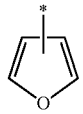
(r-hr-2)

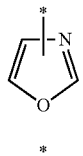
(r-hr-3)

(r-hr-4)

(r-hr-5)

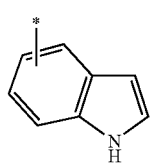
(r-hr-6)

(r-hr-7)

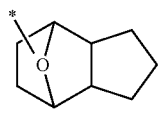
(r-hr-8)

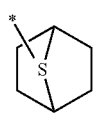
(r-hr-9)

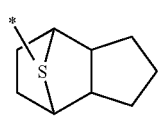
(r-hr-10)

(r-hr-11)

(r-hr-12)

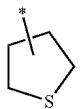
(r-hr-13)

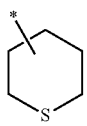
(r-hr-14)

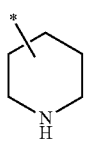
(r-hr-15)

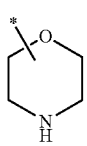
(r-hr-16)

As the substituent for the cyclic group for $R^{101}$, an alkyl group, an alkoxy group, a halogen atom, a halogenated alkyl group, a hydroxyl group, a carbonyl group, a nitro group or the like can be used.

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The carbonyl group as the substituent is a group that substitutes a methylene group ($-CH_2-$) constituting the cyclic hydrocarbon group.

Chain-like alkyl group which may have a substituent:
The chain-like alkyl group for $R^{101}$ may be linear or branched.

The linear alkyl group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain-like alkenyl group which may have a substituent:
The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylvinyl group, a 2-methylvinyl group, a 1-methylpropenyl group and a 2-methylpropenyl group.

Among these examples, as the chain-like alkenyl group, a linear alkenyl group is preferable, a vinyl group or a propenyl group is more preferable, and a vinyl group is most preferable.

As the substituent for the chain-like alkyl group or alkenyl group for $R^{101}$, an alkoxy group, a halogen atom, a halogenated alkyl group, a hydroxyl group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an $-SO_2-$ containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; $-O-$), an ester bond ($-C(=O)-O-$), an oxycarbonyl group ($-O-C(=O)-$), an amido bond ($-C(=O)-NH-$), a carbonyl group ($C(=O)$) and a carbonate bond ($-O-C(=O)-O-$); and combinations of the aforementioned non-hydrocarbon, hetero atom-containing linking groups with an alkylene group. Furthermore, the combinations may have a sulfonyl group ($-SO_2-$) bonded thereto. Examples of divalent linking groups containing an oxygen atom include linking groups represented by general formulae (y-al-1) to (y-al-7) shown below.

[Chemical Formula 50]

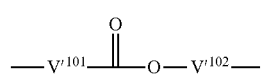
(y-al-1)

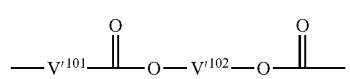
(y-al-2)

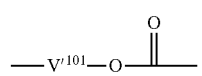
(y-al-3)

-continued $$—V'^{101}—O— \quad (y\text{-}al\text{-}4)$$

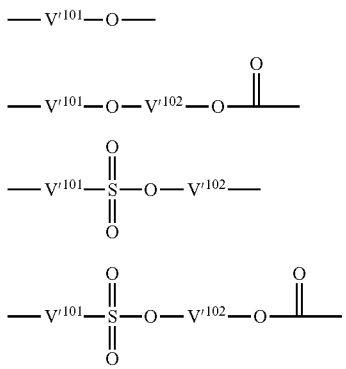

In the formulae, $V'^{101}$ represents a single bond or an alkylene group of 1 to 5 carbon atoms; $V'^{102}$ represents a divalent saturated hydrocarbon group of 1 to 30 carbon atoms.

The divalent saturated hydrocarbon group for $V'^{102}$ is preferably an alkylene group of 1 to 30 carbon atoms, more preferably an alkylene group of 1 to 10 carbon atoms, and still more preferably an alkylene group of 1 to 5 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; an alkylethylene group, such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$—]; an alkyltrimethylene group, such as —$CH(CH_3)CH_2CH_2$— and —$CH_2CH(CH_3)CH_2$—; a tetramethylene group [—$CH_2CH_2CH_2CH_2$—]; an alkyltetramethylene group, such as —$CH(CH_3)CH_2CH_2CH_2$—, —$CH_2CH(CH_3)CH_2CH_2$—; and a pentamethylene group [—$CH_2CH_2CH_2CH_2CH_2$—].

Further, part of methylene group within the alkylene group for $V'^{101}$ and $V'^{102}$ may be substituted with a divalent aliphatic cyclic group of 5 to 10 carbon atoms. The aliphatic cyclic group is preferably a divalent group in which one hydrogen atom has been removed from the cyclic aliphatic hydrocarbon group (monocyclic aliphatic hydrocarbon group or polycyclic aliphatic hydrocarbon group) for $Ra'^{3}$ in the aforementioned formula (a1-r-1), and a cyclohexylene group, 1,5-adamantylene group or 2,6-adamantylene group is preferable.

$Y^{101}$ is preferably a divalent linking group containing an ether bond or a divalent linking group containing an ester bond, and groups represented by the aforementioned formulas (y-al-1) to (y-al-5) are preferable.

In formula (b-1), $V^{101}$ represents a single bond, an alkylene group or a fluorinated alkylene group. The alkylene group and the fluorinated alkylene group for $V^{101}$ preferably has 1 to 4 carbon atoms. Examples of the fluorinated alkylene group for $V^{101}$ include a group in which part or all of the hydrogen atoms within the alkylene group for $V^{101}$ have been substituted with fluorine. Among these examples, as $V^{101}$, a single bond or a fluorinated alkylene group of 1 to 4 carbon atoms is preferable.

In formula (b-1), $R^{102}$ represents a fluorine atom or a fluorinated alkyl group of 1 to 5 carbon atoms. $R^{102}$ is preferably a fluorine atom or a perfluoroalkyl group of 1 to 5 carbon atoms, and more preferably a fluorine atom.

As a specific example of the anion moiety for the component (b-1), in the case where $Y^{101}$ a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by formulae (an-1) to (an-3) shown below can be mentioned.

[Chemical Formula 51]

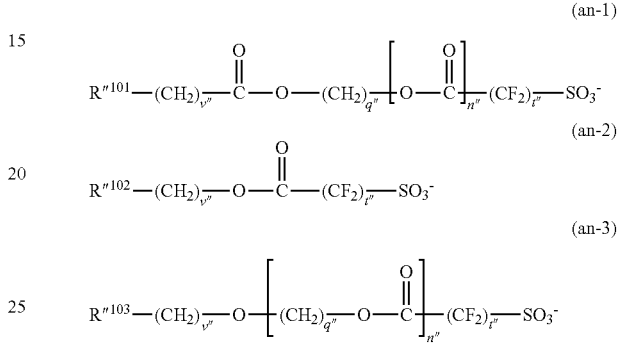

In the formulae, $R'''^{101}$ represents an aliphatic cyclic group which may have a substituent, a group represented by any one of the aforementioned formulas (r-hr-1) to (r-hr-6) or a chain-like alkyl group which may have a substituent; $R'''^{102}$ represents an aliphatic cyclic group which may have a substituent, a lactone-containing cyclic group represented by any one of the aforementioned formulae (a2-r-1) to (a2-r-7) or an —$SO_2$— containing cyclic group represented by any one of the aforementioned formulae (a5-r-1) to (a5-r-4); $R'''^{103}$ represents an aromatic cyclic group which may have a substituent, an aliphatic cyclic group which may have a substituent or a chain-like alkenyl group which may have a substituent; $v''$ represents an integer of 0 to 3; $q''$ represents an integer of 1 to 20; $t''$ represents an integer of 1 to 3; and $n''$ represents 0 or 1.

As the aliphatic cyclic group for $R'''^{101}$, $R'''^{102}$ and $R'''^{103}$ which may have a substituent, the same groups as the cyclic aliphatic hydrocarbon group for $R^{101}$ described above are preferable. As the substituent, the same groups as those described above for substituting the cyclic aliphatic hydrocarbon group for $R^{101}$ can be mentioned.

As the aromatic cyclic group for $R'''^{103}$ which may have a substituent, the same groups as the aromatic hydrocarbon group for the cyclic hydrocarbon group represented by $R^{101}$ described above are preferable. The substituent is the same as defined for the substituent for the aromatic hydrocarbon group represented by $R^{101}$.

As the chain-like alkyl group for $R'''^{101}$ which may have a substituent, the same groups as those described above for $R^{101}$ are preferable. As the chain-like alkenyl group for $R'''^{103}$ which may have a substituent, the same groups as those described above for $R^{101}$ are preferable.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and is the same as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$, the more the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved.

The fluorination ratio of the chain-like alkyl group is preferably from 70 to 100%, more preferably from 90 to 100%, and it is particularly desirable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as defined for $R^{101}$ in formula (b-1).

$L^{103}$ to $L^{105}$ each independently represents a single bond, —CO— or —SO$_2$—.

{Cation Moiety}

In formulae (b-1), (b-2) and (b-3), m represents an integer of 1 or more, $M^{m+}$ represents an onium cation having a valency of m, preferably a sulfonium cation or an iodonium cation, and most preferably an organic cation represented by any one of the following formulae (ca-1) to (ca-4).

[Chemical Formula 52]

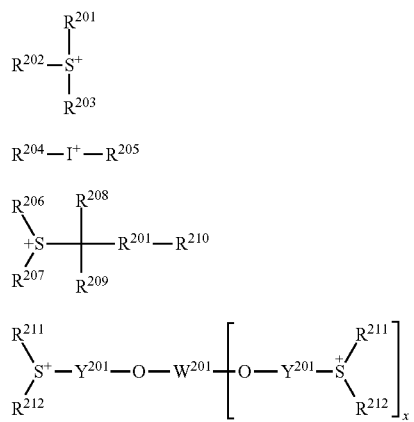

In the formulae, $R^{201}$ to $R^{207}$, $R^{211}$ and $R^{212}$ independently represents an aryl group, an alkyl group or an alkenyl group, provided that two of $R^{201}$ to $R^{203}$, $R^{206}$ and $R^{207}$, or $R^{211}$ and $R^{212}$ may be mutually bonded to form a ring with the sulfur atom; $R^{208}$ and $R^{209}$ each independently represents a hydrogen atom or an alkyl group of 1 to 5 carbon atoms; $R^{210}$ represents an aryl group which may have a substituent, an alkyl group which may have a substituent, an alkenyl group which may have a substituent, or an —SO$_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group of 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Specific examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by formulae (ca-r-1) to (ca-r-7) shown below.

[Chemical Formula 53]

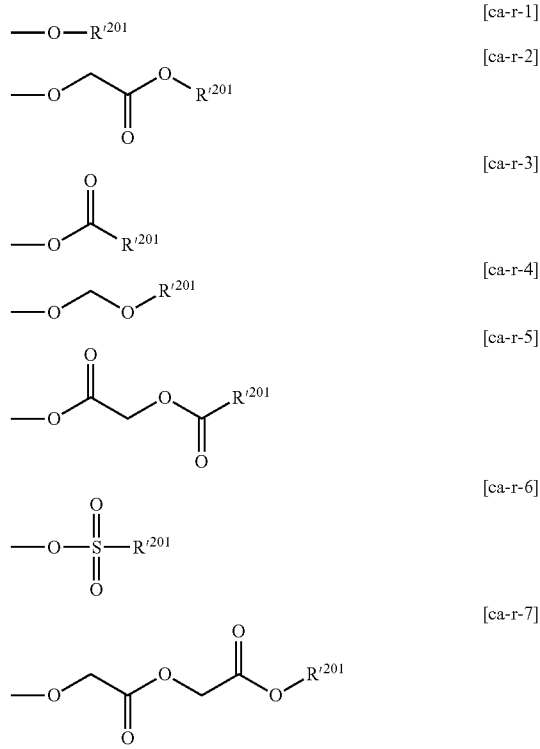

In the formulae, each $R'^{201}$ independently represents a hydrogen atom, a cyclic group which may have a substituent, a chain-like alkyl group which may have a substituent, or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R^{101}$ can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group of 1 to 5 carbon atoms). The ring containing the sulfur atom in the skeleton thereof is preferably a 3 to 10-membered ring, and most preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represents a hydrogen atom or an alkyl group of 1 to 5 carbon atoms, preferably a hydrogen atom or an alkyl group of 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group of 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

The —SO$_2$— containing cyclic group for $R^{210}$ which may have a substituent is the same as defined for the aforementioned "—SO$_2$— containing cyclic group", and the group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

Examples of the alkylene group and alkenylene group for $Y^{201}$ include groups in which one hydrogen atom has been removed from the chain-like alkyl group or the chain-like alkenyl group given as an example of $R^{101}$ in the aforementioned formula (b-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups (which may have a substituent) as those described above for Ya$^{21}$ in the general formula (a2-1) can be mentioned. The divalent linking group for $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly desirable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations represented by formulae (ca-1-1) to (ca-1-67) shown below.

[Chemical Formula 54]

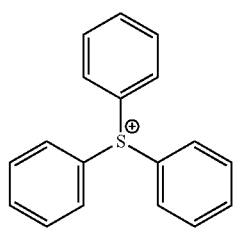

(ca-1-1)

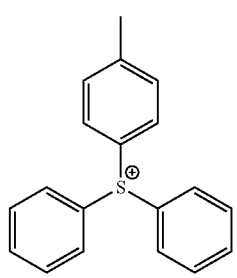

(ca-1-2)

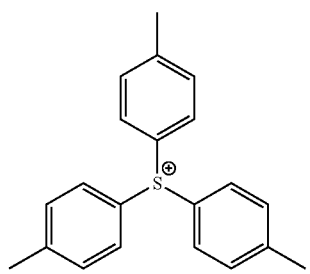

(ca-1-3)

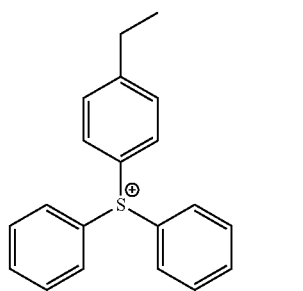

(ca-1-4)

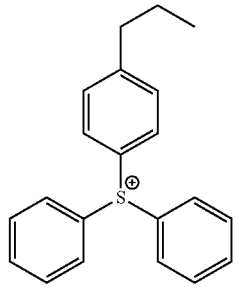

(ca-1-5)

(ca-1-6)
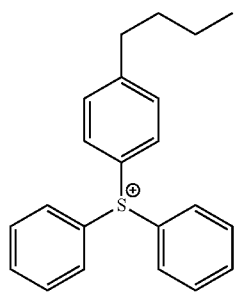
(ca-1-7)
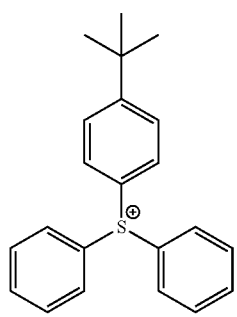
(ca-1-8)
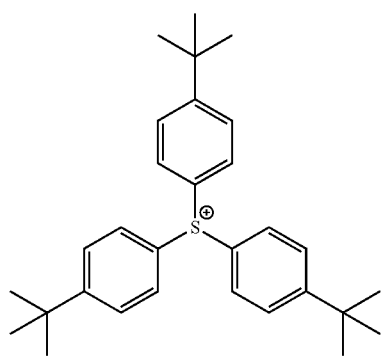
(ca-1-9)
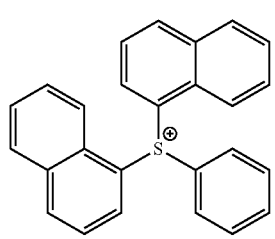
(ca-1-10)
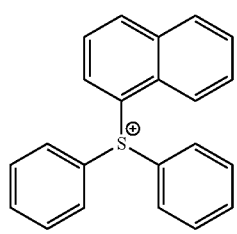
(ca-1-11)
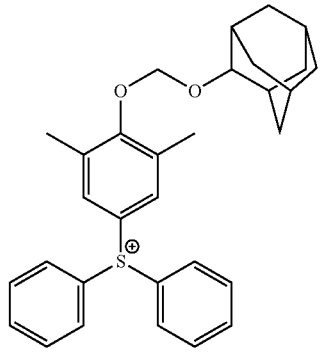
(ca-1-12)
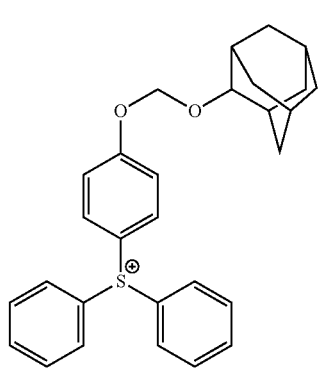
(ca-1-13)
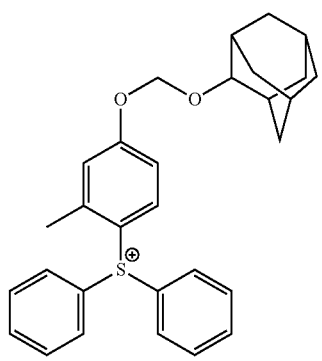
(ca-1-14)
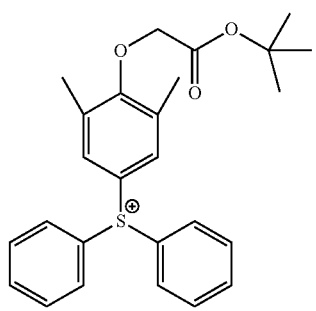

(ca-1-15)
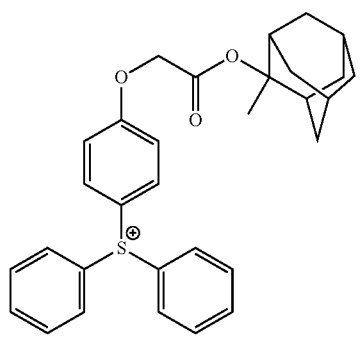
(ca-1-16)
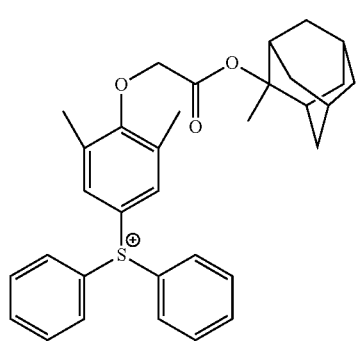
[Chemical Formula 55]
(ca-1-17)
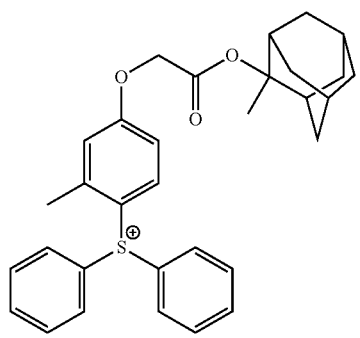
(ca-1-18)
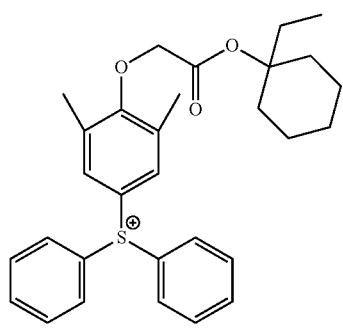
(ca-1-19)
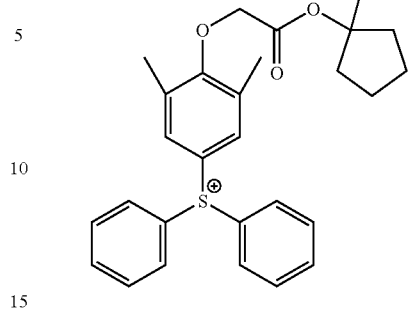
(ca-1-20)
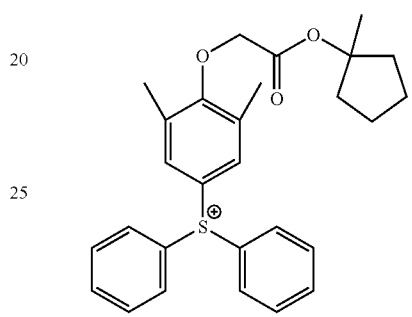
(ca-1-21)
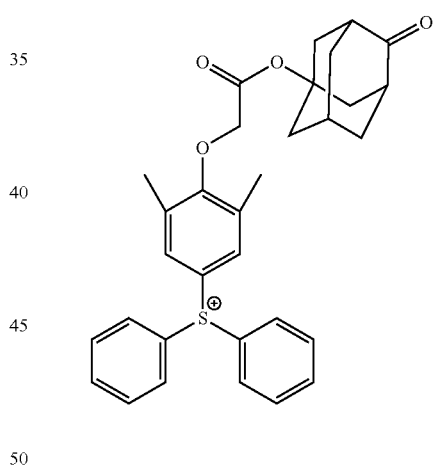
(ca-1-22)
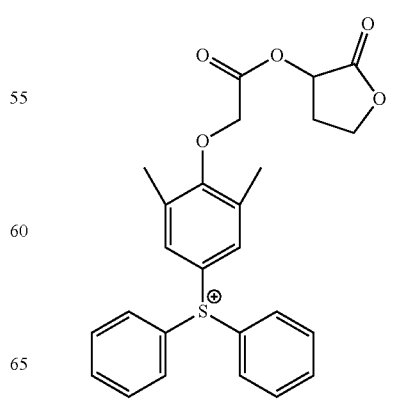

-continued
(ca-1-23)
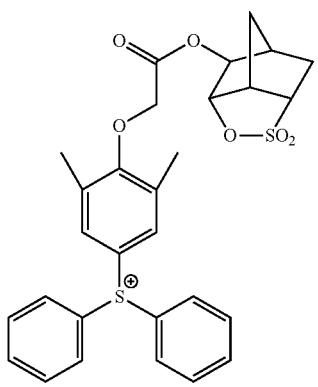
(ca-1-24)
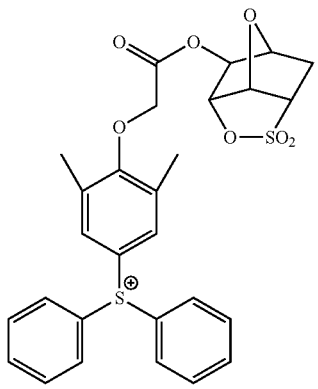
(ca-1-25)
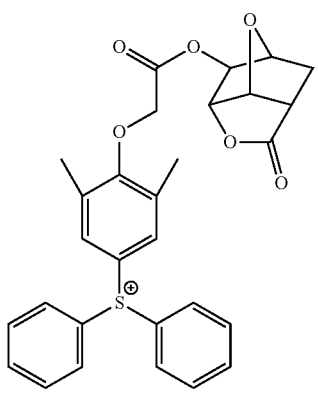
(ca-1-26)
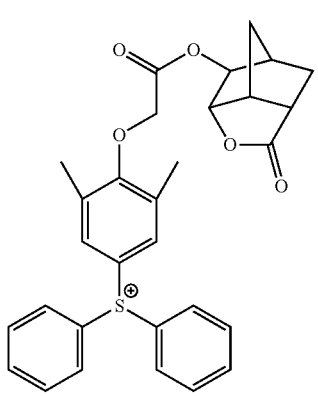
-continued
(ca-1-27)
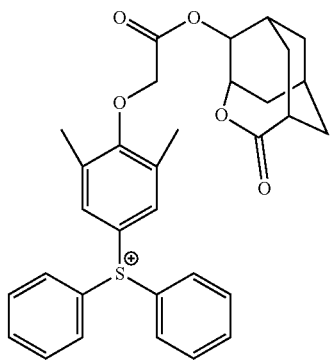
(ca-1-28)
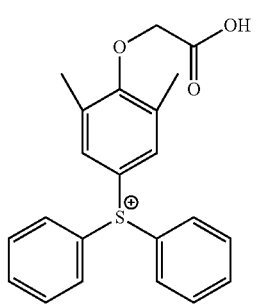
(ca-1-29)
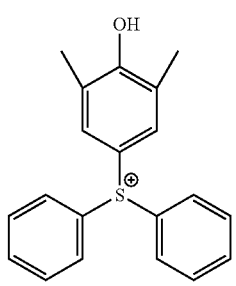
(ca-1-30)
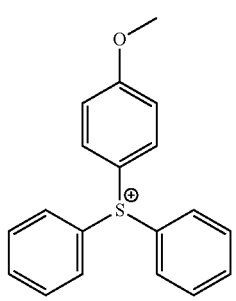
(ca-1-31)
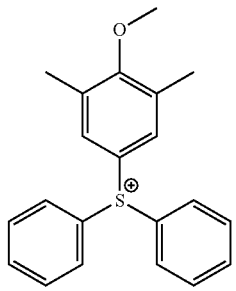

(ca-1-32)
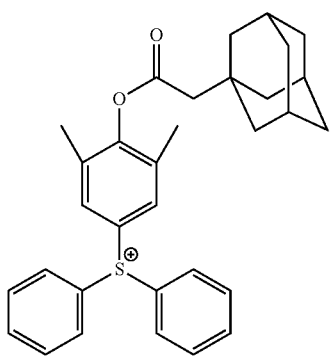
(ca-1-33)
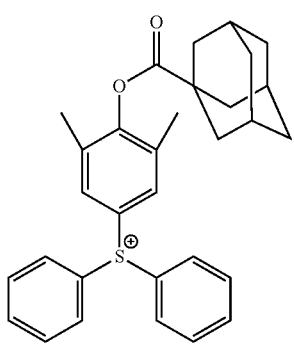
[Chemical Formula 56]
(ca-1-34)
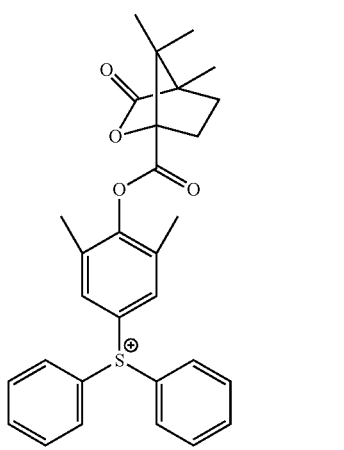
(ca-1-35)
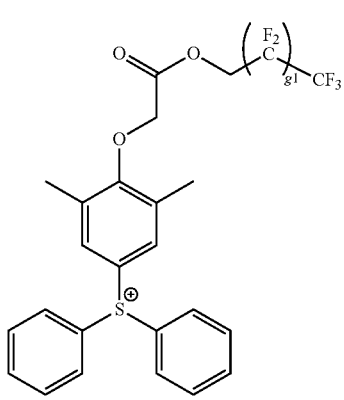
(ca-1-36)
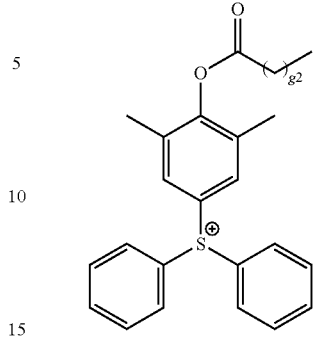
(ca-1-37)
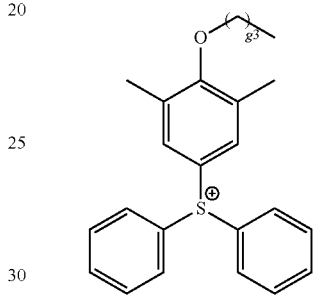
(ca-1-38)
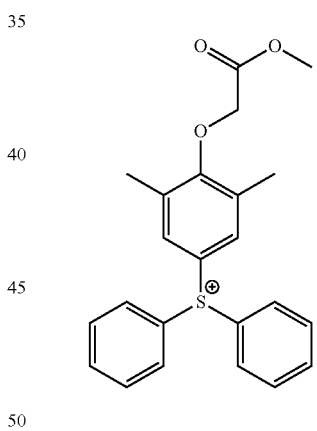
(ca-1-39)
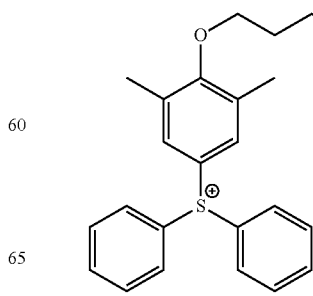

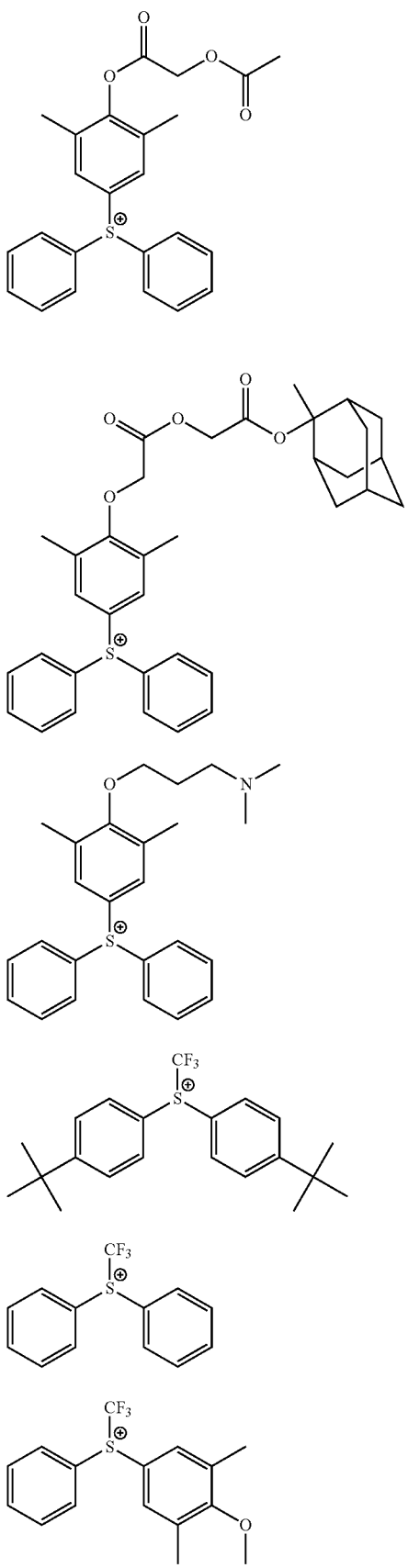
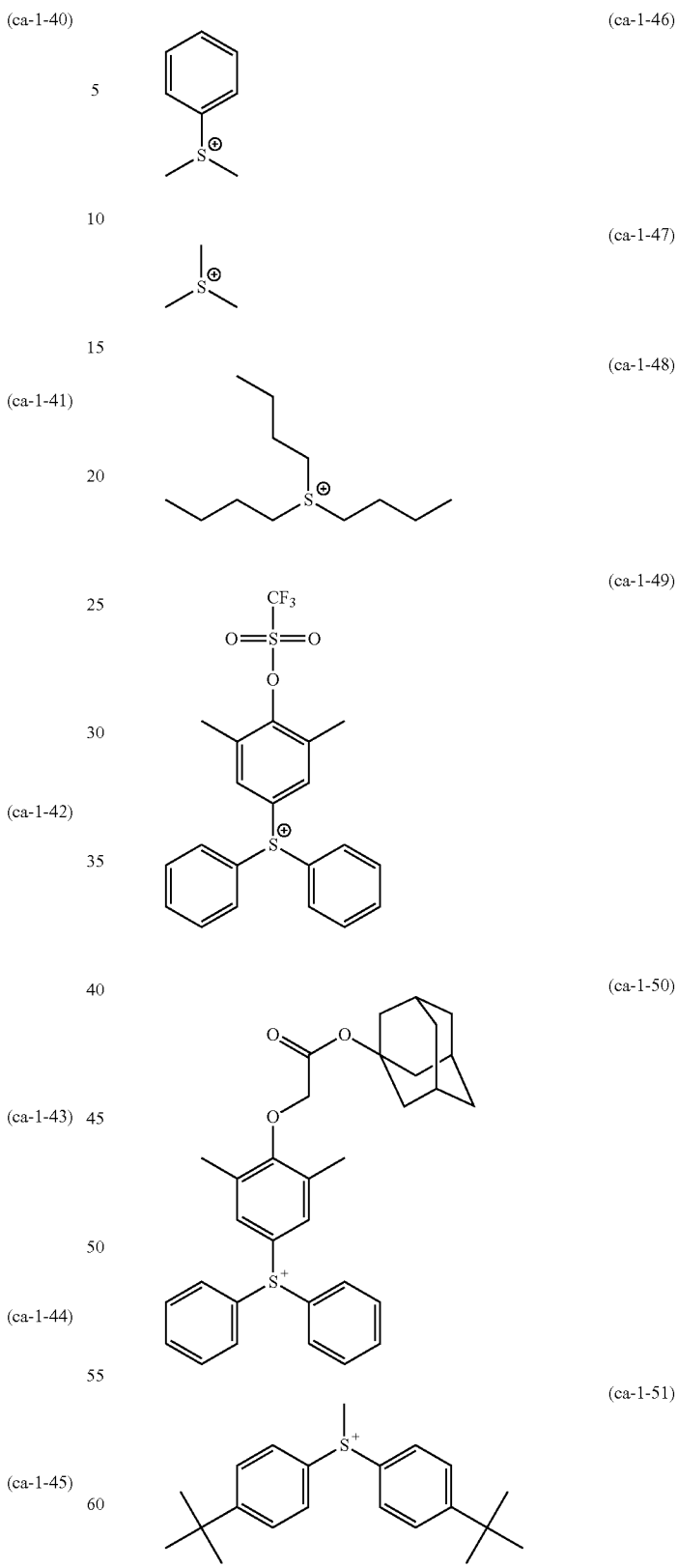
In the formulae, g1, g2 and g3 represent recurring numbers, wherein g1 is an integer of 1 to 5, g2 is an integer of 0 to 20, and g3 is an integer of 0 to 20.

[Chemical Formula 57]
(ca-1-52)
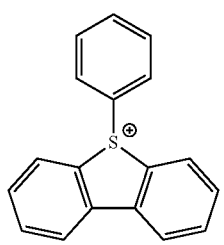
(ca-1-53)
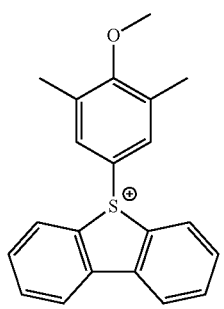
(ca-1-54)
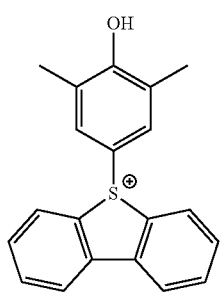
(ca-1-55)
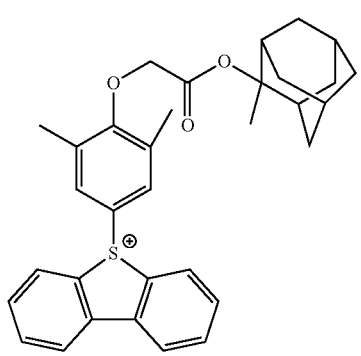
(ca-1-56)
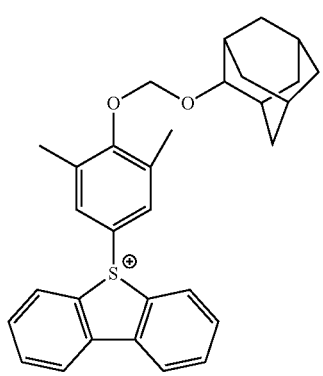
(ca-1-57)
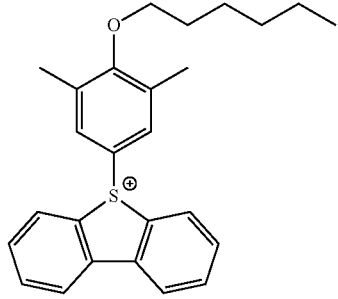
(ca-1-58)
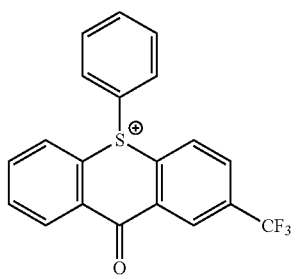
(ca-1-59)
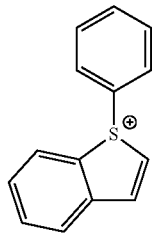
(ca-1-60)
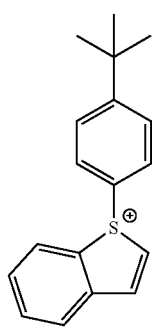
(ca-1-61)
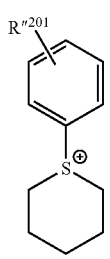

-continued (ca-1-62)
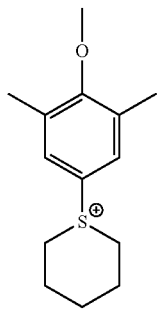

(ca-1-63)
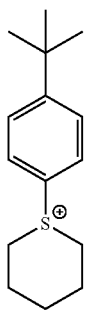

(ca-1-64)
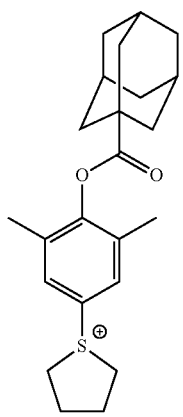

(ca-1-65)
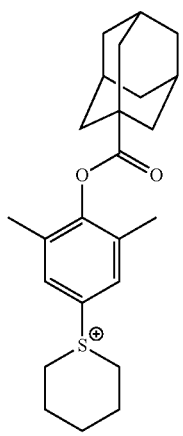

-continued (ca-1-66)
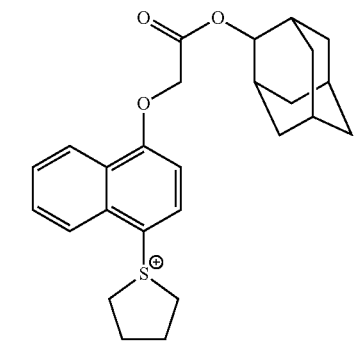

(ca-1-67)
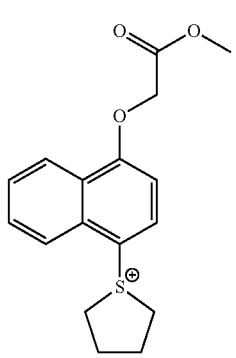

In the formulae, $R''^{201}$ represents a hydrogen atom or a substituent, and as the substituent, the same groups as those described above for substituting $R^{201}$ to $R^{207}$ and $R^{210}$ to $R^{212}$ can be mentioned.

Specific examples of preferable cations represented by the formula (ca-2) include a dihphenyliodonium cation and a bis(4-tert-butylphenyl)iodonium cation.

Specific examples of preferable cations represented by formula (ca-3) include cations represented by formulae (ca-3-1) to (ca-3-6) shown below.

[Chemical Formula 58]

(ca-3-1)
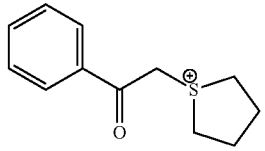

(ca-3-2)
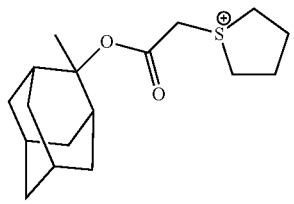

(ca-3-3)
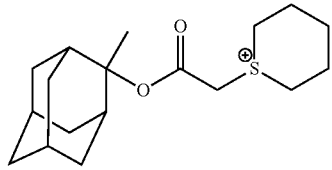

-continued

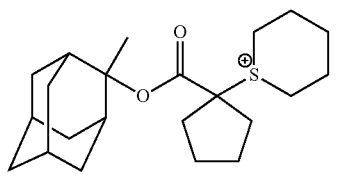
(ca-3-4)

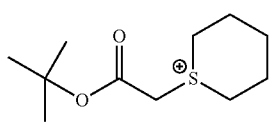
(ca-3-5)

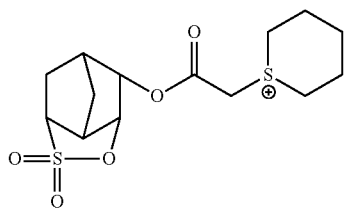
(ca-3-6)

Specific examples of preferable cations represented by formula (ca-4) include cations represented by formulae (ca-4-1) and (ca-4-2) shown below.

[Chemical Formla 59]

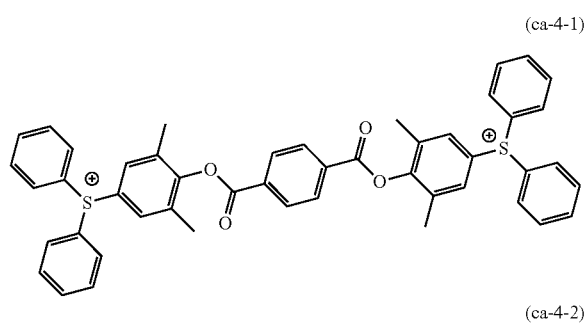
(ca-4-1)

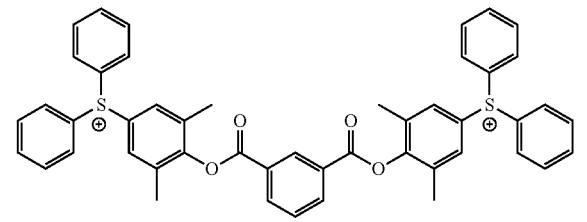
(ca-4-2)

Among the above examples, as the cation moiety $[(M^{m+})_{1/m}]$, a cation represented by general formula (ca-1) is preferable, and a cation represented by any one of formulae (ca-1-1) to (ca-1-67) is more preferable.

As the component (B), one type of these acid generators may be used alone, or two or more types may be used in combination.

When the resist composition contains the component (B), the amount of the component (B) relative to 100 parts by weight of the component (A) is preferably within a range from 0.5 to 60 parts by weight, more preferably from 1 to 50 parts by weight, and still more preferably from 1 to 40 parts by weight.

When the amount of the component (B) is within the above-mentioned range, formation of a resist pattern can be satisfactorily performed. Further, by virtue of the above-mentioned range, when each of the components are dissolved in an organic solvent, a homogeneous solution may be more reliably obtained and the storage stability of the resist composition becomes satisfactory.

[Component (D): Acid Diffusion Control Agent]

Moreover, the resist composition of the present embodiment may include an acid diffusion control agent component (hereafter, frequently referred to as "component (D)"), in addition to the component (A), or in addition to the component (A) and the component (B).

The component (D) functions as an acid diffusion control agent, i.e., a quencher which traps the acid generated in the resist composition upon exposure.

The component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

Component (D1)

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions of the resist film, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 60]

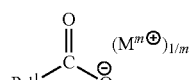
(d1-1)

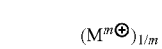
(d1-2)

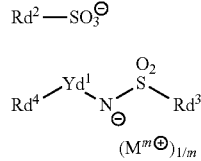
(d1-3)

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) has no fluorine atom bonded thereto; $Yd^1$ represents a single bond or a divalent linking group; m represents an integer of 1 or more; and each $M^{m+}$ independently represents an organic cation having a valency of m.

{Component (d1-1)}

Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, as the group for $Rd^1$, an aromatic hydrocarbon group which may have a substituent, an aliphatic cyclic group which may have a substituent and a chain-like alkyl group which may have a substituent are preferable. Examples of the substituent for these groups include a hydroxy group, an oxo group, an alkyl group, an aryl group, a fluorine atom, a fluorinated alkyl group, a lactone-containing cyclic group represented by any one of the aforementioned formulae (a2-r-1) to (a2-r-7), an ether bond, an ester bond, and a combination thereof. In the case where an ether bond or an ester bond is included as the substituent, the substituent may be bonded via an alkylene group, and a linking group represented by any one of the aforementioned formulae (y-al-1) to (y-al-5) is preferable as the substituent.

The aromatic hydrocarbon group is preferably a phenyl group or a naphthyl group.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is particularly desirable.

Specific examples of preferable anion moieties for the component (d1-1) are shown below.

[Chemical Formula 61]

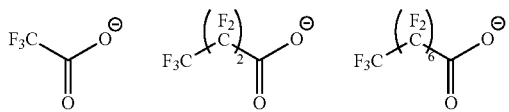

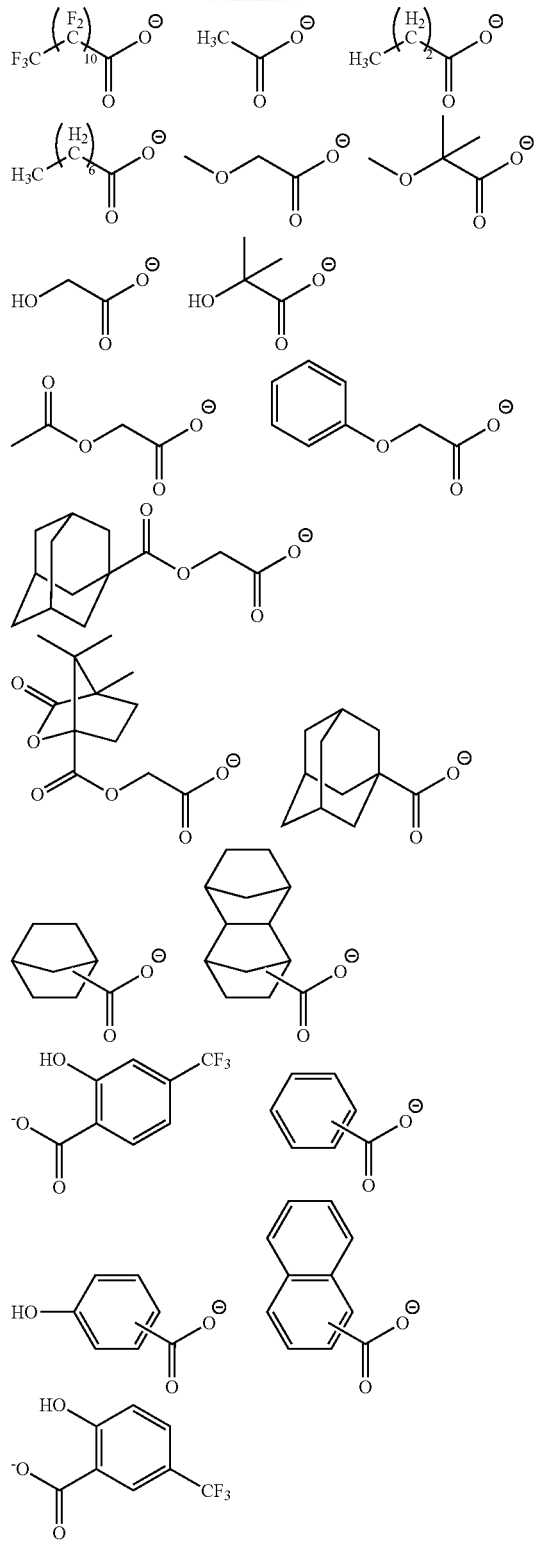

Cation Moiety

In formula (d1-1), $M^{m+}$ represents an organic cation having a valency of m.

As the organic cation for $M^{m+}$, for example, the same cation moieties as those represented by the aforementioned formulae (ca-1) to (ca-4) are preferable, cation moieties represented by the aforementioned general formulae (ca-1) is preferable, and cation moieties represented by the aforementioned formulae (ca-1-1) to (ca-1-67) are still more preferable.

As the component (d1-1), one type of compound may be used, or two or more types of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

provided that, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, a chain-like alkyl group which may have a substituent or an aliphatic cyclic group which may have a substituent is preferable. The chain-like alkyl group preferably has 1 to 10 carbon atoms, and more preferably 3 to 10 carbon atoms. As the aliphatic cyclic group, a group in which one or more hydrogen atoms have been removed from adamantane, norbornane, isobornane, tricyclodecane, tetracyclododecane or camphor (which may have a substituent) is more preferable.

The hydrocarbon group for $Rd^2$ may have a substituent. As the substituent, the same groups as those described above for substituting the hydrocarbon group (e.g., aromatic hydrocarbon group, aliphatic cyclic group, chain-like alkyl group) for $Rd^1$ in the formula (d1-1) can be mentioned.

Specific examples of preferable anion moieties for the component (d1-2) are shown below.

[Chemical Formula 62]

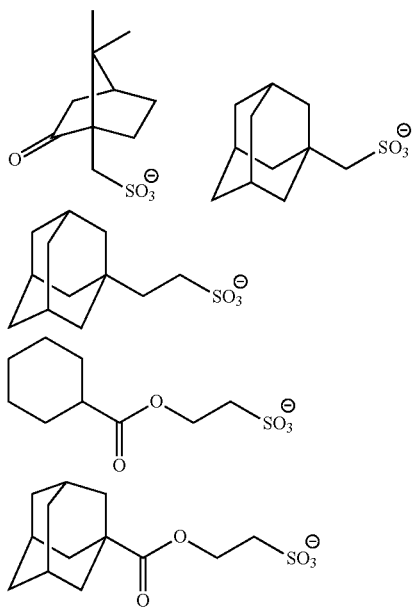

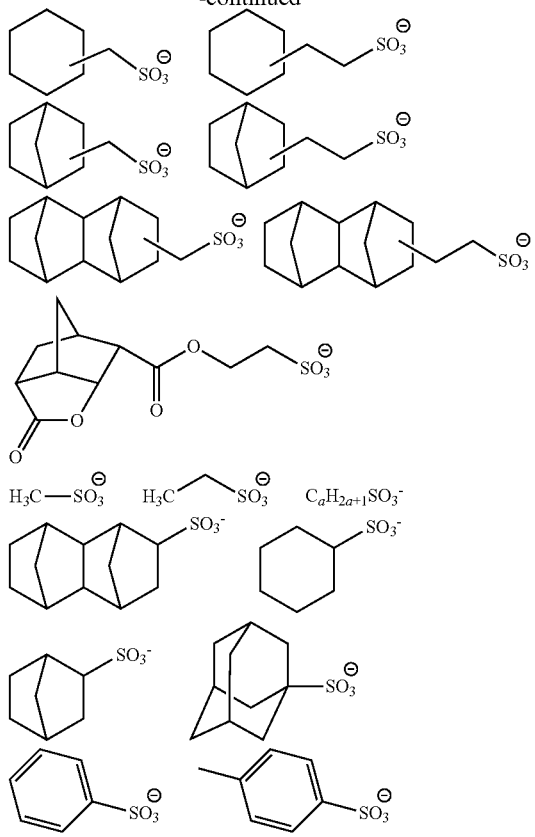

(a = 3~10)

Cation Moiety

In formula (d1-2), $M^{m+}$ is an organic cation having a valency of m, and is the same as defined for $M^{m+}$ in the aforementioned formula (d1-1).

As the component (d1-2), one type of compound may be used, or two or more types of compounds may be used in combination.

{Component (d1-3)}

Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$ in the aforementioned formula (b-1), and a cyclic group containing a fluorine atom, a chain-like alkyl group or a chain-like alkenyl group is preferable. Among these, a fluorinated alkyl group is preferable, and more preferably the same fluorinated alkyl groups as those described above for $Rd^1$.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$ in the aforementioned formula (b-1).

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ in the aforementioned formula (b-1) can be mentioned, and a vinyl group, a propenyl group (an allyl group), a 1-methylpropenyl group and a 2-methylpropenyl group are preferable. These groups may have an alkyl group of 1 to 5 carbon atoms or a halogenated alkyl group of 1 to 5 carbon atoms as a substituent.

As the cyclic group for $Rd^4$, the same groups as those described above for $R^{101}$ in the aforementioned formula (b-1) can be mentioned. Among these, as the cyclic group, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition exhibits an excellent photoabsorption efficiency in a lithography process using EUV or the like as the exposure source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. The divalent linking groups are the same as defined for the divalent hydrocarbon group which may have a substituent and the divalent linking group containing a hetero atom explained above as the divalent linking group for $Ya^{21}$ in the aforementioned formula (a2-1).

As $Yd^1$, a carbonyl group, an ester bond, an amide bond, an alkylene group or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 63]

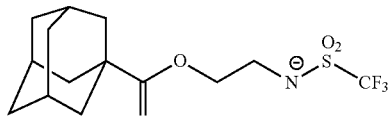
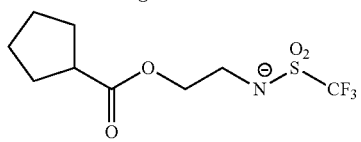
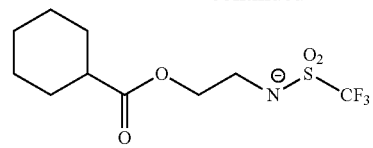
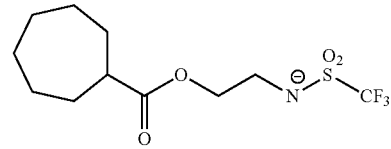
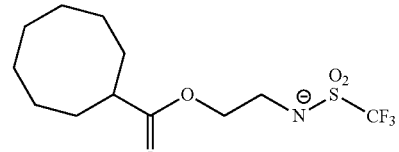
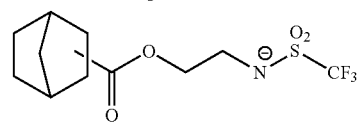
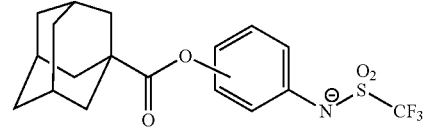
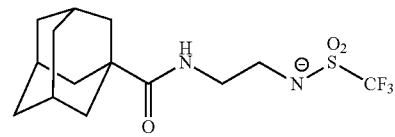
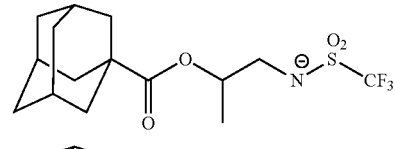
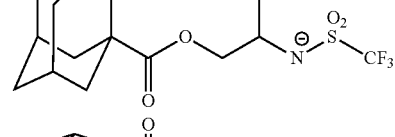
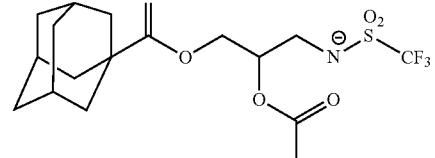
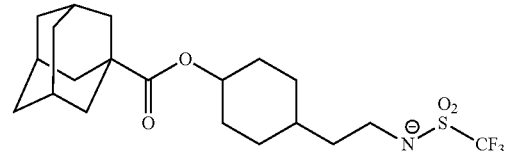
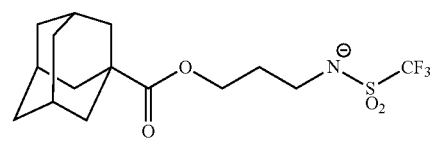

-continued

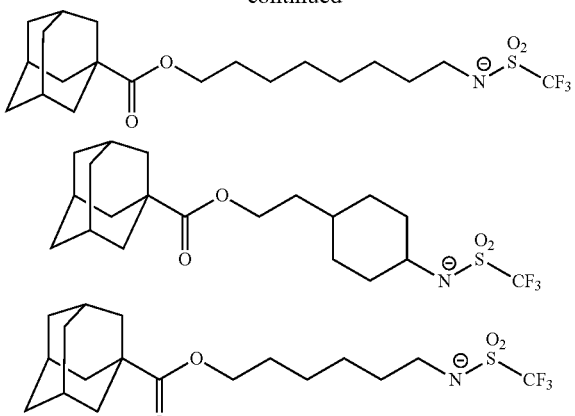

[Chemical Formula 64]

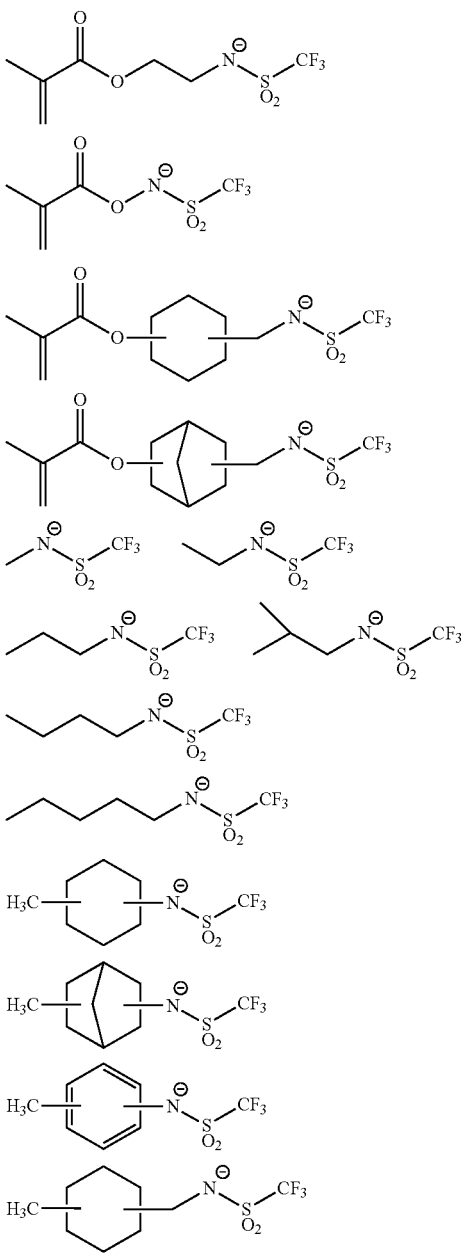

-continued

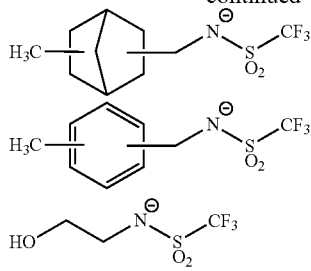

Cation Moiety

In formula (d1-3), $M^{m+}$ is an organic cation having a valency of m, and is the same as defined for $M^{m+}$ in the aforementioned formula (d1-1).

As the component (d1-3), one type of compound may be used, or two or more types of compounds may be used in combination.

As the component (D1), one type of the aforementioned components (d1-1) to (d1-3), or at least two types of the aforementioned components (d1-1) to (d1-3) can be used in combination.

When the resist composition contains the component (D1), the amount of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the amount of the component (D1) is at least as large as the lower limit of the above-mentioned range, excellent lithography properties and excellent resist pattern shape can be more reliably obtained. On the other hand, when the amount of the component (D1) is no more than the upper limit of the above-mentioned range, sensitivity can be maintained at a satisfactory level, and through-put becomes excellent.

Production Method of Component (D1):

The production methods of the components (d1-1) and (d1-2) are not particularly limited, and the components (d1-1) and (d1-2) can be produced by conventional methods.

Further, the production method of the component (d1-3) is not particularly limited, and the component (d1-3) can be produced in the same manner as disclosed in US2012-0149916.

Component (D2)

The acid diffusion control component may contain a nitrogen-containing organic compound (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine is preferable, and a secondary aliphatic amine or tertiary aliphatic amine is more preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxyl)oxyethoxy)ethyl}amine, tris {2-(2-methoxyethoxymethoxymethoxy)ethyl}amine, tris {2-(1-methoxyethoxyl)ethyl}amine, tris {2-(1-ethoxyethoxyl)ethyl}amine, tris {2-(1-ethoxypropoxyl)ethyl}amine, tris[2-{2-(2-hydroxyethoxyl)ethoxy}ethyl]amine and triethanolamine triacetate, and triethanolamine triacetate is preferable.

Further, as the component (D2), an aromatic amine may be used.

Examples of aromatic amines include 4-dimethylaminopyridine, pyrrole, indole, pyrazole, imidazole and derivatives thereof, as well as tribenzylamine, 2,6-diisopropylaniline and N-tert-butoxycarbonylpyrrolidine.

As the component (D2), one type of compound may be used alone, or two or more types may be used in combination.

When the resist composition contains the component (D2), the amount of the component (D2) is typically used in an amount within a range from 0.01 to 5 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (E): At Least One Compound Selected from the Group Consisting of Organic Carboxylic Acids, and Phosphorus Oxo Acids and Derivatives Thereof]

Furthermore, in the resist composition of the present embodiment, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

When the resist composition contains the component (E), the amount of the component (E) is typically used in an amount within a range from 0.01 to 5 parts by weight, relative to 100 parts by weight of the component (A).

[Component (F): Fluorine Additive]

In the present invention, the resist composition may further include a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

Specific examples of the component (F) include polymers having a structural unit (f1) represented by general formula (f1-1) shown below. As the polymer, a polymer (homopolymer) consisting of a structural unit (f1) represented by formula (f1-1) shown below; a copolymer of the structural unit (f1) and the aforementioned structural unit (a1); and a copolymer of the structural unit (f1), a structural unit derived from acrylic acid or methacrylic acid and the aforementioned structural unit (a1) are preferable. As the structural unit (a1) to be copolymerized with the structural unit (f1), a structural unit derived from 1-ethyl-1-cyclooctyl(meth)acrylate is preferable.

[Chemical Formula 65]

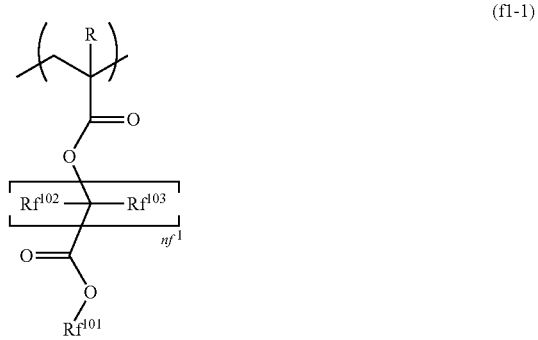

(f1-1)

In the formula, R is the same as defined above; $Rf^{102}$ and $Rf^{103}$ each independently represents a hydrogen atom, a halogen atom, an alkyl group of 1 to 5 carbon atoms, or a halogenated alkyl group of 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R bonded to the carbon atom on the α-position is the same as defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly desirable. Examples of the alkyl group of 1 to 5 carbon atoms for $Rf^{102}$ and $Rf^{103}$ include the same alkyl group of 1 to 5 carbon atoms as those described above for R, and a methyl group or an ethyl group is preferable. Specific examples of the halogenated alkyl group of 1 to 5 carbon atoms represented by $Rf^{102}$ or $R^{103}$ include groups in which part or all of the hydrogen atoms of the aforementioned alkyl groups of 1 to 5 carbon atoms have been substituted with halogen atoms.

Examples of the halogen atom include a fluorine atom, a chlorine atom, a bromine atom and an iodine atom, and a fluorine atom is particularly desirable. Among these examples, as $Rf^{102}$ and $Rf^{103}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $Rf^{101}$, a fluorinated hydrocarbon group of 1 to 5 carbon atoms is preferable, and a trifluoromethyl group, $-CH_2-CF_3$, $-CH_2-CF_2-CF_3$, $-CH(CF_3)_2$, $-CH_2-CH_2-CF_3$, and $-CH_2-CH_2-CF_2-CF_2-CF_2-CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

When the resist composition contains the component (F), the component (F) is used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, dissolution inhibitors, plasticizers, stabilizers, colorants, halation prevention agents, and dyes.

[Component (S): Organic Solvent]

The resist composition of the present embodiment can be prepared by dissolving the resist materials for the resist composition in an organic solvent (hereafter, frequently referred to as "component (S)").

The component (S) may be any organic solvent which can dissolve the respective components to give a homogeneous solution, and any organic solvent can be appropriately selected from those which have been conventionally known as solvents for a chemically amplified resist composition.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

The component (S) can be used individually, or in combination as a mixed solvent.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL or cyclohexanone is mixed as the polar solvent, the PGMEA:EL or cyclohexanone weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate. In general, the component (S) is used in an amount such that the solid content of the resist composition becomes within the range from 1 to 20% by weight, and preferably from 2 to 15% by weight.

The resist composition of the present embodiment contains, as a base resin, a polymeric compound (A1) including a structural unit (a0) which contains "-$Va^{01}$-$La^0$-$Va^{02}$-C(=O)O—$Ra^0$" on the side-chain thereof. The structural unit (a0) has an acid dissociable group $Ra^0$ at a position remote from the polymer main chain. For this reason, at the time of developing to form a resist pattern, the contact ratio of the acid dissociable group with the developing solution is high. Therefore, in the case where the developing solution is an alkali developing solution, the solubility of the exposed portions of the resist film is increased. On the other hand, in the case where the developing solution is an organic developing solution, the solubility of the unexposed portions of the resist film is increased. In either of the cases, the dissolution contrast between the exposed portions and the unexposed portions becomes large. As a result, the lithography properties are improved, and a resist pattern may be formed with an excellent shape.

By virtue of the acid dissociable group $Ra^0$ being appropriately positioned remote from the main chain of the polymer, the lithography properties are improved. However, when the acid dissociable group is too remote from the main chain of the polymer, there is a tendency that the lithography properties are deteriorated. In the present invention, for appropriately positioning the acid dissociable group $Ra^0$ remote from the main chain of the polymer, the specific structure "-$Va^{01}$-$La^0$-$Va^{02}$-C(=O)O—$Ra^0$" is selected and introduced into the side-chain of the base resin. As a result, the above effects are reliably achieved.

<<Method of Forming a Resist Pattern>>

The method of forming a resist pattern according to the second aspect of the present invention includes: using a resist composition according to the first aspect of the present invention to form a resist film on a substrate; exposing the resist film; and developing the exposed resist film to form a resist pattern.

The method for forming a resist pattern according to the present embodiment can be performed, for example, as follows.

Firstly, a resist composition of the first aspect is applied to a substrate using a spinner or the like, and a bake treatment (post applied bake (PAB)) is conducted at a temperature of 80 to 150° C. for 40 to 120 seconds, preferably 60 to 90 seconds, to form a resist film.

Subsequently, the resist film is selectively exposed, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern.

Then, baking treatment (post exposure baking (PEB)) is conducted on the exposed resist film under temperature conditions of 80 to 150° C. for 40 to 120 seconds, and preferably 60 to 90 seconds.

Next, the resist film which has been subjected to the baking treatment (PEB) is subjected to a developing treatment. The developing treatment is conducted using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinsing, the developing solution or the rinse liquid remaining on the pattern can be removed by a treatment using a supercritical fluid.

After the developing treatment or the rinse treatment, drying is conducted. If desired, bake treatment (post bake) can be conducted following the developing.

In this manner, a positive-tone resist pattern or a negative-tone resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The method of forming a resist pattern according to the present embodiment is effective to KrF excimer laser, ArF excimer laser, EB and EUV, and particularly effective to ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds. One example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used which are capable of dissolving the component (A1) (prior to exposure). Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C (=O)—C within the structure thereof. An ester solvent is an organic solvent containing C—C(=O)—O—C within the structure thereof. An alcohol solvent is an organic solvent containing an alcoholic hydroxy group within the structure thereof, and an "alcoholic hydroxy group" refers to a hydroxy group bonded to a carbon atom of an aliphatic hydrocarbon group. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of the functional groups which characterizes the aforementioned solvents within the structure thereof. In such a case, the organic solvent can be classified as any type of the solvent having the characteristic functional group. For example, diethylenegycol monomethylether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

Among these examples, as the organic solvent contained in the organic developing solution, a polar solvent is preferable, and ketone solvents, ester solvents and nitrile solvents are preferable. Specific examples of each solvent are shown below.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone).

As a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate.

As an ester solvent, butyl acetate is preferable.

Examples of nitrile solvents include acetonitrile, propionitrile, valeronitrile, butyronitrile and the like.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a fluorine surfactant or a silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1 hexanol and 2-hexanol are more preferable.

These organic solvents can be used individually, or at least 2 solvents may be mixed together. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. Examples of the additive include surfactants. As the surfactant, the same surfactants as those described above can be mentioned, and a non-ionic surfactant is preferable, and a fluorine surfactant or a silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

<<Compound>>

The compound according to a third aspect of the present invention is a compound represented by general formula (m-a0) shown below (hereafter, this compound is referred to as "compound (m-a0)").

[Chemical Formula 66]

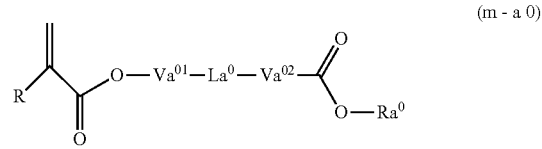

(m-a0)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^{0}$— represents $Va^{01}$-C(=O)O— or $Va^{01}$-OC(=O)—; and $Ra^{0}$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

In formula (m-a0), R, $Va^{01}$, $Va^{02}$ and $Ra^{0}$ are respectfully the same as defined for R, $Va^{01}$, $Va^{02}$ and $Ra^{0}$ in the aforementioned general formula (a0-1).

Specific examples of the compound represented by formula (m-a0) are shown below. In the formulae shown below, $R^{\alpha}$ represents a hydrogen atom, a methyl group or a trifluoromethyl group.

[Chemical Formula 67]

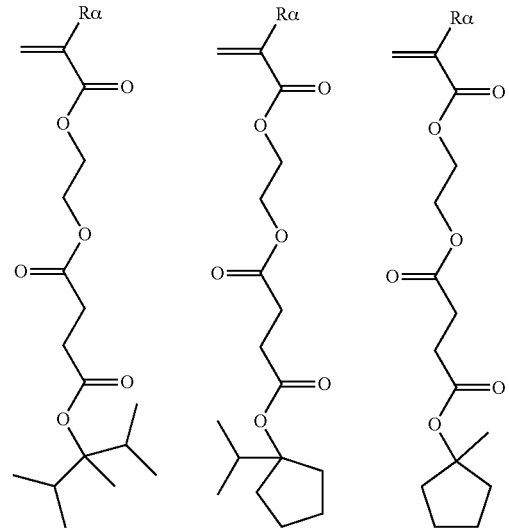

-continued

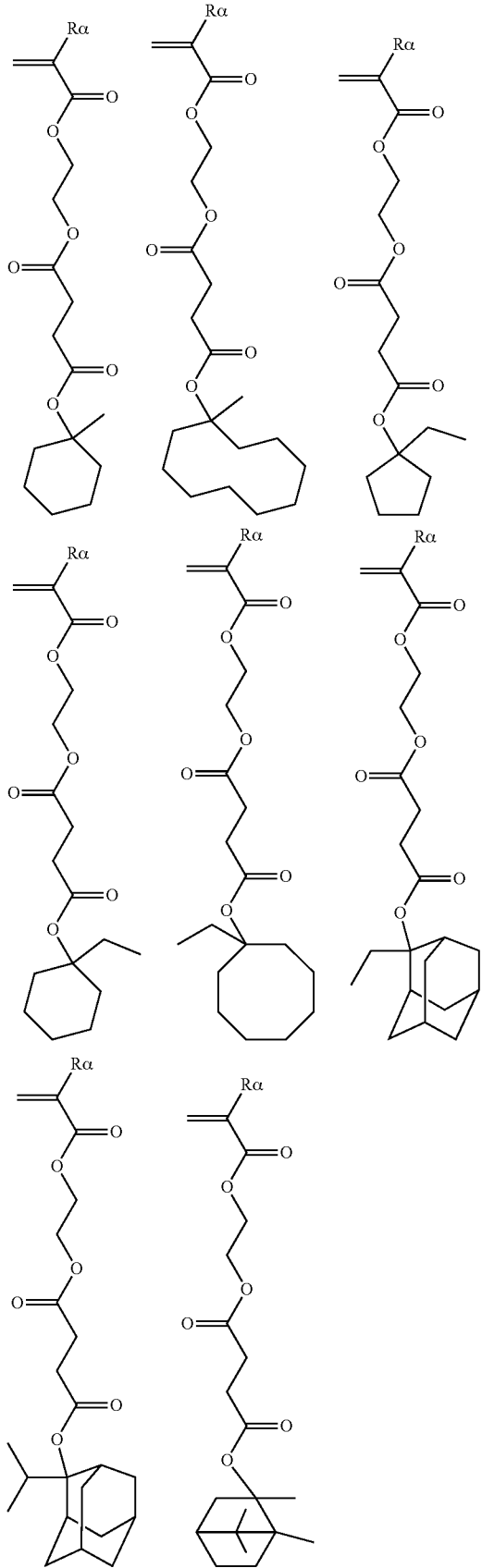

[Production Method of Compound (m-a0)]

The production method of the compound (m-a0) is not particularly limited. For example, a compound (m-a0-1) represented by general formula (m-a0-1) shown below may be reacted with a compound (m-a0-2) represented by general formula (m-a0-2) shown below, so as to produce a compound (m-a0) having $Ra^0$ as an acid dissociable group.

[Chemical Formula 68]

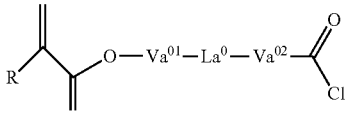
(m-a0-1)

$Ra^{0'}$—OH
(m-a0-2)

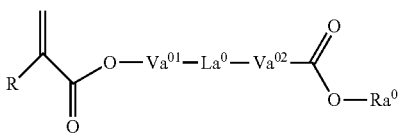
(m-a0)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-C(=O)O— or $Va^{01}$-OC(=O)—; $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded; and $Ra^{0'}$ represents a branched hydrocarbon group of 8 or more carbon atoms, a monocyclic hydrocarbon group of 4 or more carbon atoms, or a polycyclic hydrocarbon group, provided that methyl adamantyl group is excluded.

In the formula, R, $Va^{01}$, $Va^{02}$ and $Ra^0$ are the same as defined for R, $Va^{01}$, $Va^{02}$ and $Ra^0$ in the aforementioned general formula (a0-1).

The branched hydrocarbon group of 8 or more carbon atoms, monocyclic hydrocarbon group of 4 or more carbon atoms and polycyclic hydrocarbon group (excluding methyl adamantyl group) for $Ra^{0'}$ are the same as defined for the branched hydrocarbon group of 8 or more carbon atoms, monocyclic hydrocarbon group of 4 or more carbon atoms and polycyclic hydrocarbon group (excluding methyl adamantyl group) for $Ra^0$.

The compound (m-a0-1) may be reacted with the compound (m-a0-2), for example, as follows. The compound (m-a0-2) is dissolved in an appropriate organic solvent, followed by stirring in the presence of an appropriate base.

Then, the compound (m-a0-1) may be added thereto, while stirring.

In the reaction of the compound (m-a0-1) and the compound (m-a0-2), as the organic solvent, tetrahydrofuran, tert-butylmethylether, dichloromethane, acetonitrile, chloroform, methylene chloride or the like is preferable. The amount of the organic solvent relative to 100 parts by weight of the compound (m-a0-2) is preferably 50 to 1,000 parts by weight, and more preferably 100 to 600 parts by weight. As the organic solvent, one kind of compound may be used alone, or two or more kinds of compounds may be used in combination.

Examples of the base usable in the reaction of the compound (m-a0-1) and the compound (m-a0-2) include dimethylaniline and dibutylaniline. These bases may be used individually or in a combination of two or more. The amount of the base is preferably 1 to 10 mol, per 1 mol of the compound (m-a0-2).

The reaction time for the reaction of the compound (m-a0-1) and the compound (m-a0-2) depends on the reactivity of the compounds (m-a0-1) and (m-a0-2), the reaction temperature or the like. However, in general, the reaction time is preferably 0.1 to 100 hours, and more preferably 0.5 to 50 hours.

In the reaction, the reaction temperature is preferably 50 to 150° C., and more preferably 70 to 90° C.

Generally, in the reaction, the amount of the compound (m-a0-1) per 1 mol of the compound (m-a0-2) is preferably 0.5 to 10 mol, and more preferably 1 to 5 mol.

As a compound (m-a0-1) and a compound (m-a0-2), commercially available compounds may be used, or the compounds may be synthesized.

As the compound (m-a0-1) (a carboxylic acid chloride), for example, c compound obtainable by reacting a matrix carboxylic acid with an electrophilic halogenating agent such as thionyl chloride ($SOCl_2$), oxalyl chloride (($COCl)_2$) or sulfuryl chloride ($SO_2Cl_2$) may be used.

After the reaction of the compound (m-a0-1) and the compound (m-a0-2) has finished, the final objective compound (m-a0) in the reaction mixture may be separated and purified.

The separation and purification can be conducted by a conventional method. For example, any one of concentration, solvent extraction, distillation, crystallization, recrystallization and chromatography can be used alone, or two or more of these methods may be used in combination.

The structure of the compound (m-a0) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Polymeric Compound>>

The polymeric compound according to the fourth aspect of the present invention has a structural unit represented by general formula (a0-1) shown below.

[Chemical Formula 69]

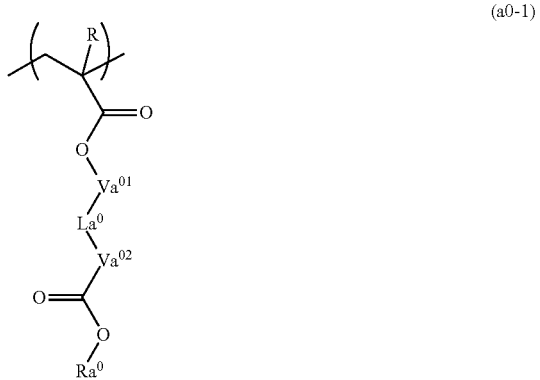

(a0-1)

In the formula, R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-C(=O)O— or $Va^{01}$-OC(=O)—; and $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

The polymeric compound according to the present embodiment preferably includes, in addition to the structural unit (a0), a structural unit containing a lactone-containing cyclic group, an —$SO_2$-containing cyclic group or a carbonate-containing cyclic group. The structural unit containing a lactone-containing cyclic group, a —$SO_2$-containing cyclic group or a carbonate-containing cyclic group is the same as defined for the aforementioned structural unit (a2).

Further, the polymeric compound according to the present embodiment preferably includes, in addition to the structural unit (a0) or in addition to the structural unit (a0) and the structural unit (a2), a structural unit containing a polar group-containing aliphatic hydrocarbon group. The structural unit containing a polar group-containing aliphatic hydrocarbon group is the same as defined for the aforementioned structural unit (a3).

The polymeric compound according to the present embodiment is the same as defined for the component (A1) (polymeric compound including a structural unit (a0)) described above in relation to the resist composition of the first aspect, and the kind of each structural unit, the amount of each structural unit and the like are the same as defined above for the component (A1).

The polymeric compounds according to the fourth aspect is obtainable, for example, by dissolving the monomers corresponding with each of the structural units in a polymerization solvent, followed by addition of a radical polymerization initiator such as azobisisobutyronitrile (AIBN) (e.g., V-601). Furthermore, in the component (F), by using a chain transfer agent such as HS—$CH_2$—$CH_2$—$CH_2$—$C(CF_3)_2$—OH, a —$C(CF_3)_2$—OH group can be introduced at the terminals of the component (F). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomer for deriving the structural unit (a0), the compound of the third aspect may be used.

The polymeric compound of the present embodiment is a novel compound useful as a base resin of a resist composition, and may be preferably blended with a resist composition as a base component (component (A1)) having a film-forming ability and exhibiting increased polarity by the action of acid.

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other chemical formulae.

<Production of Compound>

Example 1

Compound (01)

33 g of oxalyl chloride and 165 g of dichloromethane were added to a three-necked flask in a nitrogen atmosphere, and cooled to 5° C. Then, 500 g of a dichloromethane solution of a compound (0-i) (50 g) was dropwise added at the same temperature over 1 hour. Thereafter, 0.79 g of DMF was added thereto, and the temperature was raised to room temperature, followed by stirring for 2 hours. Subsequently, the reaction mixture was concentrated, so as to obtain 54 g of a compound (0-ii) as an objective compound in the form of an oily compound.

The obtained compound (0-ii) was analyzed by NMR, and the structure thereof was identified by the following results.

$^1$H-NMR (400 MHz, CDCl$_3$): δ(ppm)=6.11 (m, 1H), 5.54 (m, 1H), 4.28 (s, 4H), 3.10 (t, 2H), 2.58 (t, 2H), 1.91 (m, 3H).

[Chemical Formula 70]

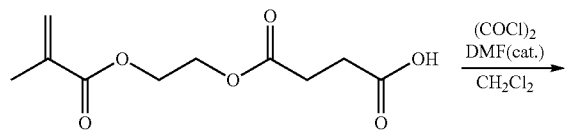

Compound (0-i)

Compound (0-ii)

Subsequently, 10.67 g of a compound (01-1), 22.8 g of dibutylaniline (DBA) and 52.0 g of acetonitrile were added to a three-necked flask in a nitrogen atmosphere, and cooled to 5° C. Then, 52.0 g of an acetonitrile solution of the compound (0-ii) (23.0 g) was dropwise added at the same temperature over 1 hour, followed by stirring at 70° C. for 8 hours. Thereafter, hexane was added to the reaction mixture, and the resultant was washed with 10 wt % hydrochloric acid, followed by washing with 1 wt % aqueous ammonia. Then, the obtained organic phase was concentrated, so as to obtain 17.5 g of a compound (01) as an ultimate objective compound in the form of an oily compound.

The obtained compound (01) was analyzed by NMR, and the structure thereof was identified by the following results.

$^1$H-NMR (400 MHz, DMSO-d6): δ(ppm)=6.08 (m, 1H), 5.66 (m, 1H), 4.31 (s, 4H), 2.62 (septet, 1H), 2.59-2.45 (m, 4H), 2.00-1.50 (m, 11H), 0.83 (d, 6H).

[Chemical Formula 71]

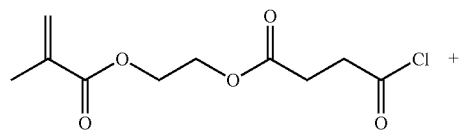

Compound (0-ii)

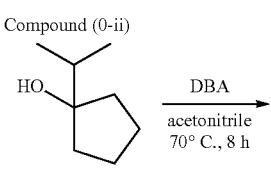

Compound (01-1)

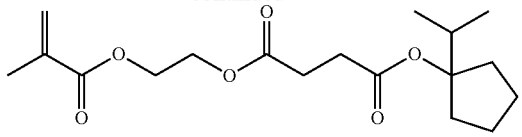

Compound (01)

Example 2

Compound (02)

9.43 g of a compound (02-1), 19.8 g of dibutylaniline and 45.0 g of acetonitrile were added to a three-necked flask in a nitrogen atmosphere, and cooled to 5° C. Then, 45.0 g of an acetonitrile solution of the compound (0-ii) (20.0 g) was dropwise added at the same temperature over 1 hour, followed by stirring at 70° C. for 8 hours. Thereafter, hexane was added to the reaction mixture, and the resultant was washed with 10 wt % hydrochloric acid, followed by washing with 1 wt % aqueous ammonia. Then, the obtained organic phase was concentrated, so as to obtain 14.4 g of a compound (02) as an ultimate objective compound in the form of an oily compound.

The obtained compound (02) was analyzed by NMR, and the structure thereof was identified by the following results.

$^1$H-NMR (400 MHz, DMSO-d6): δ(ppm)=6.03 (m, 1H), 5.70 (m, 1H), 4.27 (s, 4H), 2.60-2.45 (m, 4H), 2.20 (septet, 2H), 1.88 (s, 3H), 1.30 (s, 3H), 0.89-0.86 (m, 12H).

[Chemical Formula 72]

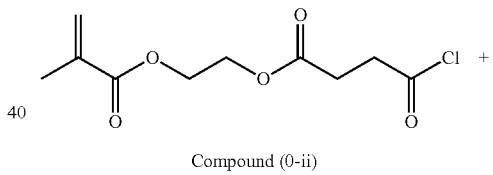

Compound (0-ii)

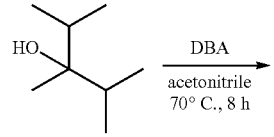

Compound (02-1)

Compound (02)

Production of Polymeric Compound

Example 3

Polymeric Compound (A1-1)

10.0 g of a compound (21), 9.2 g of the compound (01) and 4.1 g of a compound (31) were dissolved in methyl ethyl ketone (MEK), followed by dissolving 2.48 g of dimethyl azobisisobutyrate (V-601) as a polymerization initiator, so as to prepare a dripping solution. Subsequently, 12.4 g of MEK was added to a separable flask equipped with a thermometer, a reflux tube and a nitrogen feeding pipe, followed by heating at 80° C. Thereafter, at the same temperature in a nitrogen atmosphere, the dripping solution was dropwise added thereto over 4 hours. After finishing the dropwise addition, the reaction mixture was stirred at the same temperature for 1 hour. Then, the reaction liquid was cooled to room temperature. The obtained reaction liquid was dropwise added to an excess amount of methanol to deposit a polymer. Thereafter, the precipitated white powder was separated by filtration, followed by washing with methanol and drying, so as to obtain 11.5 g of a polymeric compound (A1-1) as an objective compound.

With respect to the polymeric compound (A1-1), the weight average molecular weight (Mw) and the dispersity (Mw/Mn) were determined by the polystyrene equivalent value as measured by gel permeation chromatography (GPC). As a result, it was found that the weight average molecular weight was 7,000, and the dispersity was 1.62. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n=51.1/30.9/18.0.

[Chemical Formula 73]

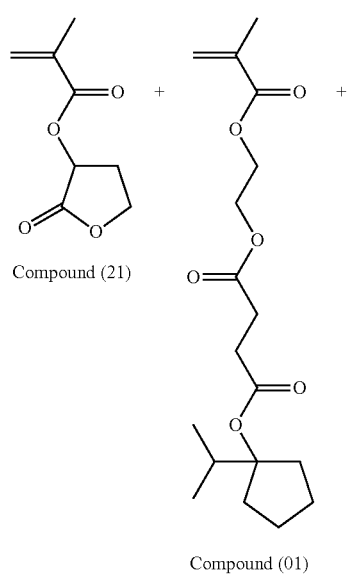

Compound (21)

Compound (01)

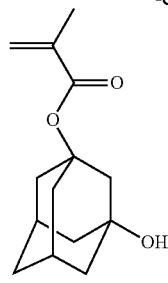

Compound (01)

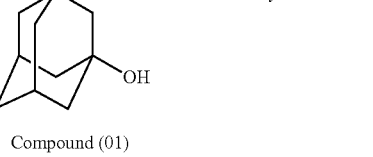

V601, MEK(80 deg. C.)
Radical Polymerization

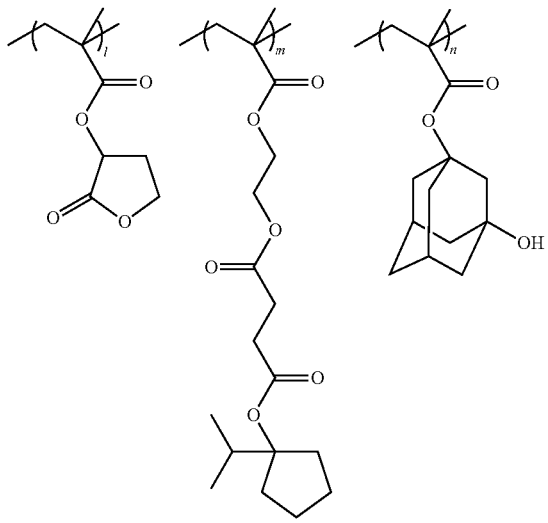

Polymeric compound (A1-1)

Example 4

Polymeric Compound (A1-2)

10.0 g of a compound (21), 9.2 g of the compound (02) and 4.1 g of a compound (31) were dissolved in methyl ethyl ketone (MEK), followed by dissolving 2.48 g of dimethyl azobisisobutyrate (V-601) as a polymerization initiator, so as to prepare a dripping solution. Subsequently, 15.78 g of MEK was added to a separable flask equipped with a thermometer, a reflux tube and a nitrogen feeding pipe, followed by heating at 80° C. Thereafter, at the same temperature in a nitrogen atmosphere, the dripping solution was dropwise added thereto over 4 hours. After finishing the dropwise addition, the reaction mixture was stirred at the same temperature for 1 hour. Then, the reaction liquid was cooled to room temperature. The obtained reaction liquid was dropwise added to an excess amount of methanol to deposit a polymer. Thereafter, the precipitated white powder was separated by filtration, followed by washing with methanol and drying, so as to obtain 11.5 g of a polymeric compound (A1-2) as an objective compound.

With respect to the polymeric compound (A1-2), the weight average molecular weight (Mw) and the dispersity (Mw/Mn) were determined by the polystyrene equivalent value as measured by gel permeation chromatography (GPC). As a result, it was found that the weight average molecular weight was 6,500, and the dispersity was 1.65. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n=51.7/29.5/18.8.

[Chemical Formula 74]

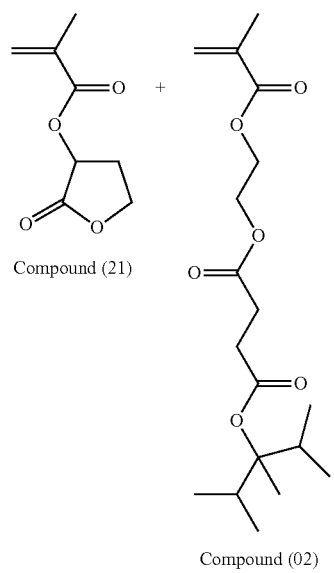

Compound (21)  Compound (02)

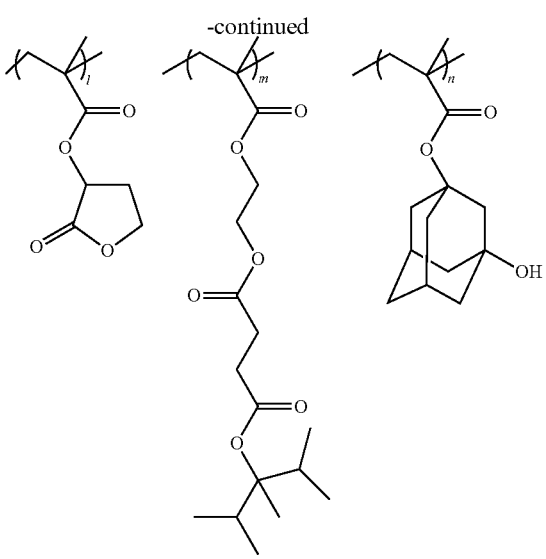

Polymeric compound (A1-2)

Example 5

Polymeric Compound (A1-3)

Polymerization and other procedures were conducted in the same manner as in Example 3, except that, as the monomers, a compound (61) shown below was used in addition to the compounds (21), (01) and (31), so as to obtain a polymeric compound (A1-3) as an objective compound.

With respect to the polymeric compound (A1-3), the weight average molecular weight (Mw) and the dispersity (Mw/Mn) were determined by the polystyrene equivalent value as measured by gel permeation chromatography (GPC). As a result, it was found that the weight average molecular weight was 7,100, and the dispersity was 1.71. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n/o=50.4/24.3/20.6/4.7.

[Chemical Formula 75]

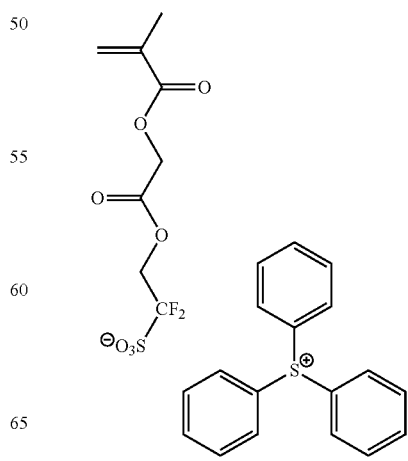

Compound (61)

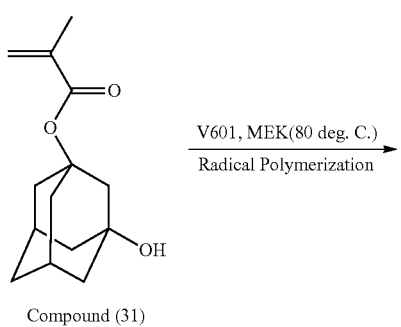

Compound (31)

V601, MEK(80 deg. C.)
Radical Polymerization

-continued

Polymeric compound (A1-3)

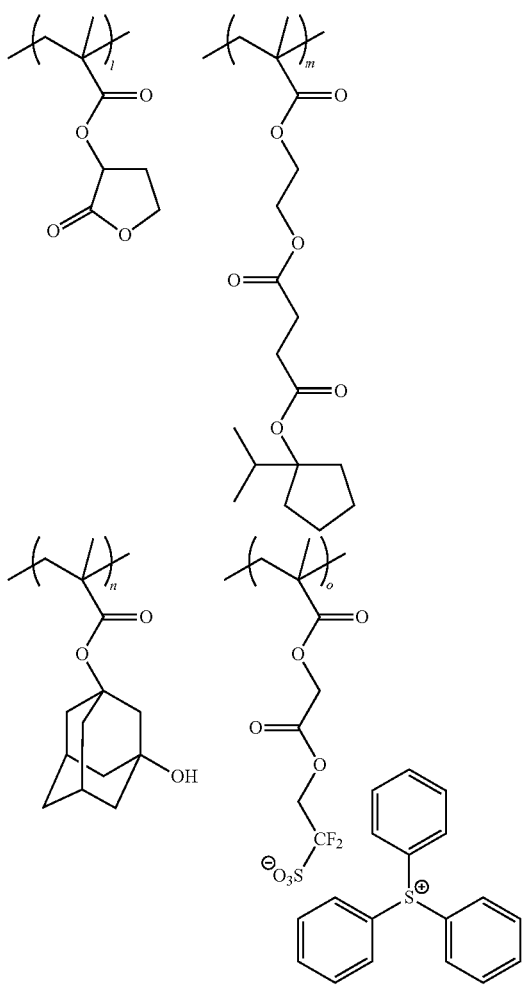

Example 6

Polymeric Compound (A1-4)

Polymerization and other procedures were conducted in the same manner as in Example 3, except that a compound (03) shown below was used instead of the compound (01), so as to obtain a polymeric compound (A1-4) as an objective compound.

With respect to the polymeric compound (A1-4), the weight average molecular weight (Mw) and the dispersity (Mw/Mn) were determined by the polystyrene equivalent value as measured by gel permeation chromatography (GPC). As a result, it was found that the weight average molecular weight was 6,800, and the dispersity was 1.67. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n=51.1/30.2/18.7.

[Chemical Formula 76]

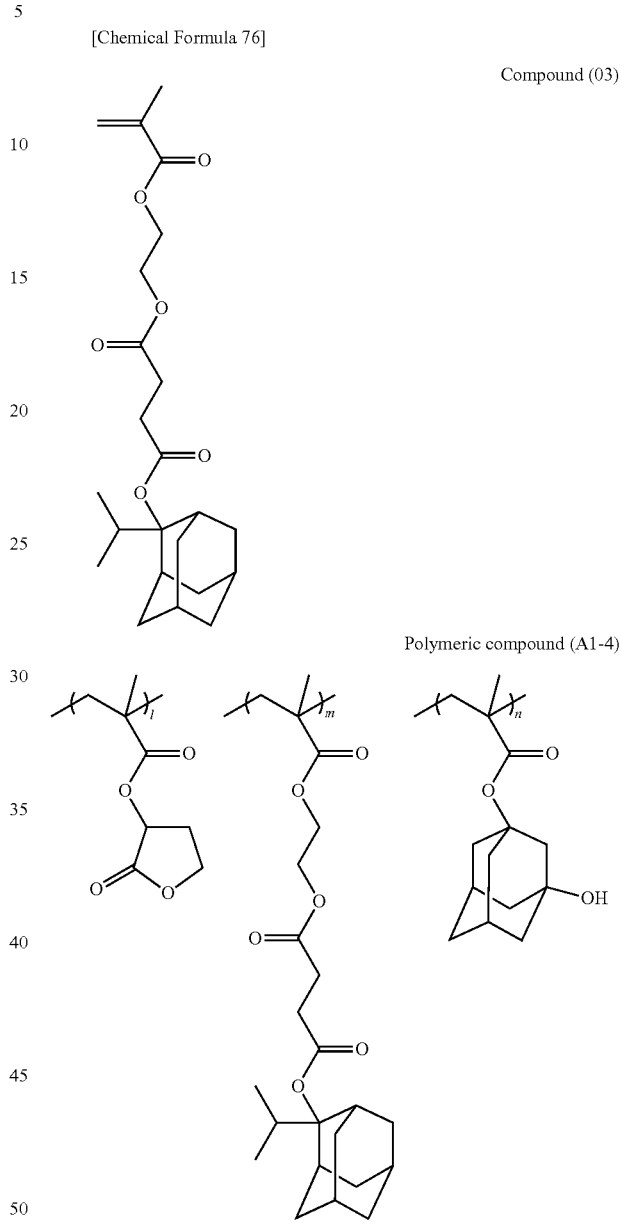

Compound (03)

Polymeric compound (A1-4)

<Production of Resist Composition>

Examples 7 to 10

Comparative Examples 1 to 6

The components shown in Table 1 were mixed together and dissolved to obtain each resist composition.

TABLE 1

|  | Component (A) | Component (B) | Component (D) | Component (E) | Component (F) | Component (S) | |
|---|---|---|---|---|---|---|---|
| Ex. 7 | (A)-1 [100] | (B)-1 [15] | (D)-1 [5.15] | (E)-1 [0.2] | (F)-1 [4.0] | (S)-1 [100] | (S)-2 [4000] |

TABLE 1-continued

|  | Component (A) | Component (B) | Component (D) | Component (E) | Component (F) | Component (S) | |
|---|---|---|---|---|---|---|---|
| Ex. 8 | (A)-2 [100] | (B)-1 [15] | (D)-1 [5.15] | (E)-1 [0.2] | (F)-1 [4.0] | (S)-1 [100] | (S)-2 [4000] |
| Comp. Ex. 1 | (A)-3 [100] | (B)-1 [15] | (D)-1 [5.15] | (E)-1 [0.2] | (F)-1 [4.0] | (S)-1 [100] | (S)-2 [4000] |
| Comp. Ex. 2 | (A)-4 [100] | (B)-1 [15] | (D)-1 [5.15] | (E)-1 [0.2] | (F)-1 [4.0] | (S)-1 [100] | (S)-2 [4000] |
| Comp. Ex. 3 | (A)-5 [100] | (B)-1 [15] | (D)-1 [5.15] | (E)-1 [0.2] | (F)-1 [4.0] | (S)-1 [100] | (S)-2 [4000] |
| Comp. Ex. 4 | (A)-6 [100] | (B)-1 [15] | (D)-1 [5.15] | (E)-1 [0.2] | (F)-1 [4.0] | (S)-1 [100] | (S)-2 [4000] |
| Ex. 9 | (A)-7 [100] | — | (D)-1 [5.15] | (E)-1 [0.2] | (F)-1 [4.0] | (S)-1 [100] | (S)-2 [4000] |
| Comp. Ex. 5 | (A)-8 [100] | — | (D)-1 [5.15] | (E)-1 [0.2] | (F)-1 [4.0] | (S)-1 [100] | (S)-2 [4000] |
| Ex. 10 | (A)-9 [100] | (B)-1 [15] | (D)-1 [5.15] | (E)-1 [0.2] | (F)-1 [4.0] | (S)-1 [100] | (S)-2 [4000] |
| Comp. Ex. 6 | (A)-10 [100] | (B)-1 [15] | (D)-1 [5.15] | (E)-1 [0.2] | (F)-1 [4.0] | (S)-1 [100] | (S)-2 [4000] |

In Table 1, the reference characters indicate the following. The values in brackets [ ] indicate the amount (in terms of parts by weight) of the component added.

(A)-1: the aforementioned polymeric compound (A1-1)

(A)-2: the aforementioned polymeric compound (A1-2)

(A)-3 to (A)-6: polymeric compounds represented by the following chemical formulae (A)-3 to (A)-6

(A)-3: Polymeric compound represented by chemical formula (A)-3 shown below. The weight average molecular weight (Mw) and the dispersity (Mw/Mn) in terms of the polystyrene equivalent value measured by gel permeation chromatography (GPC) were 7,100 and 1.66, respectively. The composition of the copolymer (ratio (molar ratio) of the respective structural units within the structural formula) as determined by $^{13}$C-NMR was l/m/n=48.6/30.3/21.1.

(A)-4: Polymeric compound represented by chemical formula (A)-4 shown below. The weight average molecular weight (Mw) and the dispersity (Mw/Mn) in terms of the polystyrene equivalent value measured by gel permeation chromatography (GPC) were 6,800 and 1.51, respectively. The composition of the copolymer (ratio (molar ratio) of the respective structural units within the structural formula) as determined by $^{13}$C-NMR was l/m/n=50.5/29.3/20.2.

(A)-5: Polymeric compound represented by chemical formula (A)-5 shown below. The weight average molecular weight (Mw) and the dispersity (Mw/Mn) in terms of the polystyrene equivalent value measured by gel permeation chromatography (GPC) were 7,200 and 1.59, respectively. The composition of the copolymer (ratio (molar ratio) of the respective structural units within the structural formula) as determined by $^{13}$C-NMR was l/m/n=50.8/30.1/19.1.

(A)-6: Polymeric compound represented by chemical formula (A)-6 shown below. The weight average molecular weight (Mw) and the dispersity (Mw/Mn) in terms of the polystyrene equivalent value measured by gel permeation chromatography (GPC) were 6,900 and 1.68, respectively. The composition of the copolymer (ratio (molar ratio) of the respective structural units within the structural formula) as determined by $^{13}$C-NMR was l/m/n=50.3/30.9/18.8.

(A)-7: the aforementioned polymeric compound (A1-3)

(A)-8: Polymeric compound represented by chemical formula (A)-8 shown below. The weight average molecular weight (Mw) and the dispersity (Mw/Mn) in terms of the polystyrene equivalent value measured by gel permeation chromatography (GPC) were 7,400 and 1.75, respectively. The composition of the copolymer (ratio (molar ratio) of the respective structural units within the structural formula) as determined by $^{13}$C-NMR was l/m/n/o=50.4/24.9/20.0/4.7.

(A)-9: the aforementioned polymeric compound (A1-4)

(A)-10: Polymeric compound represented by chemical formula (A)-10 shown below. The weight average molecular weight (Mw) and the dispersity (Mw/Mn) in terms of the polystyrene equivalent value measured by gel permeation chromatography (GPC) were 6,800 and 1.68, respectively. The composition of the copolymer (ratio (molar ratio) of the respective structural units within the structural formula) as determined by $^{13}$C-NMR was l/m/n=50.3/29.8/19.9.

[Chemical Formula 77]

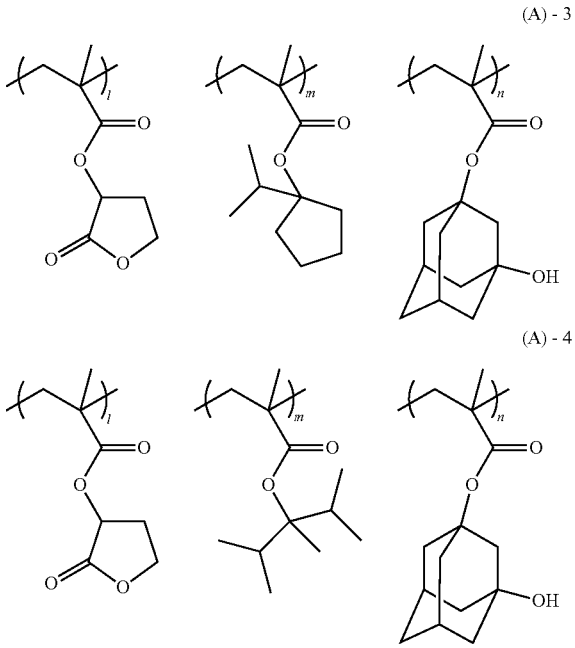

(A)-5

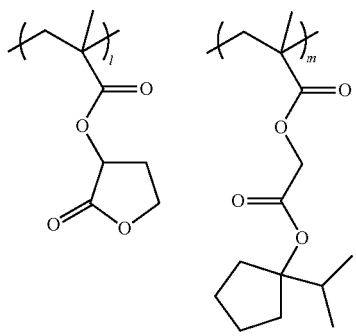

(A)-6

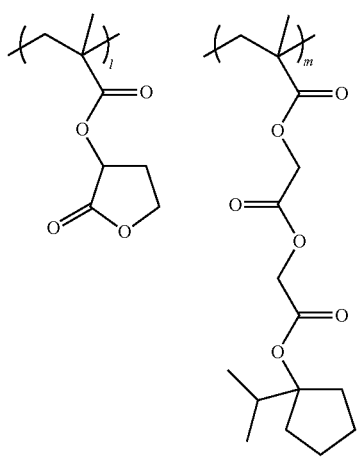

(A)-8

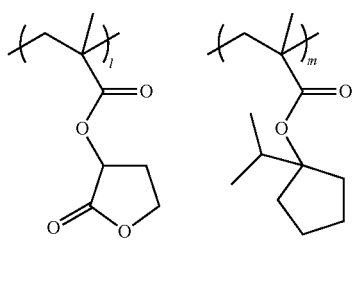

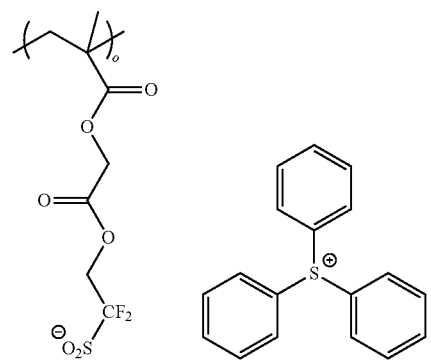

(A)-10

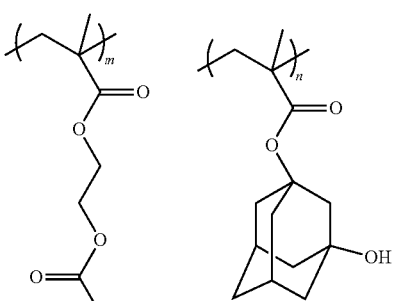

(B)-1: a compound represented by chemical formula (B)-1 shown below (D)-1: a compound represented by chemical formula (D)-1 shown below (E)-1: salicylic acid (F)-1: fluorine-containing polymeric compound represented by chemical formula (F)-1 below. The weight average molecular weight (Mw) and the dispersity (Mw/Mn) in terms of the polystyrene equivalent value measured by gel permeation chromatography (GPC) were 23,100 and 1.78, respectively. The composition of the copolymer (ratio (molar ratio) of the respective structural units within the structural formula) as determined by $^{13}$C-NMR was l/m=77/23.

(S)-1: γ-butyrolactone (S)-2: a mixed solvent of PGMEA/PGME/cyclohexanone=45/30/25 (weight ratio)

[Chemical Formula 78]

(B)-1

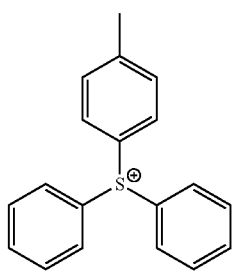

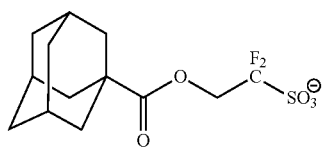

-continued

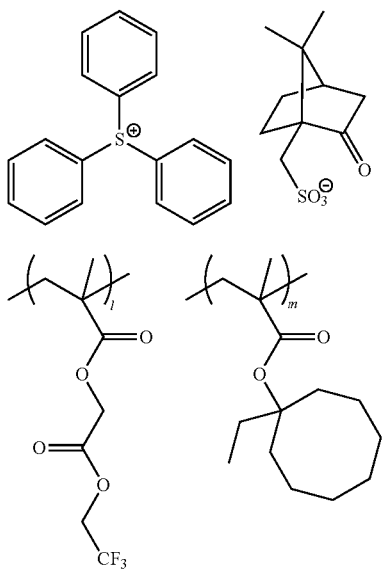

(D)-1

(F)-1

<Formation of Resist Pattern (1): Positive-Tone Developing Process>

An organic anti-reflection film composition (product name: ARC95, manufactured by Brewer Science Ltd.) was applied to an 12-inch silicon wafer using a spinner, and the composition was then baked at 205° C. for 60 seconds and dried, thereby forming an organic anti-reflection film having a film thickness of 90 nm.

Then, each of the resist compositions of Examples 7 to 10 and Comparative Examples 1 to 6 was applied to the organic antireflection film, and was then prebaked (PAB) on a hotplate at 110° C. for 60 seconds and dried, thereby forming a resist film having a film thickness of 90 nm.

Subsequently, the resist film was selectively irradiated with an ArF excimer laser (193 nm) through a photomask, using an immersion lithography ArF exposure apparatus NSR-S609B (manufactured by Nikon Corporation; NA (numerical aperture)=1.07; Dipole 0.97/0.78 w/P; immersion medium: water).

Then, a post exposure bake (PEB) treatment was conducted at 95° C. for 60 seconds.

Thereafter, alkali developing was conducted for 10 seconds at 23° C. in a 2.38% by weight aqueous solution of tetramethylammonium hydroxide (TMAH) (product name: NMD-3; manufactured by Tokyo Ohka Kogyo Co., Ltd.).

As a result, in each of the examples, a line and space pattern was formed.

In each of the examples, a line and space pattern having a line width of 50 nm and a pitch of 100 nm was formed.

[Evaluation of Optimum Exposure Dose (Eop)]

The optimum exposure dose Eop (mJ/cm$^2$) with which a line and space pattern having a target size (line width of 50 nm and pitch of 100 nm) was formed in the "Formation of resist pattern (1)" was determined. The results are indicated under "Eop (mJ/cm$^2$)" in Table 2.

[Evaluation of Exposure Latitude (EL Margin)]

In the "Formation of resist pattern (1)", the exposure dose with which a line and space pattern having a line width of about ±5% of the target dimension (line width of 50 nm) was determined, and the EL margin (unit: %) was determined by the following formula. The results are indicated "5% EL (%)" in Table 2.

EL margin (%)=(|E1−E2|/Eop)×100

E1: Exposure dose (mJ/cm$^2$) with which a line and space pattern having a line width of 47.5 nm was formed E2: Exposure dose (mJ/cm$^2$) with which a line and space pattern having a line width of 52.5 nm was formed The larger the value of the "EL margin", the smaller the change in the pattern size by the variation of the exposure dose.

[Evaluation of Line Width Roughness (LWR)]

With respect to each of the line and space patterns formed in the "Formation of resist pattern (1)" having a line width of 50 nm and a pitch of 100 nm, the line width at 400 points in the lengthwise direction of the line were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are indicated under "LWR (nm)" in Table 2.

The smaller this 3s value is, the lower the level of roughness of the line width, indicating that a line and space pattern with a uniform width was obtained.

[Evaluation of Mask Error Factor (MEEF)]

In accordance with the same procedure as in the "Formation of resist pattern (1)", a line and space pattern having a pitch of 100 nm was formed with the same exposure dose and using a mask pattern in which the target size of the line width was 45 to 55 nm (11 target sizes at intervals of 1 nm).

The value of the mask error factor was determined as the gradient of a graph obtained by plotting the target size (nm) on the horizontal axis, and the line width (nm) of the pattern formed on the resist film using each mask pattern on the vertical axis. The results are indicated under "MEEF" in Table 2.

A MEEF value (gradient of the plotted line) closer to 1 indicates that a resist pattern faithful to the mask pattern was formed.

TABLE 2

| Positive-tone developing process | Eop (mJ/cm$^2$) | 5% EL (%) | LWR (nm) | MEEF |
| --- | --- | --- | --- | --- |
| Example 7 | 18.1 | 6.40 | 2.91 | 2.01 |
| Example 8 | 17.1 | 6.78 | 2.81 | 1.91 |
| Comparative Example 1 | 28.5 | 4.87 | 3.72 | 2.46 |
| Comparative Example 2 | 25.1 | 5.01 | 3.68 | 2.31 |
| Comparative Example 3 | 24.7 | 5.11 | 3.60 | 2.22 |
| Comparative Example 4 | 22.1 | 5.07 | 3.49 | 2.25 |
| Example 9 | 19.4 | 6.98 | 2.75 | 1.95 |
| Comparative Example 5 | 30.1 | 4.92 | 3.52 | 2.43 |
| Example 10 | 20.4 | 5.40 | 3.27 | 2.21 |
| Comparative Example 6 | 31.5 | 4.92 | 4.50 | 2.89 |

As seen from the results shown in Table 2, in the formation of a resist pattern by a positive-tone developing process, the resist compositions of Examples 7 to 10 exhibited excellent lithography properties and pattern shape, as compared to Comparative Examples 1 to 6.

<Formation of Resist Pattern (2): Negative-Tone Developing Process>

On a 12-inch silicon wafer, an organic anti-reflection film with a film thickness of 72 nm was formed. Then, on the organic anti-reflection film, an inorganic anti-reflection film with a film thickness of 14 nm was laminated.

Each of the resist compositions of Examples 7, 8 and 10 and Comparative Examples 1 to 4 and 6 was applied to the inorganic antireflection film using a spinner, and was then prebaked (PAB) on a hot plate at 110° C. for 50 seconds and dried, so as to form a resist film having a film thickness of 85 nm.

Subsequently, the resist film was selectively irradiated with an ArF excimer laser (193 nm) through a photomask, using an immersion lithography ArF exposure apparatus NSR-S609B (manufactured by Nikon Corporation; NA (numerical aperture)=1.07; Annular 0.78/0.97 w/o P).

Then, a post exposure bake (PEB) treatment was conducted at 90° C. for 50 seconds.

Next, a solvent development was conducted at 23° C. for 31 seconds using butyl acetate, followed by drying by shaking.

As a result, in each of the examples, a space and line pattern (hereafter, referred to as "SL pattern") having a space width of 47 nm and a pitch of 110 nm was formed.

[Evaluation of Optimum Exposure Dose (Eop)]

The optimum exposure dose Eop (mJ/cm$^2$) with which an SL pattern having a target size (line width of 47 nm and pitch of 110 nm) was formed in the "Formation of resist pattern (2)" was determined. The results are indicated under "Eop (mJ/cm$^2$)" in Table 3.

[Evaluation of Exposure Latitude (EL Margin)]

In the "Formation of resist pattern (2)", the exposure dose with which a space and line pattern having a space width of about ±5% of the target dimension (space width of 47 nm) was determined, and the EL margin (unit: %) was determined by the following formula. The results are indicated "5% EL (%)" in Table 3.

EL margin (%)=(|E3−E4|/Eop)×100

E3: Exposure dose (mJ/cm$^2$) with which an SL pattern having a space width of 44.65 nm was formed E4: Exposure dose (mJ/cm$^2$) with which an SL pattern having a space width of 49.35 nm was formed

[Evaluation of Line Width Roughness (LWR)]

With respect to each of the SL patterns formed in the "Formation of resist pattern (2)" having a space width of 47 nm and a pitch of 110 nm, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are indicated under "LWR (nm)" in Table 3.

[Evaluation of Mask Error Factor (MEEF)]

In accordance with the same procedure as in the "Formation of resist pattern (2)", an SL pattern having a pitch of 110 nm was formed with the same exposure dose and using a mask pattern in which the target size of the space width was 42 to 52 nm (11 target sizes at intervals of 1 nm).

The value of the mask error factor was determined as the gradient of a graph obtained by plotting the target size (nm) on the horizontal axis, and the space width (nm) of the pattern formed on the resist film using each mask pattern on the vertical axis. The results are indicated under "MEEF" in Table 3.

TABLE 3

| Negative-tone developing process | Eop (mJ/cm$^2$) | 5% EL (%) | LWR (nm) | MEEF |
| --- | --- | --- | --- | --- |
| Example 7 | 17.4 | 5.19 | 3.11 | 1.85 |
| Example 8 | 17.0 | 5.43 | 3.07 | 1.79 |
| Comparative Example 1 | 22.1 | 3.65 | 4.11 | 2.11 |
| Comparative Example 2 | 21.0 | 4.31 | 3.78 | 2.32 |
| Comparative Example 3 | 20.7 | 4.21 | 3.67 | 1.98 |
| Comparative Example 4 | 19.8 | 4.51 | 3.46 | 1.91 |
| Example 10 | 21.3 | 5.12 | 3.34 | 1.91 |
| Comparative Example 6 | 27.4 | 4.71 | 4.10 | 2.41 |

As seen from the results shown in Table 3, in the formation of a resist pattern by a positive-tone developing process, the resist compositions of Examples 7, 8 and 10 exhibited excellent lithography properties and pattern shape, as compared to Comparative Examples 1 to 4 and 6.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates acid upon exposure and exhibits changed solubility in a developing solution under action of acid, the resist composition comprising:
    a base component (A) which exhibits changed solubility in a developing solution under action of acid, the base component (A) comprising a polymeric compound (A1) comprising a structural unit (a0) represented by general formula (a0-1) shown below:

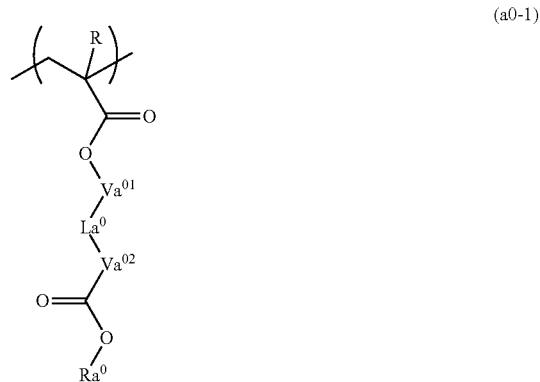

wherein R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-OC(=O)—; and $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

2. The resist composition according to claim 1, wherein the polymeric compound (A1) further comprises a structural unit (a2) containing a lactone-containing cyclic group, an —$SO_2$— containing cyclic group or a carbonate-containing cyclic group.

3. The resist composition according to claim 1, wherein the polymeric compound (A1) further comprises a structural unit (a3) containing a polar group-containing aliphatic hydrocarbon group.

4. The resist composition according to claim 1, wherein $Va^{01}$ and $Va^{02}$ each independently represents a linear alkylene group of 2 to 10 carbon atoms.

5. The resist composition according to claim 1, wherein $Ra^0$ represents an acid dissociable, branched hydrocarbon group of 8 or more carbon atoms or an acid dissociable, monocyclic hydrocarbon group of 4 or more carbon atoms.

6. The resist composition according to claim 5, wherein $Ra^0$ represents an acid dissociable, branched hydrocarbon group of 8 or more carbon atoms.

7. A method of forming a resist pattern, comprising:
forming a resist film on a substrate using the resist composition of claim 1;
exposing the resist film; and
developing the exposed resist film to form a resist pattern.

8. A compound represented by general formula (m-a0) shown below:

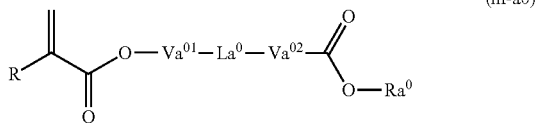

(m-a0)

wherein R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-OC(=O)—; and $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

9. The compound according to claim 8, wherein $Va^{01}$ and $Va^{02}$ each independently represents a linear alkylene group of 2 to 10 carbon atoms.

10. The compound according to claim 8, wherein $Ra^0$ represents an acid dissociable, branched hydrocarbon group of 8 or more carbon atoms or an acid dissociable, monocyclic hydrocarbon group of 4 or more carbon atoms.

11. The compound according to claim 10, wherein $Ra^0$ represents an acid dissociable, branched hydrocarbon group of 8 or more carbon atoms.

12. A polymeric compound comprising a structural unit represented by general formula (a0-1) shown below:

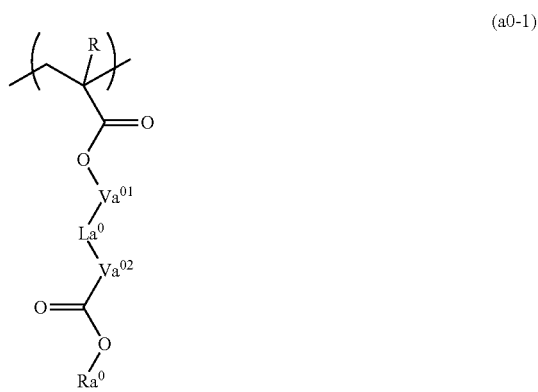

(a0-1)

wherein R represents a hydrogen atom, an alkyl group of 1 to 5 carbon atoms or a halogenated alkyl group of 1 to 5 carbon atoms; $Va^{01}$ and $Va^{02}$ each independently represents a hydrocarbon group of 2 to 10 carbon atoms; $Va^{01}$-$La^0$— represents $Va^{01}$-OC(=O)—; and $Ra^0$ represents an acid dissociable, branched hydrocarbon group of 8 or more carbon atoms, an acid dissociable, monocyclic hydrocarbon group of 4 or more carbon atoms, or an acid dissociable, polycyclic hydrocarbon group, provided that methyl adamantyl group is excluded.

13. The polymeric compound according to claim 12, further comprising a structural unit containing a lactone-containing cyclic group, an —$SO_2$— containing cyclic group or a carbonate-containing cyclic group.

14. The polymeric compound according to claim 12, further comprising a structural unit containing a polar group-containing aliphatic hydrocarbon group.

15. The polymeric compound according to claim 12, wherein $Va^{01}$ and $Va^{02}$ each independently represents a linear alkylene group of 2 to 10 carbon atoms.

16. The polymeric compound according to claim 12, wherein $Ra^0$ represents an acid dissociable, branched hydrocarbon group of 8 or more carbon atoms or an acid dissociable, monocyclic hydrocarbon group of 4 or more carbon atoms.

17. The polymeric compound according to claim 16, wherein $Ra^0$ represents an acid dissociable, branched hydrocarbon group of 8 or more carbon atoms.

* * * * *